United States Patent
Hunt et al.

(10) Patent No.: US 10,548,302 B2
(45) Date of Patent: Feb. 4, 2020

(54) FIBRILLIN-1 MUTATIONS FOR MODELING NEONATAL PROGEROID SYNDROME WITH CONGENITAL LIPODYSTROPHY

(71) Applicant: Regeneron Pharmaceuticals, Inc., Tarrytown, NY (US)

(72) Inventors: Charleen Hunt, Dumont, NJ (US); Jason Mastaitis, Yorktown Heights, NY (US); Guochun Gong, Pleasantville, NY (US); Ka-Man Venus Lai, Seattle, WA (US); Jesper Gromada, Concord, MA (US); Aris N. Economides, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 20 days.

(21) Appl. No.: 15/663,410

(22) Filed: Jul. 28, 2017

(65) Prior Publication Data
US 2018/0027782 A1    Feb. 1, 2018

Related U.S. Application Data

(60) Provisional application No. 62/368,924, filed on Jul. 29, 2016.

(51) Int. Cl.
*A01K 67/027* (2006.01)
*A61K 49/00* (2006.01)
*C07K 14/78* (2006.01)

(52) U.S. Cl.
CPC ...... *A01K 67/0275* (2013.01); *A61K 49/0008* (2013.01); *C07K 14/78* (2013.01); *A01K 2217/056* (2013.01); *A01K 2227/105* (2013.01); *A01K 2267/0306* (2013.01)

(58) Field of Classification Search
CPC ............ A01K 67/0275; A01K 2217/00; A01K 2217/056; A01K 2227/105; A01K 2267/0306; A61K 49/0008; C07K 14/78
See application file for complete search history.

(56) References Cited

FOREIGN PATENT DOCUMENTS

WO    WO 2015/084625 A1    6/2015
WO    WO 2018/023014 A1    2/2018

OTHER PUBLICATIONS

Wakchaure et al., IJETAE 5(11), 210-213, 2015.*
Cao et al., J. of Exp. Zoo., 311A: 368-376, 2009.*
Brevini et al., Theriogenology, 74: 544-550, 2010.*
Paris et al., Theriogenology, 74: 516-524, 2010.*
Munoz et al., Theriogenology, (69): 1159-1164, 2008.*
Gomez et al., Theriogenology, (74): 498-515, 2010.*
Jean et al. Develop. Growth Differ., (55): 41-51, 2013.*
Graham et al., Genome Biology, 16:260, 2014.*
Niemann, Transgenic Research, 7: 73-75 (1998).*
Clark et al. Nature Reviews: 4: 825-833, 2003.*
Chen, M., et al., "Truncated C-terminus of fibrillin-1 induces Marfanoid-progeroid-lipodystrophy (MPL) syndrome in rabbit," Disease Models and Mechanisms, 11(4):dmm031542, (Apr. 9, 2018).
"The FBN1 mutations database: The gene," [Retrieved from the Internet Jul. 28, 2017: <URL: http://www.umd.be/FBN1/W_FBN1/gene.shtml>].
Biggin et al, "Detection of Thirty Novel FBN1 Mutations in Patients With Marfan Syndrome or a Related Fibrillinopathy," *Hum. Mutat.* 23(1):99, (2004).
Caputi et al., "A nonsense mutation in the fibrillin-1 gene of a Marfan syndrome patient induces NMD and disrupts an exonic splicing enhancer," *Genes Dev.* 16(14):1754-1759, (2002).
Carta et al., "Fibrillins 1 and 2 Perform Partially Overlapping Functions during Aortic Development," *J. Biol. Chem.* 281(12):8016-8023, (2006).
Charbonneau, "In Vivo Studies of Mutant Fibrillin-1 Microfibrils," *J. Biol. Chem.* 285(32):2493-24955, (2010).
Chopra, "The Role of FBN1 in mammalian energy balance" [Retrieved from the Internet May 5, 2016 <URL: http://grantome.com/grant/NIH/K08-DK102529-01>].
Cook et al. "Generation of Fbn1 conditional null mice implicate the extracellular microfibrils in osteoprogenitor recruitment," *Genesis* 50(8):635-641, (2012).
Dietz et al., "Four Novel FBN1 Mutations: Significance for Mutant Transcript Level and EGF-like Domain Calcium Binding in the Pathogenesis of Marfan Syndrome," *Genomics* 17:468-475, (1993).
Eadie et al., "Genetic Analysis of a Family with a Novel Type I Fibrillinopathy," *J AAPOS* 18(2):134-139, (2014).
Fernandes et al., "Identification of Loci Modulating the Cardiovascular and Skeletal Phenotypes of Marfan Syndrome in Mice," *Sci. Rep.* 6:22426, (2016).
Ferruzzi et al., "Mechanical assessment of elastin integrity in fibrillin-1-deficient carotid arteries: implications for Marfan syndrome," *Cardiovascular Research* 92:287-295, (2011).
Goldblatt et al.,"Furher Evidence for a Maranoid Syndome with Neonatal Progeroid Features and Severe Generalized Lipodystrophy Due to Frameshift Mutations Near the 3' End of the FBN1 Gene," *Am. J. Med. Genet. A.* 155A(4):717-720, (2011).
Graul-Neumann et al., "Marfan Syndrome with Neonatal Progeroid Syndrome-Like Lipodystrophy Associated with Novel Frameshift Mutation at the 3' Terminus of the FBN1-Gene," *Am. J. Med. Genet. A.* 152A(11):2749-2755, (2010).

(Continued)

Primary Examiner — Thaian N Ton
(74) *Attorney, Agent, or Firm* — Brian A. Cocca; Alston & Bird, LLP

(57) ABSTRACT

Provided are non-human animals comprising a mutation in the Fbn1 gene to model neonatal progeroid syndrome with congenital lipodystrophy (NPSCL). Also provided are methods of making such non-human animal models. The non-human animal models can be used for screening compounds for activity in inhibiting or reducing NPSCL or ameliorating NPSCL-like symptoms or screening compounds for activity potentially harmful in promoting or exacerbating NPSCL as well as to provide insights in to the mechanism of NPSCL and potentially new therapeutic and diagnostic targets.

30 Claims, 11 Drawing Sheets
Specification includes a Sequence Listing.

(56) References Cited

OTHER PUBLICATIONS

Halliday et al., "Twelve novel FBN1 mutations in Marfan syndrome and Marfan related phenotypes test the feasibility of FBN1 mutation testing in clinical practice," *J. Med. Genet.* 39(8):589-593, (2002).
Horn and Robinson, "Progeroid Facial Features and Lipodystrophy Associated with a Novel Splice Site Mutation in the Final Intron of the FBN1 Gene," *Am. J. Med. Genet. A.* 155A(4):721-724, (2011).
Hou et al., "Natural Course of Neonatal Progeroid Syndrome," *Pediatr. Neonatol.* 50(3):102-109, (2009).
Jacquinet et al., "Neonatal progeroid variant of Marfan syndrome with congenital lipodystrophy results from mutations at the 3' end of FBN1 gene," *Eur. J. Med. Genet.* 57(5):230-234, (2014).
Jensen et al., "C-terminal propeptide is required for fibrillin-1 secretion and blocks premature assembly through linkage to domains cbEGF41-43," *Proc. Natl. Acad. Sci. U.S.A.* 111(28):10155-10160, (2014).
Jensen et al., "Dissecting the Fibrillin Microfibril: Structural Insights into Organization and Function," *Structure* 20(2):215-225, (2012).
Judge et al., "Evidence for a critical contribution of haploinsufficiency in the complex pathogenesis of Marfan syndrome," *J. Clin. Invest.* 114(2):172-181, (2004).
Kainulainen et al., "Two mutations in Marfan syndrome resulting in truncated fibrillin polypeptides," *Proc. Natl. Acad. Sci. U.S.A.* 89:5917-5921, (1992).
Le Gloan et al., "Neonatal Marfan Syndrome: Report of a Case with an Inherited Splicing Mutation outside the Neonatal Domain," *Mol. Syndromol.* 6:281-286, (2015).
Lee et al., "Losartan Attenuates Degradation of Aorta and Lung Tissue Micromechanics in a Mouse Model of Severe Marfan Syndrome," *Ann. Biomed. Eng.* 44(10):2994-3006, (2016).
Lima et al., "A New Mouse Model for Marfan Syndrome Presents Phenotypic Variability Associated with the Genetic Background and Overall Levels of Fbn1 Expression," *PLoS One* 5(11):e14136, (2010).
Loeys, "The search for genotype/phenotype correlation in Marfan syndrome: to be or not to be," *Eur. Heart J.* 37(43):3291-3293, (2016).
Mariko et al., "Fibrillin-1 genetic deficiency leads to pathological aging of arteries in mice," *J. Pathol.* 224(1):33-44, (2011).
Pereira et al., "Pathogenetic sequence for aneurysm revealed in mice underexpressing fibrillin-1," *Proc. Natl. Acad. Sci. U.S.A.* 96:3819-3823, (1999).
Pereira et al., "Targetting of the gene encoding fibrilin-1 recapitulates the vascular aspect of Marfan syndrome," *Nat. Genet.* 17(2):218-222, (1997).
Raghunath et al., "Analyses of truncated fibrillin caused by a 366 bp deletion in the FBN1 gene resulting in Marfan syndrome," *Biochem. J.* 302:889-896, (1994).
Regalado et al., "Pathogenic FBN1 Variants in Familial Thoracic Aortic Aneurysms and Dissections," *Clin. Genet.* 89(6):719-723, (2016).
Romere et al., "Asprosin, a Fasting-Induced Glucogenic Protein Hormone," *Cell* 165(3):566-579, (2016).
Schrijver et al., "Premature Termination Mutations in FBN1: Distinct Effects on Differential Allelic Expression and on Protein and Clinical Phenotypes," *Am. J. Hum. Genet.* 71:223-237, (2002).
Siracusa et al., "A Tandem Duplication within the fibrillin 1 Gene Is Associated with the Mouse Tight skin Mutation," *Genome Res.* 6(4):300-313, (1996).
Stheneur et al., "Prognosis Factors in Probands With an FBN1 Mutation Diagnosed Before the Age of 1 Year," *Pediatr. Res.* 69(3):265-270, (2011).
Takenouchi et al., "Severe Congenital Lipodystrophy and a Progeroid Appearance: Mutation in the Penultimate Exon of FBN1 Causing a Recognizable Phenotype," *Am. J. Med. Genet. A.* 161A(12):3057-3062, (2013).
Tjeldhorn et al., "Qualitative and quantitative analysis of FBN1 mRNA from 16 patients with Marfan Syndrome," *BMC Medical Genetics*: 16:113, (2015).
Umeyama et al., "Generation of heterozygous fibrillin-1 mutant cloned pigs from genome-edited foetal fibroblasts," *Sci. Rep.* 6:24413, (2016).
Wang et al., "Postmortem diagnosis of Marfan syndrome in a case of sudden death due to aortic rupture: Detection of a novel FBN1 frameshift mutation," *Forensic Sci. Int.* 261:e1-e4, (2016).
Xu et al., "Abnormal fibrillin-1 expression and chronic oxidative stress mediated endothelial mesenchymal transition in a murine model of systemic sclerosis," *Am. J. Physiol. Cell. Physiol.* 300:C550-C556, (2011).
Yang et al., "Human embryonic stem cells derived from abnormal blastocyst donated by Marfan syndrome patient," *Stem Cell Research* 15:640-642, (2015).
Campens et al., "Intrinsic cardiomyopathy in Marfan syndrome: results from in-vivo and ex-vivo studies of the Fbn1C1039G/+ model and longitudinal findings in humans," *Pediatric Research*, 78(3):256-263, (2015).
Carta et al., "p38 MAPK Is an Early Determinant of Promiscuous Smad2/3 Signaling in the Aortas of Fibrillin-1 (Fbn1)-null mice," *The Journal of Biological Chemistry*, 284(9):5630-5636, (2009).
Davis et al., "Expression of FBN1 during adipogenesis: Relevance to the lipodystrophy phenotype in Marfan syndrome and related conditions," *Molecular Genetics and Metabolism*, 119:174-185, (2016).
Garg et al., "De Novo Heterozygous FBN1 Mutations in the Extreme C-Terminal Region Cause Progeroid Fibrillinopathy," *American Journal of Medical Genetics Part A*, 164A:1341-1345, (2014).
Mizuguchi et al., "Recent progress in genetics of Marfan syndrome and Marfan-associated disorders," *J. Hum. Genet.*, 52:1-12, (2007).
Neptune et al., "Dysregulation of TGF-β activation contributes to pathogenesis in Marfan syndrome," *Nature Genetics*, 33:407-411, (2003).
Passarge et al., "Marfanoid-progeroid-lipodystrophy syndrome: a newly recognized fibrillinopathy," *European Journal of Human Genetics*, 24:1244-1247, (2016).
Saito et al., "Indication of Skin Fibrosis in Mice Expressing a Mutated Fibrillin-1 Gene," *Molecular Medicine*, 6(10):825-836, (2000).
Sakai et al., "FBN1: The disease-causing gene for Marfan syndrome and other genetic disorders," *Gene*, 591:279-291, (2016).
Tae et al., "Cardiac remodeling in the mouse model of Marfan syndrome develops into two distinctive phenotypes," *Am. J. Physiol. Heart Circ. Physiol.*, 310:H290-H299, (2016).
Umeyama et al., "Supplementary Information: Generation of heterozygous fibrillin-1 mutant cloned pigs from genome-edited foetal fibroblasts," Apr. 14, 2016. [Retrieved from the Internet Nov. 8, 2017: <https://www.ncbi.nlm.nih.gov/pmc/articles/PMC4830947/bin/srep24413-s1.pdf>].
Zeyer et al., "Engineered mutations in fibrillin-1 leading to Marfan syndrome act at the protein, cellular and organismal levels," *Mutation Research*, 765:7-18, (2015).
PCT International Search Report and Written Opinion of the International Searching Authority for application PCT/US2017/044409 dated Oct. 13, 2017.
Duerrschmid, C., et al., "Asprosin is a centrally acting orexigenic hormone," Nature Medicine, 23(12):1444-1453, (2017).

\* cited by examiner

| Fibrillin-1 Alleles | Sequence (Nucleotide Amino Acid) | SEQ ID NO |
|---|---|---|
| Human WT | ... CGG AGA AGC ACA AAC GAA ACT GAT ...<br>... R R / S T N E T D ... | 1<br>2 |
| Human Variant | ... CGG AGA AGC ACA AAC GAA AAC TGA<br>... R R / S T N E N * | 3<br>4 |
| Mouse WT | ... CGG AGA AGC ACG AAC GAA ACG GAT ...<br>... R R / S T N E T D ... | 5<br>6 |
| Engineered Mouse Variant MAID 8501 | ... CGG AGA AGC ACG AAC GAA AAC TGA<br>... R R / S T N E N * | 7<br>8 |

| Fibrillin-1 Alleles | Sequence (Nucleotide Amino Acid) | SEQ ID NO |
|---|---|---|
| Human WT | ...GAGTGTGTAAGATCAATGGCTACCCCAAAACGGGGCAGGAAGCGGAGAAGCACAAACGAAACT... <br> ... E  C   *    I   N   G   Y   P   K   K   R   G   R   K   R   R / S   T   N   E   T ... | 9 <br> 10 |
| Human Variant | ...GAGTGTGTGATCAATGGCTACCCCAAAACGGGGCAGGAAGCGGAGAAGCACAAACGAAACTGA... <br> ... E  C   D   Q   W   L   P   Q   T   G   Q   E   T   E   K   H   H   K   R   N   * | 11 <br> 12 |
| Mouse WT | ...GAGTGTGTAAGATCAACGGCTACCCCAAAGAGGCCGGCCGAAAACGGAGAAGCACAAACGAAACT... <br> ... E  C   *    I   N   G   Y   P   K   R / G   R   K   R   R / S   T   N   E   T ... | 13 <br> 14 |
| Engineered Mouse Variant MAID 8502 | ...GAGTGTGTGATCAATGGCTACCCCCAAACGGGGCAGGAGAAGCACAAACGAAACTGA... <br> ... E  C   D   Q   W   L   P   Q   T   G   Q   E   T   E   K   H   H   K   R   N   * | 15 <br> 16 |
| MAID 8520 | PPASSEMDDN SLSPEACYEC ⸨KINGYPKAAQ SHLPATRPET EKHERNGCLR HPGRV⸩ | 17 |
| Expected MAID 8502 | PPASSEMDDN SLSPEACYEC ⸨DQWLPQTGQE TEKHKRN⸩ | 18 |

FIG. 3

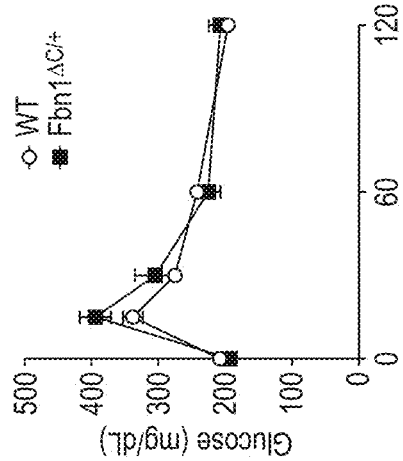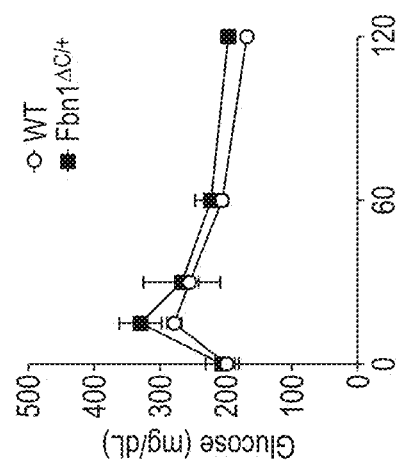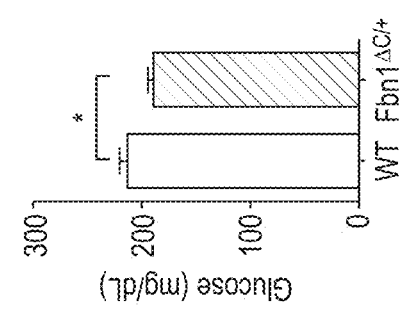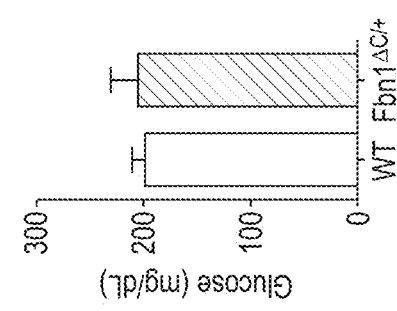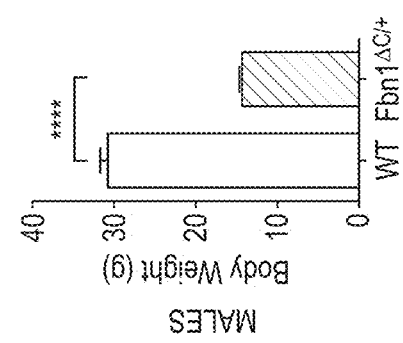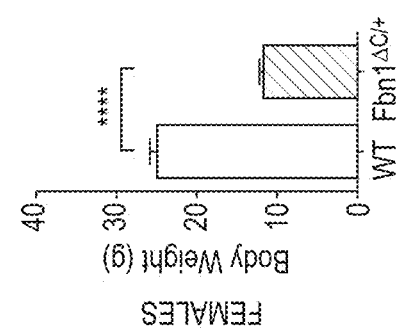

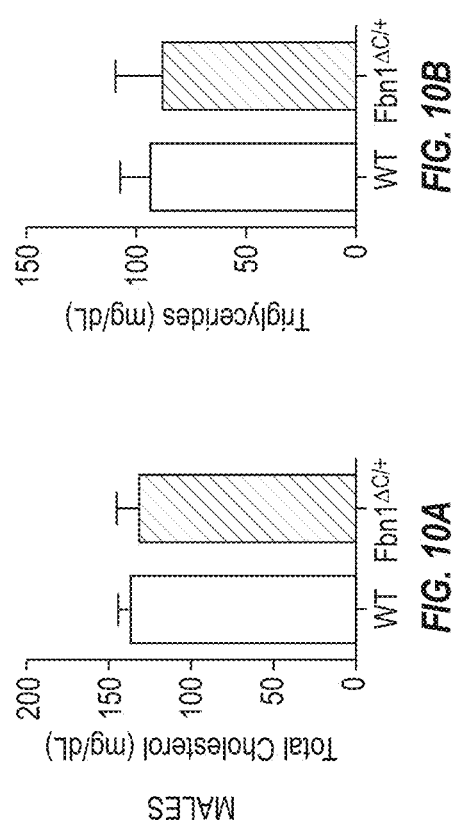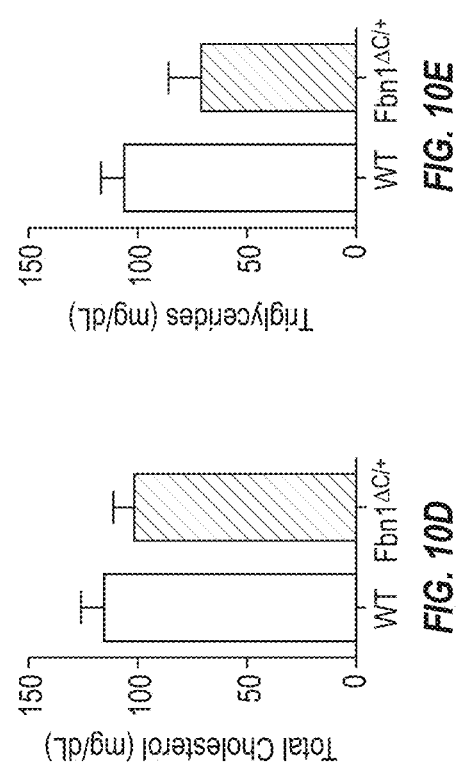
FIG. 10A, FIG. 10B, FIG. 10C, FIG. 10D, FIG. 10E, FIG. 10F

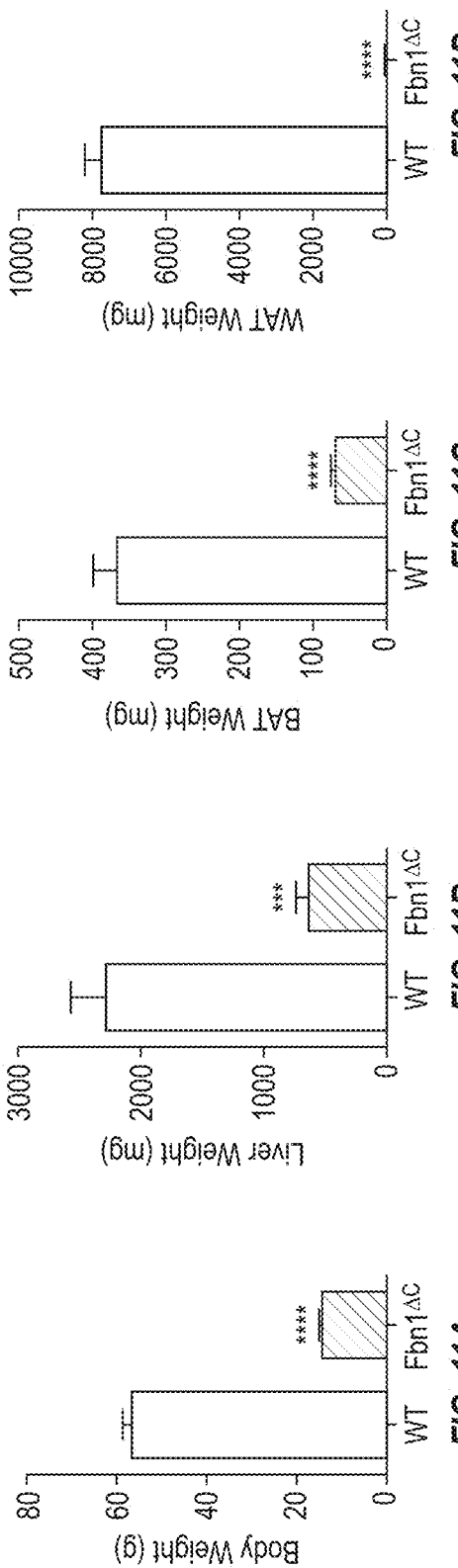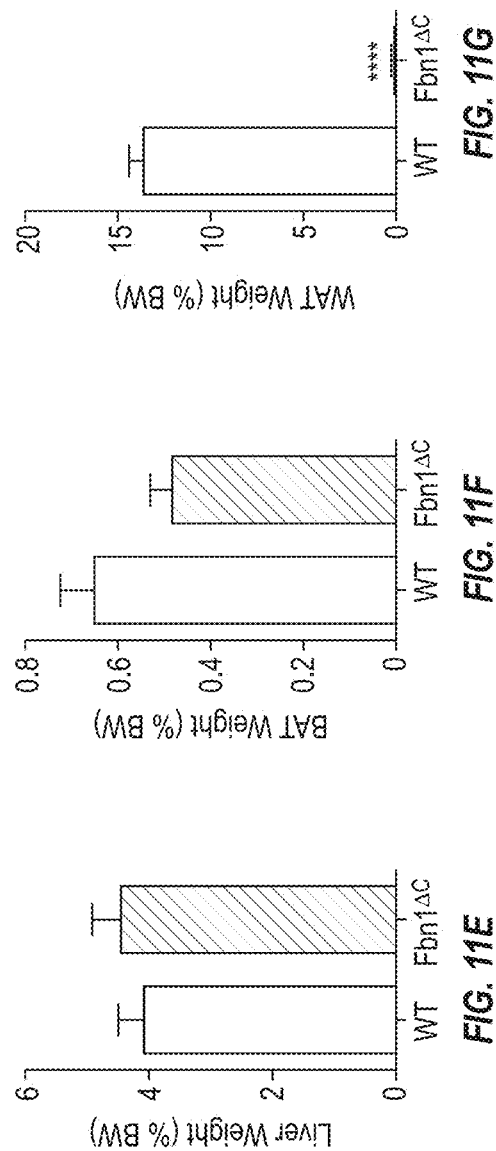

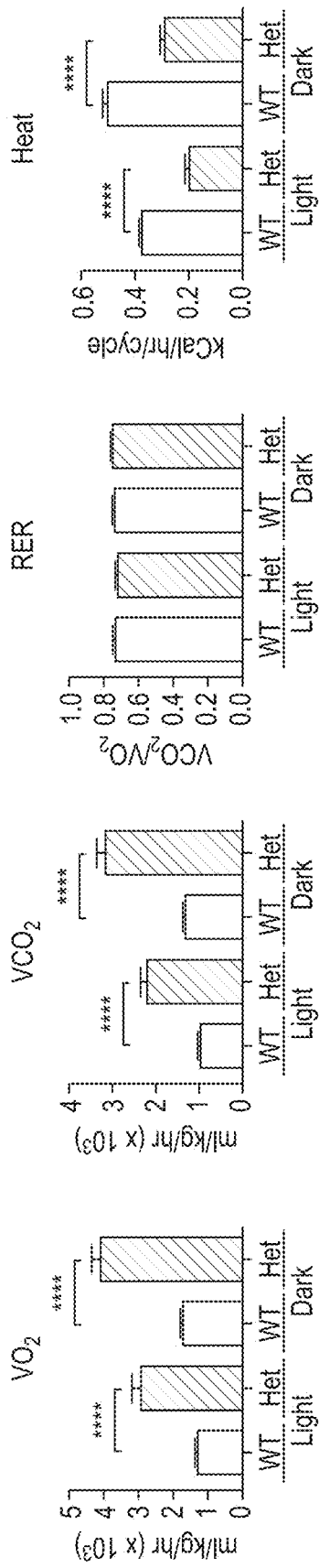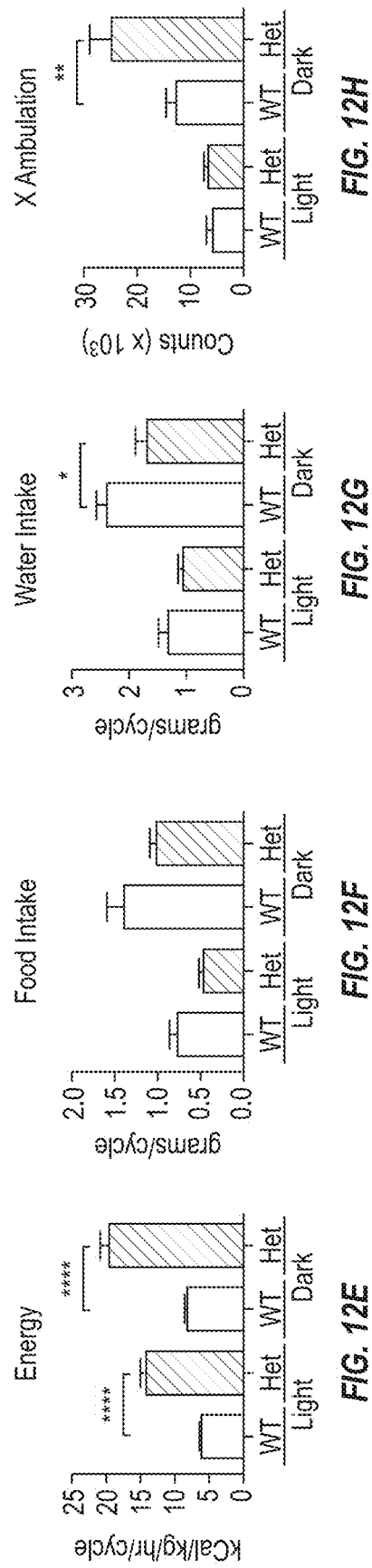

SEQUENCE LISTING

```
<160> NUMBER OF SEQ ID NOS: 47

<210> SEQ ID NO 1
<211> LENGTH: 24
<212> TYPE: DNA
<213> ORGANISM: Homo sapiens

<400> SEQUENCE: 1
cggagaagca caaacgaaac tgat                                              24

<210> SEQ ID NO 2
<211> LENGTH: 8
<212> TYPE: PRT
<213> ORGANISM: Homo sapiens

<400> SEQUENCE: 2

Arg Arg Ser Thr Asn Glu Thr Asp
1               5

<210> SEQ ID NO 3
<211> LENGTH: 24
<212> TYPE: DNA
<213> ORGANISM: Homo sapiens

<400> SEQUENCE: 3
cggagaagca caaacgaaaa ctga                                              24

<210> SEQ ID NO 4
<211> LENGTH: 7
<212> TYPE: PRT
<213> ORGANISM: Homo sapiens

<400> SEQUENCE: 4

Arg Arg Ser Thr Asn Glu Asn
1               5
```

<210> SEQ ID NO 5
<211> LENGTH: 24
<212> TYPE: DNA
<213> ORGANISM: Mus musculus

<400> SEQUENCE: 5
cggagaagca cgaacgaaac ggat                                    24

<210> SEQ ID NO 6
<211> LENGTH: 8
<212> TYPE: PRT
<213> ORGANISM: Mus musculus

<400> SEQUENCE: 6

Arg Arg Ser Thr Asn Glu Thr Asp
1               5

<210> SEQ ID NO 7
<211> LENGTH: 24
<212> TYPE: DNA
<213> ORGANISM: Artificial Sequence
<220> FEATURE:
<223> OTHER INFORMATION: Synthetic

<400> SEQUENCE: 7
cggagaagca cgaacgaaaa ctga                                    24

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

Arg Arg Ser Thr Asn Glu Asn
1               5

<210> SEQ ID NO 9
<211> LENGTH: 60
<212> TYPE: DNA
<213> ORGANISM: Homo sapiens

<400> SEQUENCE: 9
gagtgtaaga tcaatggcta ccccaaacgg ggcaggaaac ggagaagcac aaacgaaact    60

<210> SEQ ID NO 10
<211> LENGTH: 20
<212> TYPE: PRT
<213> ORGANISM: Homo sapiens

<400> SEQUENCE: 10

Glu Cys Lys Ile Asn Gly Tyr Pro Lys Arg Gly Arg Lys Arg Arg Ser
1               5                   10                  15

Thr Asn Glu Thr
            20

<210> SEQ ID NO 11
<211> LENGTH: 60
<212> TYPE: DNA
<213> ORGANISM: Homo sapiens

<400> SEQUENCE: 11
gagtgtgatc aatggctacc ccaaacgggg caggaaacgg agaagcacaa acgaaactga    60

<210> SEQ ID NO 12
<211> LENGTH: 19
<212> TYPE: PRT
<213> ORGANISM: Homo sapiens

<400> SEQUENCE: 12

Glu Cys Asp Gln Trp Leu Pro Gln Thr Gly Gln Glu Thr Glu Lys His
1               5                   10                  15

Lys Arg Asn

<210> SEQ ID NO 13
<211> LENGTH: 60
<212> TYPE: DNA
<213> ORGANISM: Mus musculus

<400> SEQUENCE: 13
gagtgtaaga tcaacggcta cccaaaacga ggccggaaac ggagaagcac gaacgaaacg    60

<210> SEQ ID NO 14
<211> LENGTH: 20
<212> TYPE: PRT
<213> ORGANISM: Mus musculus

<400> SEQUENCE: 14

Glu Cys Lys Ile Asn Gly Tyr Pro Lys Arg Gly Arg Lys Arg Arg Ser
1               5                   10                  15

Thr Asn Glu Thr
            20

<210> SEQ ID NO 15
<211> LENGTH: 60
<212> TYPE: DNA
<213> ORGANISM: Artificial Sequence
<220> FEATURE:
<223> OTHER INFORMATION: Synthetic

<400> SEQUENCE: 15
gagtgtgatc aatggctacc ccaaacgggg caggaaacgg agaagcacaa acgaaactga    60

<210> SEQ ID NO 16
<211> LENGTH: 19
<212> TYPE: PRT
<213> ORGANISM: Artificial Sequence
<220> FEATURE:
<223> OTHER INFORMATION: Synthetic

<400> SEQUENCE: 16

Glu Cys Asp Gln Trp Leu Pro Gln Thr Gly Gln Glu Thr Glu Lys His
1               5                   10                  15

Lys Arg Asn

<210> SEQ ID NO 17
<211> LENGTH: 55
<212> TYPE: PRT
<213> ORGANISM: Artificial Sequence
<220> FEATURE:
<223> OTHER INFORMATION: Synthetic

<400> SEQUENCE: 17

Pro Pro Ala Ser Ser Glu Met Asp Asp Asn Ser Leu Ser Pro Glu Ala
1               5                   10                  15

```
Cys Tyr Glu Cys Lys Ile Asn Gly Tyr Pro Lys Ala Ala Gln Ser His
             20                  25                  30

Leu Pro Ala Thr Arg Pro Glu Thr Glu Lys His Glu Arg Asn Gly Cys
         35                  40                  45

Leu Arg His Pro Gly Arg Val
         50                  55

<210> SEQ ID NO 18
<211> LENGTH: 37
<212> TYPE: PRT
<213> ORGANISM: Artificial Sequence
<220> FEATURE:
<223> OTHER INFORMATION: Synthetic

<400> SEQUENCE: 18

Pro Pro Ala Ser Ser Glu Met Asp Asp Asn Ser Leu Ser Pro Glu Ala
1               5                   10                  15

Cys Tyr Glu Cys Asp Gln Trp Leu Pro Gln Thr Gly Gln Glu Thr Glu
             20                  25                  30

Lys His Lys Arg Asn
         35

<210> SEQ ID NO 19
<211> LENGTH: 8616
<212> TYPE: DNA
<213> ORGANISM: Homo sapiens

<400> SEQUENCE: 19
```

| | | |
|---|---|---|
| atgcgtcgag gccgtctgct ggagatcgcc ctgggattta ccgtgctttt agcgtcctac | 60 |
| acgagccatg gggcggacgc caatttggag gctgggaacg tgaaggaaac cagagccagt | 120 |
| cgggccaaga gaagaggcgg tggaggacac gacgcgctta aggacccaa tgtctgtgga | 180 |
| tcacgttata atgcttactg ttgccctgga tggaaaacct acctggcgg aaatcagtgt | 240 |
| attgtcccca tttgccggca ttcctgtggg atggattttt gttcgaggcc aaatatgtgc | 300 |
| acttgcccat ctggtcagat agctccttcc tgtggctcca gatccataca acactgcaat | 360 |
| attcgctgta tgaatggagg tagctgcagt gacgatcact gtctatgcca gaaaggatac | 420 |
| atagggactc actgtggaca acctgtttgt gaaagtggct gtctcaatgg aggaaggtgt | 480 |
| gtggccccaa atcgatgtgc atgcacttac ggatttactg acccagtg tgaaagagat | 540 |
| tacaggacag gcccatgttt tactgtgatc agcaaccaga tgtgccaggg acaactcagc | 600 |
| gggattgtct gcacaaaaac gctctgctgt gccacagtcg gccgagcctg ggccacccc | 660 |
| tgtgagatgt gtcctgccca gcctcacccc tgccgcgtg gcttcattcc aaatatccgc | 720 |
| acggagctt gtcaagatgt ggatgaatgc aggccatcc ccgggctctg tcagggagga | 780 |
| aattgcatta atactgttgg gtcttttgag tgcaaatgcc ctgctggaca caacttaat | 840 |
| gaagtgtcac aaaaatgtga agatattgat gaatgcagca ccattcctgg aatctgtgaa | 900 |
| gggggtgaat gtacaaacac agtcagcagt tactttgca aatgtccccc tggtttttac | 960 |
| acctctccag atggtaccag atgcatagat gttcgcccag atactgtta cacagctctg | 1020 |
| acaaacgggc gctgctctaa ccagctgcca cagtccataa ccaaaatgca gtgctgctgt | 1080 |
| gatgccggcc gatgctggtc tccaggggtc actgtcgccc ctgagatgtg tccatcaga | 1140 |
| gcaaccgagg atttcaacaa gctgtgctct gttcctatgg taattcctgg gagaccagaa | 1200 |
| tatcctcccc caccccttgg ccccattcct ccagttctcc ctgttcctcc tggctttcct | 1260 |
| cctggacctc aaattccggt ccctcgacca ccagtggaat atctgtatcc atctcgggag | 1320 |

```
ccaccaaggg tgctgccagt aaacgttact gattactgcc agttggtccg ctatctctgt   1380
caaaatggac gctgcattcc aactcctggg agttaccggt gtgagtgcaa caaagggttc   1440
cagctggacc tccgtgggga gtgtattgat gttgatgaat gtgagaaaaa cccctgtgct   1500
ggtggtgagt gtattaacaa ccagggttcg tacacctgtc agtgccgagc tggatatcag   1560
agcacactca cgcggacaga atgccgagac attgatgagt gtttacagaa tggccggatc   1620
tgcaataatg gacgctgcat caacacagat ggcagttttc attgcgtgtg taatgcgggc   1680
tttcatgtta cacgagatgg gaagaactgt gaagatatgg atgaatgcag cataaggaac   1740
atgtgcctta tggaatgtgt atcaatgaa gatggcagtt ttaaatgtat ttgcaaacct   1800
ggattccagc tggcatcaga tggacgttat tgcaaagaca ttaacgagtg tgaaacccct   1860
gggatctgca tgaatgggcg ttgcgtcaac actgatggct cctacagatg tgaatgcttc   1920
cctggactgg ctgtgggtct ggatggccgt gtgtgtgttg acacacacat gcggagcaca   1980
tgctatggtg gatacaagag aggccagtgt atcaaacctt tgtttggtgc tgtcactaaa   2040
tctgaatgct gttgcgccag cactgagtat gcatttgggg aaccttgcca gccgtgtcct   2100
gcacagaatt cagcggaata tcaggcactc tgcagcagtg ggccaggaat gacgtcagca   2160
ggcagtgata taaatgaatg tgcactagat cctgatattt gcccaaatgg aatctgtgaa   2220
aaccttcgtg ggacctataa atgtatatgc aattcaggat atgaagtgga ttcaactggg   2280
aaaaactgcg ttgatattaa tgaatgtgta ctgaacagtc tcctttgtga caatggacaa   2340
tgtagaaata ctcctggaag ttttgtctgt acctgcccca agggatttat ctacaaacct   2400
gatctaaaaa catgtgaaga cattgatgaa tgcgaatcaa gtccttgcat aatggagtc   2460 tgcaagaaca gcccaggctc ttttatttgt gaatgttctt ctgaaagtac tttggatcca   2520
acaaaaacca tctgcataga aaccatcaag ggcacttgct ggcagactgt cattgatggg   2580
cgatgtgaga tcaacatcaa tggagccacc ttaaagtccc agtgctgctc ctccctcggt   2640
gctgcgtggg aagcccgtg cacccatgc caagttgatc ccatatgtgg taaagggtac   2700
tcaagaatta aggaacaca atgtgaagat atagatgaat gtgaagtgtt cccaggagtg   2760
tgtaaaaatg gcctgtgtgt taacactagg gggtcattca agtgtcagtg tcccagtgga   2820
atgactttgg atgccacagg aaggatctgt cttgatatcc gcctggaaac ctgcttcctg   2880
aggtacgagg acgaggagtg caccctgcct attgctggcc gccaccgcat ggacgcctgc   2940
tgctgctccg tcggggcagc ctggggtact gaggaatgcg aggagtgtcc catgagaaat   3000
actcctgagt acgaggagct gtgtccgaga ggacccggat tgccacaaa agaaattaca   3060 aatggaaagc ctttcttcaa agatatcaat gagtgcaaga tgatacccag cctctgcacc   3120
cacggcaagt gcagaaacac cattggcagc tttaagtgca ggtgtgacag cggctttgct   3180
cttgattctg aagaaggaa ctgcacagac attgacgaat gccgcatatc tcctgacctc   3240
tgtggcagag gccagtgtgt gaacaccct ggggactttg aatgcaagtg tgacgaaggc   3300
tatgaaagtg gattcatgat gatgaagaac tgcatggata ttgatgagtg tcagagagat   3360
cctctcctat gccgaggtgg tgtttgccat aacacagagg gaagttaccg ctgtgaatgc   3420
ccgcctggcc atcagctgtc ccccaacatc tccgcgtgta tcgacatcaa tgaatgtgag   3480
ctgagtgcac acctgtgccc caatggccgt tgcgtgaacc tcatagggaa gtatcagtgt   3540
gcctgcaacc ctggctacca ttcaactccc gataggctat tttgtgttga cattgatgaa   3600
tgcagcataa tgaatggtgg ttgtgaaacc ttctgcacaa actctgaagg cagctatgaa   3660
```

```
tgtagctgtc agccgggatt tgcactaatg cctgaccaga gatcatgcac cgacatcgat    3720
gagtgtgaag ataatcccaa tatctgtgat ggtggtcagt gcacaaatat ccctggagag    3780
tacaggtgct tgtgttatga tggattcatg gcatctgaag acatgaagac ttgtgtagat    3840
gtcaatgagt gtgacctgaa tccaaatatc tgcctaagtg gacctgtgaa aacacgaaa     3900
ggctcattta tctgccactg tgatatgggc tactccggca aaaaggaaa aactggctgt     3960
acagacatca atgaatgtga aattggagca cacaactgtg gcaaacatgc tgtatgtacc    4020
aatacagcag gaagcttcaa atgtagctgc agtcccgggt ggattggaga tggcattaag    4080
tgcactgatc tggacgaatg ttccaatgga acccatatgt gcagccagca tgcagactgc    4140
aagaatacca tgggatctta ccgctgtctg tgcaaggaag atacacagg tgatggcttc     4200
acttgtacag accttgatga gtgctctgag aacctgaatc tctgtggcaa tggccagtgc    4260
ctcaatgcac caggaggata ccgctgtgaa tgcgacatgg gcttcgtgcc cagtgctgac    4320
gggaaagcct gtgaagatat tgatgagtgc tcccttccga acatctgtgt ctttggaact    4380
tgccacaacc tccctggcct gttccgctgt gagtgtgaga taggctacga actggacaga    4440
agcggcggga actgcacaga tgtgaatgaa tgcctggatc caaccacgtg catcagtggg    4500
aactgtgtca cactccagg cagctatatc tgtgactgcc cacctgattt tgaactgaac     4560
ccaactcgag ttggctgtgt tgatacccgc tctggaaatt gctatttgga tattcgacct    4620
cgaggagaca atggagatac agcctgcagc aatgaaattg gagttggtgt ttccaaagct    4680
tcctgctgct gttctctggg taaagcctgg ggtactcctt gtgagatgtg tcctgctgtg    4740
aacacatccg agtacaaaat tctttgtcct ggagggaag gtttccgacc aaatcctatc    4800
accgttatat tggaagatat tgatgagtgc caggagctac cagggctgtg ccaaggagga    4860
aaatgtatca acacctttgg gagtttccag tgccgctgtc caaccggcta ctacctgaat    4920
gaagatacac gagtgtgtga tgatgtgaat aatgtgaga ctcctggaat ctgtggtcca     4980
gggacatgtt acaacaccgt tggcaactac acctgtatct gtcctccaga ctacatgcaa    5040
gtgaatgggg gaaataattg catggatatg agaagaagtt tgtgctacag aaactactat    5100
gctgacaacc agacctgtga tggagaattg ttattcaaca tgaccaagaa gatgtgctgc    5160
tgttcctaca acattggccg ggcgtggaac aagccctgtg aacagtgtcc catcccaagt    5220
acagatgagt ttgctacact ctgtggaagt caaaggccag gctttgtcat cgacatttat    5280
accggtttac ccgttgatat tgatgagtgc cgggagatcc aggggtctg tgaaaatgga     5340
gtgtgtatca acatggttgg cagcttccga tgtgaatgtc cagtgggatt cttctataat    5400
gacaagttgt tggtttgtga agatattgac gagtgtcaga acggcccagt gtgccagcgc    5460
aacgccgaat gcatcaacac tgcaggcagc taccgctgtg actgtaagcc cggctaccgc    5520
ttcacctcca caggacagtg caatgatcgt aatgaatgtc aagaaatccc caatatatgc    5580
agtcatgggc agtgcattga cacagttgga agctttatt gccttttgcca cactggtttt    5640
aaaacaaatg atgaccaaac catgtgcttg gacataaatg aatgtgaaag atgcctgt     5700
gggaatggaa cttgccggaa cacaattggt tccttcaact ccgctgcaa tcatggtttc    5760
atcctttctc acaacaatga ctgtatagat gttgatgaat gtcaagtgg aaatgggaat    5820
cttttgcagaa atggccaatg cattaataca gtgggtctt tccagtgcca gtgcaatgaa    5880
ggctatgagg tggctccaga tgggaggacc tgtgtggata tcaatgaatg tcttctagaa    5940
cccagaaaat gtgcaccagg tacctgtcaa aacttggatg ggtcctacag atgcatttgc    6000
ccacctggat acagtcttca aaatgagaag tgtgaagata ttgatgagtg tgtcgaagag    6060
```

```
ccagaaattt gtgccctggg cacatgcagt aacactgaag gcagcttcaa atgtctgtgt    6120
ccagaagggt tttccttgtc ctccagtgga agaaggtgcc aagatttgcg aatgagctac    6180
tgttatgcga agtttgaagg aggaaagtgt tcatcaccca aatccagaaa tcactccaag    6240
caggaatgct gctgtgcctt gaagggagaa ggctggggag accctgcga gctctgcccc    6300 acggaacctg atgaggcctt ccgccagata tgtccttatg aagtgggat catcgtggga    6360 cctgatgatt cagcagttga tatggacgaa tgcaaagaac ccgatgtctg taaacatgga    6420
cagtgcatca atacagatgg ttcctatcgc tgcgagtgtc cctttggtta tattctagca    6480
gggaatgaat gtgtagatac tgatgaatgt tctgttggca atccttgtgg aaatggaacc    6540
tgcaagaatg tgattggagg ttttgaatgc acctgcgagg agggatttga gcccggtcca    6600
atgatgacat gtgaagatat aaatgaatgt gcccagaatc ctctgctctg tgccttccga    6660
tgtgtgaaca cttatgggtc atatgaatgc aaatgtcccg tgggatatgt gctcagagaa    6720
gaccgtagga tgtgcaaaga tgaggatgag tgtgaagagg gaaaacatga ctgtactgaa    6780
aaacaaatgg aatgcaagaa cctcattggc acatatatgt gcatctgtgg acccgggtat    6840
cagcggagac ctgatggaga aggctgtgta gatgagaatg aatgtcagac gaagccaggg    6900
atctgtgaga atgggcgctg cctcaacacc cgtgggagct acacctgtga gtgtaatgat    6960
gggtttaccg ccagccccaa ccaggacgag tgccttgaca atcgggaagg gtactgcttc    7020
acagaggtgc tacaaaacat gtgtcagatc ggctccagca acaggaaccc cgtcaccaaa    7080
tcggaatgct gctgtgacgg agggagaggc tggggtcccc actgtgagat ctgcccttc    7140 caggggactg tggcttttcaa gaaactctgt ccccatggcc gaggattcat gaccaatgga    7200
gcagatatcg atgaatgcaa ggttattcac gatgtttgcc gaaatgggga atgtgtcaat    7260
gacagaggat catatcattg catttgtaaa actgggtaca ctccagatat aactgggact    7320
tcctgtgtag atctgaacga gtgcaaccag gctcccaaac cctgcaattt tatctgcaaa    7380
aacacagaag ggagttacca gtgttcatgc ccgaaaggct acattctgca agaggatgga    7440
aggagctgca aagatcttga tgagtgtgca accaagcaac acaactgcca gttcctatgt    7500
gttaacacca ttggcggctt cacatgcaaa tgtcctcccg gatttaccca acaccatacg    7560
tcctgcattg ataacaatga atgcacctct gacatcaatc tgtgcgggtc taagggcatt    7620
tgccagaaca ctcctggaag cttcacctgt gaatgccagc ggggattctc acttgatcag    7680
accggctcca gctgtgaaga cgtggacgag tgtgagggta accaccgctg ccagcatggc    7740
tgccagaaca tcattggggg ctacaggtgc agctgccccc agggctacct ccagcactac    7800
cagtggaacc agtgtgttga tgaaaacgaa tgcctcagcg ctcacatctg cggaggagcc    7860
tcctgtcaca cacccctggg gagctacaag tgcatgtgtc ccgccggctt ccagtatgaa    7920
cagttcagtg gaggatgcca agacatcaat gaatgtggct ctgcgcaggc ccctgcagc    7980 tatgctgtt ccaataccga gggcggttac ctgtgtggct gtccacctgg ttacttccgc    8040
ataggccaag ggcactgtgt ttctggaatg ggcatgggcc gaggaaaccc agagccacct    8100
gtcagtggtg aaatggatga caattcactc tccccagagg cttgttacga gtgtaagatc    8160
aatggctacc ccaaacgggg caggaaacgg agaagcacaa acgaaactga tgcctccaat    8220
atcgaggatc agtctgagac agaagccaat gtgagtcttg caagttggga tgttgagaag    8280
acagccatct ttgctttcaa tatttcccac gtcagtaaca aggttcgaat cctagaactc    8340
cttccagctc ttacaactct gacgaatcac aaacagatact tgatcgaatc tggaaatgaa    8400
```

| | |
|---|---:|
| gatggcttct ttaaaatcaa ccaaaaggaa gggatcagct acctccactt cacaaagaag | 8460 |
| aagccagtgg ctggaaccta ttcattacaa atcagtagta ctccacttta taaaaagaaa | 8520 |
| gaacttaacc aactagaaga caaatatgac aaagactacc tcagtggtga actgggtgat | 8580 |
| aatctgaaga tgaaaatcca ggttttgctt cattaa | 8616 |

<210> SEQ ID NO 20
<211> LENGTH: 8622
<212> TYPE: DNA
<213> ORGANISM: Mus musculus

<400> SEQUENCE: 20

| | |
|---|---:|
| atgcggcgag gagggctgct ggaggtcgcg ctggcgttcg ccctgctcct cgagtcctac | 60 |
| acgagccatg gggcggacgc caatttggag gctgggagcc tgaaggagac cagagccaat | 120 |
| cgggccaaga gaagaggcgg cggaggacac gatgcgctga aaggacccaa tgtctgtgga | 180 |
| tcacgttata atgcatactg ttgtcctgga tggaaaacct acctggtgg aaatcagtgt | 240 |
| attgttccca tttgccggca ttcctgtggg gatggattc gctcgaggcc aaatatgtgc | 300 |
| acttgcccgt ctggtcagat atctccttcc tgtggctcca gatccatcca acactgcagc | 360 |
| atccgctgta tgaatggggg cagctgcagc gatgaccact gtctgtgcca gaaagggtac | 420 |
| atcggcactc actgtggaca gcctgtctgt gaaagtggct gtctcaacgg agggaggtgt | 480 |
| gtggccccaa atcggtgtgc ttgcacgtac ggctttactg accccagtg tgaaagagat | 540 |
| tacagaacag gcccatgttt tactgtggta agcaaccaga tgtgccaggg acagctcagc | 600 |
| gggattgtct gcaccaaaac actttgctgt gccaccgtgg gccgagcctg ggccacccc | 660 |
| tgtgagatgt gtcctgccca gcctcacccc tgccgccgcg gcttcattcc aacatccgc | 720 |
| actggagctt gtcaagatgt ggatgaatgt caggccatcc agggatgtg tcaaggagga | 780 |
| aattgcatta ataccgttgg atcttttgag tgcaaatgcc ctgctggaca caaatttaat | 840 |
| gaagtgtcac aaaaatgtga agatattgac gagtgcagca ccattcctgg agtctgcgat | 900 |
| ggcggggaat gtacaaacac tgtcagcagc tacttctgca aatgtccccc tggttttac | 960 |
| acctctcctg atggcaccag atgcgtagat gttcgccctg ttactgcta cacagctctg | 1020 |
| gcaaacgggc gctgctctaa ccagctgcca cagtccataa ccaaaatgca gtgctgttgc | 1080 |
| gatcttggcc ggtgctggtc tcagggggtt actgttgctc ccgagatgtg tcccatcagg | 1140 |
| tcaactgagg atttcaacaa gctgtgctct gtccctctgg taattcccgg agaccagaa | 1200 |
| tatcctcccc cacccattgg ccccttcct ccagttcagc ccgttcctcc tggctatcct | 1260 |
| cctgggcctg tgattccagc ccctcggcca ccgccagaat atccatatcc atctccgtct | 1320 |
| cgggaaccac caagggtgct gccttttcaac gttactgact actgtcaact ggtccgctat | 1380 |
| ctctgtcaaa atgggcgctg cattccaact cccggtagct accgctgcga gtgcaacaag | 1440 |
| ggcttccagc tggatatccg tggcgaatgc atcgacgtgg atgagtgtga agaacccca | 1500 |
| tgcactggtg gcgagtgcat caacaaccag ggctcctaca cctgtcactg cagagctggc | 1560 |
| taccagagca cactcaccag aactgagtgc agagacatag atgagtgtct tcagaatggc | 1620 |
| cggatctgca acaatggtcg ctgtatcaac acagacggca gcttccactg cgtatgcaat | 1680 |
| gcgggctttc atgtcacgcg ggacggaaag aactgtgaag atatggatga gtgcagcatc | 1740 |
| cgaaacatgt gcctaaacgg aatgtgtatt aatgaagatg gcagtttcaa gtgtatttgc | 1800 |
| aaacctgggt tccaactggc atcagatggc cgctactgca aagatatcaa tgagtgtgag | 1860 |
| acacctggga tctgcatgaa cggacgctgt gtgaacacgg atggctccta cagatgcgaa | 1920 |

```
tgcttcccccg gattggctgt gggtctagac ggacgtgtgt gtgttgacac acacatgcgg   1980
agcacatgct atggaggata caggagaggc cagtgcgtga agccgttgtt tggtgctgtt   2040
accaaatcgg aatgctgttg tgccagcact gagtatgcct ttggggaacc ctgccagccg   2100
tgtcctgcac agaattcagc ggaatatcag gcactctgca gcagtggacc gggaatgaca   2160
tcagcaggca ctgatataaa cgaatgtgca ttagatcctg atatttgccc aaatggaatt   2220
tgtgaaaatc tccgtgggac ctacaaatgt atatgcaact cgggatatga agtagacata   2280
actgggaaaa actgtgtcga tattaatgag tgtgtgctga acagtctact ttgtgacaat   2340
ggacaatgtc gaaacacacc tggaagtttt gtctgcacct gccccaaagg atttgtgtac   2400
aaacctgacc taaaaacctg tgaagacatt gatgaatgtg aatcgagtcc ttgcattaat   2460
ggagtctgca gaacagccc tggctccttc atttgtgaat gttctcctga aagtactctg   2520
gacccaacaa aaccatctg catagaaacc atcaagggca cttgctggca gactgtcatc   2580
gacgggcgct gtgagatcaa catcaacgga gccaccttga agtccgagtg ctgctcctcc   2640
cttggtgctg cgtgggggag cccgtgcacc atctgtcaac ttgatcccat ttgtggtaaa   2700
gggttctcaa gaattaaagg cacgcaatgt gaagatatca atgagtgtga agtgttcccg   2760
ggagtatgca agaacggcct gtgtgtcaac tccagggtt cattcaagtg cgagtgtccc   2820
aatggaatga ctttggatgc tacaggaaga atctgtcttg acatccgcct ggagacctgc   2880
ttcctcaagt atgacgatga agagtgcacc ttgcccatcg ctggccgcca ccgaatggat   2940
gcctgctgct gctctgttgg ggcagcctgg ggaacggaag agtgtgagga gtgtccattg   3000
agaaacagcc gggagtatga ggaactctgt cccccgaggac ctgggtttgc cacaaaagac   3060
attacaaatg ggaaaccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
tgtgagctga gtgcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac ctgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat ggagacggc   4080 attaagtgca cagatctgga tgaatgctct aatggaaccc acatgtgcag ccaacacgcg   4140
gactgcaaga acaccatggg gtcatatcgc tgtctctgta aggatggcta cagggggat   4200 ggcttcacct gtacagacct cgacgagtgc tccgagaacc tgaacctctg tggcaatggc   4260
```

```
cagtgcctca acgcccctgg cgggtaccgc tgtgaatgcg acatgggctt cgtgcccagt    4320
gctgacggga aggcctgtga agatatcgat gagtgctccc ttccaaacat ctgtgtcttt    4380
ggaacttgcc acaacctccc gggcctcttc cgttgcgagt gtgagattgg ctatgaactg    4440
gaccgaagtg gtggaaactg cacagatgtt aatgagtgtc tggatcccac cacctgcatc    4500
agtggaaact gtgtcaacac tcccggtagt tacacatgcg attgtcctcc ggattttgag    4560
ctgaatccaa ctcgtgtcgg ctgtgtcgat actcgctctg gaaactgcta tctggatatc    4620
cgaccccggg gagacaatgg agatacagcc tgcagcaatg aaattggagt tggtgtctct    4680
aaggcttcct gctgttgttc actgggtaaa gcttggggaa ccccatgtga gctgtgtcct    4740
tctgtgaaca catctgagta taaaattctt tgccctggag agaaggtttt tcgtccaaat    4800
cccatcaccg ttatattgga agacatcgat gagtgccagg agcttccagg gctgtgccaa    4860 gggggggaagt gcatcaatac ctttggcagc ttccagtgtc gctgtccaac tggttactac    4920
ctgaatgaag acactcgagt gtgtgatgat gtgaacgaat gtgagactcc tggaatctgt    4980
ggtccgggga cctgttacaa caccgttggc aactatacct gcatttgtcc tccagactac    5040
atgcaagtga acgggggaaa taattgcatg gacatgagaa gaagtctatg ctacagaaac    5100
tattacgctg acaaccagac ctgcgatgga gaactcctgt tcaacatgac caagaagatg    5160
tgctgttgct cctacaacat cggcagagcc tggaacaaac cctgtgaaca gtgccccatc    5220
ccaagcacag atgagtttgc taccctctgt gggagccaga ggcccggctt cgtgattgac    5280
atttatacgg gtttacccgt ggatattgat gaatgccggg agatccctgg ggtctgtgaa    5340
aatgagtgtg tgcatcaacat ggttggcagc ttccggtgtg agtgtcccgt gggattcttc    5400
tataacgaca agttactggt ttgtgaagat atcgacgagt gtcagaatgg ccctgtgtgc    5460
cagcgaaatg cggaatgcat caacactgca ggcagctacc gctgtgactg taagcccggc    5520
taccgcctta cctccacagg tcaatgcaac gatcgaaacg agtgccaaga atcccgaac    5580 atatgcagtc atggccagtg catcgacacc gtggaagct tctactgcct ttgtcacact    5640
ggcttcaaaa caaatgtgga tcagaccatg tgcttagaca taaatgagtg tgagagagac    5700
gcctgtggga acgggacttg cagaaacacg attggctcct tcaactgtcg ctgtaaccat    5760
ggcttcatac tgtctcacaa caatgactgc atagatgttg atgagtgtgc aactggaaac    5820
gggaaccttt gcagaaatgg ccagtgtgtc aataccgtgg gctccttcta gtgcaggtgc    5880
aatgaaggct atgaggtggc tccggacggc aggacctgtg tggatatcaa cgagtgtgtt    5940
ctggatcctg ggaaatgtgc acctggaacc tgtcagaacc tggatggctc ctacagatgc    6000
atttgcccgc ctgggtatag tctacagaat gacaagtgtg aagatattga tgagtgtgtt    6060
gaagagccag aaatctgtgc cttggggacc tgcagcaaca ctgagggtag cttcaaatgt    6120
ctgtgtccag aggggttctc cctgtcctcc actggaagaa ggtgccaaga tttgcgaatg    6180
agctactgct atgcgaagtt tgaaggtggg aagtgttcat cacccaaatc cagaaaccat    6240
tccaagcagg agtgctgctg tgctttgaag ggagaaggct ggggagatcc ttgtgagttg    6300
tgccccactg agccagatga ggcttccgc cagatctgcc cctttggaag tgggatcatt    6360
gtgggccctg atgactcagc agttgatatg gacgaatgca aagaacctga tgtctgtaga    6420
catgggcagt gcattaacac agacggctcc tatcgatgcg agtgtccttt tggttatatt    6480
ctggaaggga tgagtgtgt ggataccgat gaatgctctg tgggcaatcc ttgtggaaat    6540
gggacctgca aagaatgtgat tggaggtttt gaatgtacct gtgaggaggg gttcgagcct    6600
ggcccaatga tgacttgtga agatatatat gaatgtgccc agaatcctct gctctgcgcc    6660
```

| | |
|---|---|
| ttccgctgtg taaatacccta cgggtcctat gaatgcaaat gccctgttgg atacgttctc | 6720 |
| cgagaagaca ggaggatgtg taaagatgag gatgagtgtg cagagggaaa acacgactgt | 6780 |
| actgagaagc aaatggagtg taagaacctc attggtacct acatgtgcat ctgcggccct | 6840 |
| gggtaccagc gcagacccga tggagagggc tgcatagatg agaatgagtg tcagaccaag | 6900 |
| cccgggatct gtgagaatgg gcgttgcctc aacaccctgg gtagctacac ttgtgagtgt | 6960 |
| aacgatggct tcacagccag ccccactcag gatgagtgct tggacaaccg ggaagggtac | 7020 |
| tgcttttcgg aggtcttgca aaacatgtgc cagattggct caagcaacag gaaccccgtc | 7080 |
| accaagtccg agtgctgctg tgatggaggg agaggctggg acccccactg tgagatctgc | 7140 |
| cctttcgagg gcacagtggc ttacaagaag ctctgtcccc acggccgagg attcatgacc | 7200 |
| aacggagcag atattgatga gtgcaaggtt attcatgatg tttgccgaaa tgggagtgt | 7260 |
| gtcaacgaca gagggtccta tcactgcatc tgtaaaactg gctacactcc ggatataaca | 7320 |
| gggaccgcct gtagatctga atgaatgc aaccaggctc ccaaaccctg caatttata | 7380 |
| tgcaaaaaca cagaagggag ttaccagtgt tcctgcccga agggctacat tctgcaagag | 7440 |
| gatgaagga gctgcaaaga tcttgacgag tgtgcaacca agcagcataa ctgtcagttc | 7500 |
| ctgtgtgtta acaccatcgg tggcttcaca tgcaaatgcc ctcctgggtt tacccagcat | 7560 |
| cacactgcct gcattgataa caatgagtgc acgtctgata tcaacctgtg tgggtccaag | 7620 |
| ggtgtttgcc agaacactcc aggaagcttc acctgtgaat gccaacgggg gttctcactc | 7680 |
| gatcagagtg gtgccagctg tgaagatgtg gacgagtgtg agggtaacca ccgctgtcaa | 7740 |
| catggctgcc agaacatcat cggaggctat aggtgtagct gccccaggg ctacctccag | 7800 |
| cactaccaat ggaaccagtg tgtagatgaa aacgagtgcc tgagtgcaca tgtctgtgga | 7860 |
| ggagcctcct gccacaacac cctggggagt tacaagtgca tgtgtcccac cggcttccag | 7920 |
| tacgaacagt tcagtggagg ctgccaagac atcaatgagt gtggctcatc ccaggccccc | 7980 |
| tgcagttacg gttgctctaa tactgagggt ggctacctgt gtggctgtcc accaggatac | 8040 |
| ttccggatag gccaagggca ttgtgttct ggaatgggca tgggccgagg cggcccagag | 8100 |
| ccacctgcca gcagcgagat ggacgacaac tcactgtccc cagaggcctg ctatgagtgt | 8160 |
| aagatcaacg gctacccaaa acgaggccgg aaacggagaa gcacgaacga aacggatgcc | 8220 |
| tccgacatcc aggacgggtc tgagatggaa gccaacgtga gcctcgccag ctgggatgtg | 8280 |
| gagaagccgg ctagctttgc tttcaatatt tcccatgtca ataacaaggt ccgaatccta | 8340 |
| gagctcctgc cggccctcac aactctgatg aaccacaaca gatacttgat tgaatctgga | 8400 |
| aatgaagatg gcttctttaa aatcaaccag aaagaagggg tcagctacct ccacttcacg | 8460 |
| aagaagaagc cggtggctgg gacctactcc ttacaaatca gcagcacccc actttataaa | 8520 |
| aagaaagaac ttaaccagtt agaagacaga tatgacaaag actacctcag tggtgaactg | 8580 |
| ggcgataacc tgaagatgaa aattcagatc ttgctgcatt aa | 8622 |

<210> SEQ ID NO 21
<211> LENGTH: 8623
<212> TYPE: DNA
<213> ORGANISM: Artificial Sequence
<220> FEATURE:
<223> OTHER INFORMATION: Synthetic

<400> SEQUENCE: 21
atgcggcgag gagggctgct ggaggtcgcg ctggcgttcg ccctgctcct cgagtcctac      60

```
acgagccatg gggcggacgc caatttggag gctgggagcc tgaaggagac cagagccaat      120
cgggccaaga gaagaggcgg cggaggacac gatgcgctga aaggacccaa tgtctgtgga      180
tcacgttata atgcatactg ttgtcctgga tggaaaacct tacctggtgg aaatcagtgt      240
attgttccca tttgccggca ttcctgtggg gatggattct gctcgaggcc aaatatgtgc      300
acttgcccgt ctggtcagat atctccttcc tgtggctcca gatccatcca acactgcagc      360
atccgctgta tgaatggggg cagctgcagc gatgaccact gtctgtgcca gaaagggtac      420
atcggcactc actgtggaca gcctgtctgt gaaagtggct gtctcaacgg agggaggtgt      480
gtggccccaa atcggtgtgc ttgcacgtac ggctttactg gaccccagtg tgaaagagat      540
tacagaacag gcccatgttt tactgtggta agcaaccaga tgtgccaggg acagctcagc      600
gggattgtct gcaccaaaac actttgctgt gccaccgtgg gccgagcctg ggccacccc      660 tgtgagatgt gtcctgccca gcctcacccc tgccgccgcg gcttcattcc caacatccgc      720
actggagctt gtcaagatgt ggatgaatgt caggccatcc cagggatgtg tcaaggagga      780
aattgcatta ataccgttgg atcttttgag tgcaaatgcc ctgctggaca caaatttaat      840
gaagtgtcac aaaaatgtga agatattgac gagtgcagca ccattcctgg agtctgcgat      900
ggcggggaat gtacaaacac tgtcagcagc tacttctgca aatgtccccc tggttttac      960 acctctcctg atggcaccag atgcgtagat gttcgccctg ttactgcta cacagctctg     1020 gcaaacgggc gctgctctaa ccagctgcca cagtccataa ccaaaatgca gtgctgttgc     1080
gatcttggcc ggtgctggtc tccagggggtt actgttgctc ccgagatgtg tcccatcagg     1140
tcaactgagg atttcaacaa gctgtgctct gtccctctgg taattcccgg gagaccagaa     1200
tatcctcccc cacccattgg ccccctttcct ccagttcagc ccgttcctcc tggctatcct     1260
cctgggcctg tgattccagc ccctcggcca ccgccagaat atccatatcc atctccgtct     1320
cgggaaccac caagggtgct gcctttcaac gttactgact actgtcaact ggtccgctat     1380
ctctgtcaaa atgggcgctg cattccaact cccggtagct accgctgcga gtgcaacaag     1440
ggcttccagc tggatatccg tggcgaatgc atcgacgtgg atgagtgtga agaacccca     1500 tgcactggtg gcgagtgcat caacaaccag ggctcctaca cctgtcactg cagagctggc     1560
taccagagca cactcaccag aactgagtgc agagacatag atgagtgtct tcagaatggc     1620
cggatctgca acaatggtcg ctgtatcaac acagacggca gcttccactg cgtatgcaat     1680
gcgggctttc atgtcacgcg ggacggaaag aactgtgaag atatggatga gtgcagcatc     1740
cgaaacatgt gcctaaacgg aatgtgtatt aatgaagatg gcagtttcaa gtgtatttgc     1800
aaacctgggt tccaactggc atcagatggc cgctactgca aagatatcaa tgagtgtgag     1860
acacctggga tctgcatgaa cggacgctgt gtgaacacgg atggctccta cagatgcgaa     1920
tgcttccccg gattggctgt gggtctagac ggacgtgtgt gtgttgacac acacatgcgg     1980
agcacatgct atgaggata caggagaggc cagtgcgtga agccgttgtt tggtgctgtt     2040
accaaatcgg aatgctgttg tgccagcact gagtatgcct ttggggaacc ctgccagccg     2100
tgtcctgcac agaattcagc ggaatatcag gcactctgca gcagtggacc gggaatgaca     2160
tcagcaggca ctgatataaa cgaatgtgca ttagatcctg atatttgccc aaatggaatt     2220
tgtgaaaatc tccgtgggac ctacaaatgt atatgcaact cgggatatga agtagacata     2280
actgggaaaa actgtgtcga tattaatgag tgtgtgctga acagtctact ttgtgacaat     2340
ggacaatgtc gaaacacacc tggaagtttt gtctgcacct gccccaaagg atttgtgtac     2400
aaacctgacc taaaaacctg tgaagacatt gatgaatgtg aatcgagtcc ttgcattaat     2460
```

```
ggagtctgca agaacagccc tggctccttc atttgtgaat gttctcctga aagtactctg   2520
gacccaacaa aaaccatctg catagaaacc atcaagggca cttgctggca gactgtcatc   2580
gacgggcgct gtgagatcaa catcaacgga gccaccttga agtccgagtg ctgctcctcc   2640
cttggtgctg cgtgggggag cccgtgcacc atctgtcaac ttgatcccat ttgtggtaaa   2700
gggttctcaa gaattaaagg cacgcaatgt gaagatatca atgagtgtga agtgttcccg   2760
ggagtatgca agaacggcct gtgtgtcaac tccaggggtt cattcaagtg cgagtgtccc   2820
aatggaatga ctttggatgc tacaggaaga atctgtcttg acatccgcct ggagacctgc   2880
ttcctcaagt atgacgatga agagtgcacc ttgcccatcg ctggccgcca ccgaatggat   2940
gcctgctgct gctctgttgg ggcagcctgg ggaacggaag agtgtgagga gtgtccattg   3000
agaaacagcc gggagtatga ggaactctgt ccccgaggac ctgggtttgc cacaaaagac   3060
attacaaatg ggaaaccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
tgtgagctga gtcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac tgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat tggagacggc   4080
attaagtgca cagatctgga tgaatgctct aatggaaccc acatgtgcag ccaacacgcg   4140
gactgcaaga acaccatggg gtcatatcgc tgtctctgta aggatggcta cagggggat   4200
ggcttcacct gtacagacct cgacgagtgc tccgagaacc tgaacctctg tggcaatggc   4260
cagtgcctca cgcccctggc gggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtggaaactg cacagatgtt aatgagtgtc tggatcccac cacctgcatc   4500
agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag gagaaggttt tcgtccaaat   4800
```

```
cccatcaccg ttatattgga agacatcgat gagtgccagg agcttccagg gctgtgccaa    4860
gggggggaagt gcatcaatac ctttggcagc ttccagtgtc gctgtccaac tggttactac    4920
ctgaatgaag acactcgagt gtgtgatgat gtgaacgaat gtgagactcc tggaatctgt    4980
ggtccgggga cctgttacaa caccgttggc aactatacct gcatttgtcc tccagactac    5040
atgcaagtga acgggggaaa taattgcatg gacatgagaa gaagtctatg ctacagaaac    5100
tattacgctg acaaccagac ctgcgatgga gaactcctgt tcaacatgac caagaagatg    5160
tgctgttgct cctacaacat cggcagagcc tggaacaaac cctgtgaaca gtgccccatc    5220
ccaagcacag atgagtttgc taccctctgt gggagccaga ggcccggctt cgtgattgac    5280
atttatacgg gtttacccgt ggatattgat gaatgccggg agatccctgg ggtctgtgaa    5340
aatggagtgt gcatcaacat ggttggcagc ttcggtgtg agtgtcccgt gggattcttc    5400
tataacgaca agttactggt ttgtgaagat atcgacgagt gtcagaatgg ccctgtgtgc    5460
cagcgaaatg cggaatgcat caacactgca ggcagctacc gctgtgactg taagcccggc    5520
taccgcctta cctccacagg tcaatgcaac gatcgaaacg agtgccaaga atcccgaac    5580
atatgcagtc atggccagtg catcgacacc gtgggaagct tctactgcct ttgtcacact    5640
ggcttcaaaa caaatgtgga tcagaccatg tgcttagaca taaatgagtg tgagagagac    5700
gcctgtggga acgggacttg cagaaacacg attggctcct tcaactgtcg ctgtaaccat    5760
ggcttcatac tgtctcacaa caatgactgc atagatgttg atgagtgtgc aactggaaac    5820
gggaaccttt gcagaaatgg ccagtgtgtc aataccgtgg gctcctttca gtgcaggtgc    5880
aatgaaggct atgaggtggc tccggacggc aggacctgtg tggatatcaa cgagtgtgtt    5940
ctggatcctg ggaaatgtgc acctggaacc tgtcagaacc tggatggctc ctacagatgc    6000
atttgcccgc ctgggtatag tctacagaat gacaagtgtg aagatattga tgagtgtgtt    6060
gaagagccag aaatctgtgc cttggggacc tgcagcaaca ctgagggtag cttcaaatgt    6120
ctgtgtccag aggggttctc cctgtcctcc actggaagaa ggtgccaaga tttgcgaatg    6180
agctactgct atgcgaagtt tgaaggtggg aagtgttcat cacccaaatc cagaaaccat    6240
tccaagcagg agtgctgctg tgcttttgaag ggagaaggct ggggagatcc ttgtgagttg    6300
tgccccactg agccagatga ggcttttccgc cagatctgcc cctttggaag tgggatcatt    6360
gtgggccctg atgactcagc agttgatatg gacgaatgca aagaacctga tgtctgtaga    6420
catgggcagt gcattaacac agacggctcc tatcgatgcg agtgtccttt tggttatatt    6480
ctggaaggga atgagtgtgt ggataccgat gaatgctctg tgggcaatcc ttgtggaaat    6540
gggacctgca agaatgtgat tggaggtttt gaatgtacct gtgaggaggg gttcgagcct    6600
ggcccaatga tgacttgtga agatatataaat gaatgtgccc agaatcctct gctctgcgcc    6660
ttccgctgtg taaataccta cgggtcctat gaatgcaaat gccctgttgg atacgttctc    6720
cgagaagaca ggaggatgtg taaagatgag gatgagtgtg cagagggaaa acacgactgt    6780
actgagaagc aaatggagtg taagaacctc attggtacct acatgtgcat ctgcggccct    6840
gggtaccagc gcagacccga tggagagggc tgcatagatg agaatgagtg tcagaccaag    6900
cccgggatct gtgagaatgg cgttgcctc aacaccctgg gtagctacac ttgtgagtgt    6960
aacgatggct tcacagccag ccccactcag gatgagtgct tggacaaccg ggaagggtac    7020
tgcttttcgg aggtcttgca aaacatgtgc cagattggct caagcaacag gaaccccgtc    7080
accaagtccg agtgctgctg tgatggaggg agaggctggg gacccactg tgagatctgc    7140
cctttcgagg gcacagtggc ttacaagaag ctctgtccc acggccgagg attcatgacc    7200
```

```
aacggagcag atattgatga gtgcaaggtt attcatgatg tttgccgaaa tggggagtgt    7260
gtcaacgaca gagggtccta tcactgcatc tgtaaaactg gctacactcc ggatataaca    7320
gggaccgcct gtgtagatct gaatgaatgc aaccaggctc ccaaaccctg caattttata    7380
tgcaaaaaca cagaagggag ttaccagtgt tcctgcccga agggctacat tctgcaagag    7440
gatggaagga gctgcaaaga tcttgacgag tgtgcaacca agcagcataa ctgtcagttc    7500
ctgtgtgtta acaccatcgg tggcttcaca tgcaaatgcc ctcctgggtt tacccagcat    7560
cacactgcct gcattgataa caatgagtgc acgtctgata tcaacctgtg tgggtccaag    7620
ggtgtttgcc agaacactcc aggaagcttc acctgtgaat gccacgggg gttctcactc    7680 gatcagagtg gtgccagctg tgaagatgtg gacgagtgtg agggtaacca ccgctgtcaa    7740
catggctgcc agaacatcat cggaggctat aggtgtagct gccccagg ctacctccag    7800 cactaccaat ggaaccagtg tgtagatgaa acgagtgcc tgagtgcaca tgtctgtgga    7860
ggagcctcct gccacaacac cctggggagt tacaagtgca tgtgtcccac cggcttccag    7920
tacgaacagt tcagtggagg ctgccaagac atcaatgagt gtggctcatc ccaggccccc    7980
tgcagttacg gttgctctaa tactgagggt ggctacctgt gtggctgtcc accaggatac    8040
ttccggatag gccaagggca ttgtgttcct ggaatgggca tgggccgagg cggcccagag    8100
ccacctgcca gcagcgagat ggacgacaac tcactgtccc cagaggcctg ctatgagtgt    8160
aagatcaacg gctacccaaa acgaggccgg aaacggagaa gcacgaacga aaactgatgc    8220
ctccgacatc caggacgggt ctgagatgga agccaacgtg agcctcgcca gctgggatgt    8280
ggagaagccg gctagctttg ctttcaatat ttcccatgtc aataacaagg tccgaatcct    8340
agagctcctg ccggccctca caactctgat gaaccacaac agatacttga ttgaatctgg    8400
aaatgaagat ggcttcttta aaatcaacca gaaagaaggg gtcagctacc tccacttcac    8460
gaagaagaag ccggtggctg ggacctactc cttacaaatc agcagcaccc cactttataa    8520
aaagaaagaa cttaaccagt tagaagacag atatgacaaa gactacctca gtggtgaact    8580
gggcgataac ctgaagatga aaattcagat cttgctgcat taa                      8623
```

<210> SEQ ID NO 22
<211> LENGTH: 8647
<212> TYPE: DNA
<213> ORGANISM: Artificial Sequence
<220> FEATURE:
<223> OTHER INFORMATION: Synthetic

<400> SEQUENCE: 22

```
atgcggcgag gagggctgct ggaggtcgcg ctggcgttcg ccctgctcct cgagtcctac      60
acgagccatg gggcggacgc caatttggag gctgggagcc tgaaggagac cagagccaat    120
cgggccaaga gaagaggcgg cggaggacac gatgcgctga aggacccaa tgtctgtgga     180 tcacgttata atgcatactg ttgtcctgga tggaaaacct tacctggtgg aaatcagtgt    240
attgttccca tttgccggca ttcctgtggg gatggattct gctcgaggcc aaatatgtgc    300
acttgcccgt ctggtcagat atctccttcc tgtggctcca gatccatcca acactgcagc    360
atccgctgta tgaatggggg cagctgcagc gatgaccact gtctgtgcca gaaagggtac    420
atcggcactc actgtggaca gcctgtctgt gaaagtggct gtctcaacgg agggaggtgt    480
gtggccccaa atcggtgtgc ttgcacgtac ggctttactg gaccccagtg tgaaagagat    540
tacagaacag gcccatgttt tactgtggta agcaaccaga tgtgccaggg acagctcagc    600
```

```
gggattgtct gcaccaaaac actttgctgt gccaccgtgg gccgagcctg gggccacccc      660
tgtgagatgt gtcctgccca gcctcacccc tgccgccgcg gcttcattcc caacatccgc      720
actggagctt gtcaagatgt ggatgaatgt caggccatcc cagggatgtg tcaaggagga      780
aattgcatta ataccgttgg atcttttgag tgcaaatgcc ctgctggaca caaatttaat      840
gaagtgtcac aaaaatgtga agatattgac gagtgcagca ccattcctgg agtctgcgat      900
ggcggggaat gtacaaacac tgtcagcagc tacttctgca aatgtccccc tggtttttac      960
acctctcctg atggcaccag atgcgtagat gttcgccctg gttactgcta cacagctctg     1020
gcaaacgggc gctgctctaa ccagctgcca cagtccataa ccaaaatgca gtgctgttgc     1080
gatcttggcc ggtgctggtc tccaggggtt actgttgctc ccgagatgtg tcccatcagg     1140
tcaactgagg atttcaacaa gctgtgctct gtccctctgg taattcccgg agaccagaa      1200 tatcctcccc cacccattgg ccccttcct ccagttcagc ccgttcctcc tggctatcct      1260
cctgggcctg tgattccagc ccctcggcca ccgccagaat atccatatcc atctccgtct     1320
cgggaaccac caagggtgct gccttcaac gttactgact actgtcaact ggtccgctat      1380
ctctgtcaaa atgggcgctg cattccaact cccgtagct accgctgcga gtgcaacaag      1440
ggcttccagc tggatatccg tggcgaatgc atcgacgtgg atgagtgtga agaaccca      1500 tgcactggtg gcgagtgcat caacaaccag ggctcctaca cctgtcactg cagagctggc     1560
taccagagca cactcaccag aactgagtgc agagacatag atgagtgtct tcagaatggc     1620
cggatctgca caatggtcg ctgtatcaac acagacggca gcttccactg cgtatgcaat      1680
gcgggctttc atgtcacgcg ggacggaaag aactgtgaag atatggatga gtgcagcatc     1740
cgaaacatgt gcctaaacgg aatgtgtatt aatgaagatg cagtttcaa gtgtatttgc     1800 aaacctgggt tccaactggc atcagatggc cgctactgca agatatcaa tgagtgtgag      1860 acacctggga tctgcatgaa cggacgctgt gtgaacacgg atggctccta cagatgcgaa     1920
tgcttccccg gattggctgt gggtctagac ggacgtgtgt gtgttgacac acacatgcgg     1980
agcacatgct atggaggata caggagaggc cagtgcgtga agccgttgtt tggtgctgtt     2040
accaaatcgg aatgctgttg tgccagcact gagtatgcct ttggggaacc ctgccagccg     2100
tgtcctgcac agaattcagc ggaatatcag gcactctgca gcagtggacc gggaatgaca     2160
tcagcaggca ctgatataaa cgaatgtgca ttagatcctg atatttgccc aaatggaatt     2220
tgtgaaaatc tccgtgggac ctacaaatgt atatgcaact cgggatatga agtagacata     2280
actgggaaaa actgtgtcga tattaatgag tgtgtgctga acagtctact ttgtgacaat     2340
ggacaatgtc gaaacacacc tggaagtttt gtctgcacct gccccaaagg atttgtgtac     2400
aaacctgacc taaaaacctg tgaagacatt gatgaatgtg aatcgagtcc ttgcattaat     2460
ggagtctgca gaacagccc tggctccttc atttgtgaat gttctcctga aagtactctg     2520
gacccaacaa aaaccatctg catagaaacc atcaagggca cttgctggca gactgtcatc     2580
gacgggcgct gtgagatcaa catcaacgga gccaccttga agtccgagtg ctgctcctcc     2640
cttggtgctg cgtggggag cccgtgcacc atctgtcaac ttgatcccat tgtgggtaaa     2700
gggttctcaa gaattaaagg cacgcaatgt gaagatatca atgagtgtga agtgttcccg     2760
ggagtatgca agaacggcct gtgtgtcaac tccagggggtt cattcaagtg cgagtgtccc     2820
aatggaatga ctttggatgc tacaggaaga atctgtcttg acatccgcct ggagacctgc     2880
ttcctcaagt atgacgatga agagtgcacc ttgcccatcg ctggccgcca ccgaatggat     2940
gcctgctgct gctctgttgg ggcagcctgg ggaacggaag agtgtgagga gtgtccattg     3000
```

```
agaaacagcc gggagtatga ggaactctgt ccccgaggac ctgggtttgc cacaaaagac   3060
attacaaatg ggaaacccttt cttcaaagat atcaatgagt gcaagatgat acccagcctc   3120
tgtacccacg gcaagtgcag gaacaccatt ggcagcttca agtgtaggtg tgacagtggc   3180
tttgctctgg attctgaaga gaggaactgt acagacattg atgagtgccg catatctcct   3240
gacctctgtg gccgaggcca gtgtgtgaac accccggggg actttgaatg caagtgtgat   3300
gaaggctatg aaagtggctt catgatgatg aagaactgca tggatattga tgaatgtcag   3360
agagatcctc tcctgtgtcg aggaggcatt tgccacaaca cagagggaag ctatcgctgc   3420
gaatgtcctc ctggtcacca attgtcccca aacatctctg catgcattga catcaacgag   3480
tgtgagctga gtgcgaatct ctgtccccat gggcgttgtg tgaacctcat agggaagtac   3540
cagtgtgcct gcaaccctgg ctaccacccc actcatgaca ggctcttctg tgtcgatatt   3600
gatgaatgca gcataatgaa cggtggttgt gagaccttct gcacaaactc tgacgggagc   3660
tatgaatgta gctgtcagcc aggcttcgcg ctaatgccag accagcgatc gtgcacagac   3720
attgatgagt gtgaagacaa ccccaatatc tgtgatggtg gccagtgcac aaacatacct   3780
ggggagtaca ggtgcctgtg ctatgatggg ttcatggcat ctgaagacat gaagacttgt   3840
gtggatgtca atgagtgtga cctgaatcca aacatctgcc ttagtgggac ctgtgaaaat   3900
actaaaggct cgttcatctg ccactgtgat atgggatatt cagggaagaa aggaaaaacg   3960
ggctgtacag atatcaatga atgtgagatc ggagcacaca actgtggcag acatgctgta   4020
tgcacaaata cagccgggag cttcaagtgc agctgcagtc ccggctggat ggagacggc   4080 attaagtgca cagatctgga tgaatgctct aatggaaccc acatgtgcag ccaacacgcg   4140
gactgcaaga acaccatggg gtcatatcgc tgtctctgta aggatggcta tacaggggat   4200
ggcttcacct gtacagacct cgacgagtgc tccgagaacc tgaacctctg tggcaatggc   4260
cagtgcctca cgcccctggg cgggtaccgc tgtgaatgcg acatgggctt cgtgcccagt   4320
gctgacggga aggcctgtga agatatcgat gagtgctccc ttccaaacat ctgtgtcttt   4380
ggaacttgcc acaacctccc gggcctcttc cgttgcgagt gtgagattgg ctatgaactg   4440
gaccgaagtg gtgaaactg cacagatgtt aatgagtgtc tggatccac cacctgcatc   4500 agtggaaact gtgtcaacac tcccggtagt tacacatgcg attgtcctcc ggattttgag   4560
ctgaatccaa ctcgtgtcgg ctgtgtcgat actcgctctg gaaactgcta tctggatatc   4620
cgaccccggg gagacaatgg agatacagcc tgcagcaatg aaattggagt tggtgtctct   4680
aaggcttcct gctgttgttc actgggtaaa gcttggggaa ccccatgtga gctgtgtcct   4740
tctgtgaaca catctgagta taaaattctt tgccctggag agaaggtttt cgtccaaat   4800 cccatcaccg ttatattgga agacatcgat gagtgccagg agcttccagg gctgtgccaa   4860 gggggaagt gcatcaatac ctttggcagc ttccagtgtc gctgtccaac tggttactac   4920
ctgaatgaag acactcgagt gtgtgatgat gtgaacgaat gtgagactcc tggaatctgt   4980
ggtccgggga cctgttacaa caccgttggc aactatacct gcatttgtcc tccagactac   5040
atgcaagtga acgggggaaa taattgcatg gacatgagaa gaagtctatg ctacagaaac   5100
tattacgctg acaaccagac ctgcgatgga gaactcctgt tcaacatgac caagaagatg   5160
tgctgttgct cctacaacat cggcagagcc tggaacaaac cctgtgaaca gtgccccatc   5220
ccaagcacag atgagtttgc tacccctctgt gggagccaga ggcccggctt cgtgattgac   5280
atttatacgg gtttacccgt ggatattgat gaatgccggg agatccctgg ggtctgtgaa   5340
```

```
aatggagtgt gcatcaacat ggttggcagc ttccggtgtg agtgtcccgt gggattcttc      5400
tataacgaca agttactggt ttgtgaagat atcgacgagt gtcagaatgg ccctgtgtgc      5460
cagcgaaatg cggaatgcat caacactgca ggcagctacc gctgtgactg taagcccggc      5520
taccgcctta cctccacagg tcaatgcaac gatcgaaacg agtgccaaga aatcccgaac      5580
atatgcagtc atggccagtg catcgacacc gtgggaagct tctactgcct ttgtcacact      5640
ggcttcaaaa caaatgtgga tcagaccatg tgcttagaca taaatgagtg tgagagagac      5700
gcctgtggga acgggacttg cagaaacacg attggctcct tcaactgtcg ctgtaaccat      5760
ggcttcatac tgtctcacaa caatgactgc atagatgttg atgagtgtgc aactggaaac      5820
gggaaccttt gcagaaatgg ccagtgtgtc aataccgtgg gctcctttca gtgcaggtgc      5880
aatgaaggct atgaggtggc tccggacggc aggacctgtg tggatatcaa cgagtgtgtt      5940
ctggatcctg ggaaatgtgc acctggaacc tgtcagaacc tggatggctc ctacagatgc      6000
atttgcccgc ctgggtatag tctacagaat gacaagtgtg aagatattga tgagtgtgtt      6060
gaagagccag aaatctgtgc cttggggacc tgcagcaaca ctgagggtag cttcaaatgt      6120
ctgtgtccag aggggttctc cctgtcctcc actggaagaa ggtgccaaga tttgcgaatg      6180
agctactgct atgcgaagtt tgaaggtggg aagtgttcat cacccaaatc cagaaaccat      6240
tccaagcagg agtgctgctg tgcttttgaag ggagaaggct ggggagatcc ttgtgagttg      6300
tgccccactg agccagatga ggcttttccgc cagatctgcc cctttggaag tgggatcatt      6360
gtgggccctg atgactcagc agttgatatg gacgaatgca agaacctga tgtctgtaga      6420
catgggcagt gcattaacac agacggctcc tatcgatgcg agtgtccttt tggttatatt      6480
ctggaaggga atgagtgtgt ggataccgat gaatgctctg tgggcaatcc ttgtggaaat      6540
gggacctgca agaatgtgat tggaggtttt gaatgtacct gtgaggaggg gttcgagcct      6600
ggcccaatga tgacttgtga agatataaat gaatgtgccc agaatcctct gctctgcgcc      6660
ttccgctgtg taaatacctca cgggtcctat gaatgcaaat gccctgttgg atacgttctc      6720
cgagaagaca ggaggatgtg taaagatgag gatgagtgtg cagagggaaa cacgactgt      6780
actgagaagc aaatggagtg taagaacctc attggtacct acatgtgcat ctgcggccct      6840
gggtaccagc gcagacccga tggagagggc tgcatagatg agaatgagtg tcagaccaag      6900
cccgggatct gtgagaatgg gcgttgcctc aacaccctgg gtagctacac ttgtgagtgt      6960
aacgatggct tcacagccag ccccactcag gatgagtgct tggacaaccg ggaagggtac      7020
tgcttttcgg aggtcttgca aaacatgtgc cagattggct caagcaacag gaaccccgtc      7080
accaagtccg agtgctgctg tgatggaggg agaggctggg gaccccactg tgagatctgc      7140
cctttcgagg gcacagtggc ttacaagaag ctctgtcccc acggccgagg attcatgacc      7200
aacggagcag atattgatga gtgcaaggtt attcatgatg tttgccgaaa tggggagtgt      7260
gtcaacgaca gagggtccta tcactgcatc tgtaaaactg gctacactcc ggatataaca      7320
gggaccgcct gtgtagatct gaatgaatgc aaccaggctc ccaaaccctg caatttttata      7380
tgcaaaaaca cagaagggag ttaccagtgt tcctgcccga agggctacat tctgcaagag      7440
gatgaaggag gctgcaaaga tcttgacgag tgtgcaacca agcagcataa ctgtcagttc      7500
ctgtgtgtta acaccatcgg tggcttcaca tgcaaatgcc ctcctgggtt tacccagcat      7560
cacactgcct gcattgataa caatgagtgc acgtctgata tcaacctgtg tgggtccaag      7620
ggtgtttgcc agaacactcc aggaagcttc acctgtgaat gccacggggg ttctcactc      7680
gatcagagtg gtgccagctg tgaagatgtg gacgagtgtg agggtaacca ccgctgtcaa      7740
```

| | |
|---|---|
| catggctgcc agaacatcat cggaggctat aggtgtagct gcccccaggg ctacctccag | 7800 |
| cactaccaat ggaaccagtg tgtagatgaa aacgagtgcc tgagtgcaca tgtctgtgga | 7860 |
| ggagcctcct gccacaacac cctggggagt tacaagtgca tgtgtcccac cggcttccag | 7920 |
| tacgaacagt tcagtggagg ctgccaagac atcaatgagt gtggctcatc ccaggccccc | 7980 |
| tgcagttacg gttgctctaa tactgagggt ggctacctgt gtggctgtcc accaggatac | 8040 |
| ttccggatag gccaagggca ttgtgtttct ggaatgggca tgggccgagg cggcccagag | 8100 |
| ccacctgcca gcagcgagat ggacgacaac tcactgtccc cagaggcctg ctatgagtgt | 8160 |
| aagatcaacg gctacccaaa ggcggcccag agccacctgc cagcaacgag gccggaaacg | 8220 |
| gagaagcacg aacgaaacgg atgcctccga catccaggac gggtctgaga tggaagccaa | 8280 |
| cgtgagcctc gccagctggg atgtggagaa gccggctagc tttgctttca atatttccca | 8340 |
| tgtcaataac aaggtccgaa tcctagagct cctgccggcc ctcacaactc tgatgaacca | 8400 |
| caacagatac ttgattgaat ctggaaatga agatggcttc tttaaaatca ccagaaaga | 8460 |
| aggggtcagc tacctccact tcacgaagaa gaagccggtg gctgggacct actccttaca | 8520 |
| aatcagcagc accccacttt ataaaaagaa agaacttaac cagttagaag acagatatga | 8580 |
| caaagactac ctcagtggtg aactgggcga taacctgaag atgaaaattc agatcttgct | 8640 |
| gcattaa | 8647 |

<210> SEQ ID NO 23
<211> LENGTH: 8620
<212> TYPE: DNA
<213> ORGANISM: Artificial Sequence
<220> FEATURE:
<223> OTHER INFORMATION: Synthetic

<400> SEQUENCE: 23

| | |
|---|---|
| atgcggcgag gagggctgct ggaggtcgcg ctggcgttcg ccctgctcct cgagtcctac | 60 |
| acgagccatg gggcggacgc caatttggag gctgggagc tgaaggagac cagagccaat | 120 |
| cgggccaaga gaagaggcgg cggaggacac gatgcgctga aggacccaa tgtctgtgga | 180 |
| tcacgttata atgcatactg ttgtcctgga tggaaaacct tacctggtgg aaatcagtgt | 240 |
| attgttccca tttgccggca ttcctgtggg gatggattct gctcgaggcc aaatatgtgc | 300 |
| acttgcccgt ctggtcagat atctccttcc tgtggctcca gatccatcca acactgcagc | 360 |
| atccgctgta tgaatggggg cagctgcagc gatgaccact gtctgtgcca gaaagggtac | 420 |
| atcggcactc actgtggaca gcctgtctgt gaaagtggct gtctcaacgg agggaggtgt | 480 |
| gtggccccaa tcggtgtgc ttgcacgtac ggctttactg accccagtg tgaaagagat | 540 |
| tacagaacag gccatgtttt tactgtgta agcaaccaga tgtgccaggg acagctcagc | 600 |
| gggattgtct gcaccaaaac actttgctgt gccaccgtgg gccgagcctg ggccacccc | 660 |
| tgtgagatgt gtcctgccca gcctcacccc tgccgccgcg gcttcattcc caacatccgc | 720 |
| actggagctt gtcaagatgt ggatgaatgt caggccatcc agggatgtg tcaaggagga | 780 |
| aattgcatta ataccgttgg atcttttgag tgcaaatgcc ctgctggaca caaatttaat | 840 |
| gaagtgtcac aaaaatgtga agatattgac gagtgcagca ccattcctgg agtctgcgat | 900 |
| ggcgggaat gtacaaacac tgtcagcagc tacttctgca aatgtcccc tggtttttac | 960 |
| acctctcctg atggcaccag atgcgtagat gttcgccctg ttactgcta cacagctctg | 1020 |
| gcaaacgggc gctgctctaa ccagctgcca cagtccataa ccaaaatgca gtgctgttgc | 1080 |

```
gatcttggcc ggtgctggtc tccaggggtt actgttgctc ccgagatgtg tcccatcagg    1140
tcaactgagg atttcaacaa gctgtgctct gtccctctgg taattcccgg gagaccagaa    1200
tatcctcccc cacccattgg ccccttcct ccagttcagc ccgttcctcc tggctatcct    1260
cctgggcctg tgattccagc ccctcggcca ccgccagaat atccatatcc atctccgtct    1320
cgggaaccac caagggtgct gcctttcaac gttactgact actgtcaact ggtccgctat    1380
ctctgtcaaa atgggcgctg cattccaact cccggtagct accgctgcga gtgcaacaag    1440
ggcttccagc tggatatccg tggcgaatgc atcgacgtgg atgagtgtga aagaaccca    1500 tgcactggtg gcgagtgcat caacaaccag ggctcctaca cctgtcactg cagagctggc    1560
taccagagca cactcaccag aactgagtgc agagacatag atgagtgtct tcagaatggc    1620
cggatctgca acaatggtcg ctgtatcaac acagacggca gcttccactg cgtatgcaat    1680
gcgggctttc atgtcacgcg ggacggaaag aactgtgaag atatggatga gtgcagcatc    1740
cgaaacatgt gcctaaacgg aatgtgtatt aatgaagatg cagtttcaa gtgtatttgc    1800 aaacctgggt tccaactggc atcagatggc cgctactgca aagatatcaa tgagtgtgag    1860
acacctggga tctgcatgaa cggacgctgt gtgaacacgg atggctccta cagatgcgaa    1920
tgcttccccg gattggctgt gggtctagac ggacgtgtgt gtgttgacac acacatgcgg    1980
agcacatgct atggaggata caggagaggc cagtgcgtga agccgttgtt tggtgctgtt    2040
accaaatcgg aatgctgttg tgccagcact gagtatgcct ttggggaacc ctgccagccg    2100
tgtcctgcac agaattcagc ggaatatcag gcactctgca gcagtggacc gggaatgaca    2160
tcagcaggca ctgatataaa cgaatgtgca ttagatcctg atatttgccc aaatggaatt    2220
tgtgaaaatc tccgtgggac ctacaaatgt atatgcaact cgggatatga agtagacata    2280
actgggaaaa actgtgtcga tattaatgag tgtgtgctga acagtctact ttgtgacaat    2340
ggacaatgtc gaaacacacc tggaagttttt gtctgcacct gccccaaagg atttgtgtac    2400
aaacctgacc taaaaacctg tgaagacatt gatgaatgtg aatcgagtcc ttgcattaat    2460
ggagtctgca agaacagccc tggctccttc atttgtgaat gttctcctga agtactctg    2520 gacccaacaa aaaccatctg catagaaacc atcaagggca cttgctggca gactgtcatc    2580
gacgggcgct gtgagatcaa catcaacgga gccaccttga agtccgagtg ctgctcctcc    2640
cttggtgctg cgtgggggag cccgtgcacc atctgtcaac ttgatcccat ttgtggtaaa    2700
gggttctcaa gaattaaagg cacgcaatgt gaagatatca atgagtgtga agtgttcccg    2760
ggagtatgca agaacggcct gtgtgtcaac tccagggggtt cattcaagtg cgagtgtccc    2820
aatggaatga ctttggatgc tacaggaaga atctgtcttg acatccgcct ggagacctgc    2880
ttcctcaagt atgacgatga agagtgcacc ttgcccatcg ctggccgcca ccgaatggat    2940
gcctgctgct gctctgttgg ggcagcctgg ggaacggaag agtgtgagga gtgtccattg    3000
agaaacagcc gggagtatga ggaactctgt cccgaggac ctgggtttgc cacaaaagac    3060
attacaaatg ggaaaccttt cttcaaagat atcaatgagt gcaagatgat acccagcctc    3120
tgtacccacg gcaagtgcag gaacaccatt ggcagcttca gtgtaggtg tgacagtggc    3180 tttgctctgg attctgaaga gaggaactgt acagacattg atgagtgccg catatctcct    3240
gacctctgtg gccgaggcca gtgtgtgaac accccgggg actttgaatg caagtgtgat    3300
gaaggctatg aaagtggctt catgatgatg aagaactgca tggatattga tgaatgtcag    3360
agagatcctc tcctgtgtcg aggaggcatt tgccacaaca cagagggaag ctatcgctgc    3420
gaatgtcctc ctggtcacca attgtcccca aacatctctg catgcattga catcaacgag    3480
```

```
tgtgagctga gtgcgaatct ctgtccccat gggcgttgtg tgaacctcat agggaagtac    3540
cagtgtgcct gcaaccctgg ctaccacccc actcatgaca ggctcttctg tgtcgatatt    3600
gatgaatgca gcataatgaa cggtggttgt gagaccttct gcacaaactc tgacgggagc    3660
tatgaatgta gctgtcagcc aggcttcgcg ctaatgccag accagcgatc gtgcacagac    3720
attgatgagt gtgaagacaa ccccaatatc tgtgatggtg ccagtgcac aaacatacct     3780 ggggagtaca ggtgcctgtg ctatgatggg ttcatggcat ctgaagacat gaagacttgt    3840
gtggatgtca atgagtgtga cctgaatcca acatctgcc ttagtgggac ctgtgaaaat     3900
actaaaggct cgttcatctg ccactgtgat atgggatatt cagggaagaa aggaaaaacg    3960
ggctgtacag atatcaatga atgtgagatc ggagcacaca actgtggcag acatgctgta    4020
tgcacaaata cagccgggag cttcaagtgc agctgcagtc ccggctggat ggagacggc     4080 attaagtgca cagatctgga tgaatgctct aatggaaccc acatgtgcag ccaacacgcg    4140
gactgcaaga caccatgggt gtcatatcgc tgtctctgta aggatggcta cagggggat     4200 ggcttcacct gtacagacct cgacgagtgc tccgagaacc tgaacctctg tggcaatggc    4260
cagtgcctca cgcccctggc gggtaccgc tgtgaatgcg acatgggctt cgtgcccagt     4320
gctgacggga aggcctgtga agatatcgat gagtgctccc ttccaaacat ctgtgtcttt    4380
ggaacttgcc acaacctccc gggcctcttc cgttgcgagt gtgagattgg ctatgaactg    4440
gaccgaagtg gtggaaactg cacagatgtt aatgagtgtc tggatcccac cacctgcatc    4500
agtggaaact gtgtcaacac tcccggtagt tacacatgcg attgtcctcc ggattttgag    4560
ctgaatccaa ctcgtgtcgg ctgtgtcgat actcgctctg gaaactgcta tctggatatc    4620
cgacccgggg gagacaatgg agatacagcc tgcagcaatg aaattggagt tggtgtctct    4680
aaggcttcct gctgttgttc actgggtaaa gcttggggaa ccccatgtga gctgtgtcct    4740
tctgtgaaca catctgagta taaaattctt tgccctggag gagaaggttt tcgtccaaat    4800
cccatcaccg ttatattgga agacatcgat gagtgccagg agcttccagg gctgtgccaa    4860 gggggggaagt gcatcaatac ctttggcagc ttccagtgtc gctgtccaac tggttactac    4920
ctgaatgaag acactcgagt gtgtgatgat gtgaacgaat gtgagactcc tggaatctgt    4980
ggtccgggga cctgttacaa caccgttggc aactatacct gcatttgtcc tccagactac    5040
atgcaagtga cgggggaaa taattgcatg gacatgagaa gaagtctatg ctacagaaac    5100
tattacgctg acaaccagac ctgcgatgga gaactcctgt tcaacatgac caagaagatg    5160
tgctgttgct cctacaacat cggcagagcc tggaacaaac cctgtgaaca gtgccccatc    5220
ccaagcacag atgagtttgc taccctctgt gggagccaga ggcccggctt cgtgattgac    5280
atttatacgg tgttaccccgt ggatattgat gaatgccggg agatccctgg ggtctgtgaa    5340
aatggagtgt gcatcaacat ggttggcagc ttccggtgtg agtgtcccgt gggattcttc    5400
tataacgaca agttactggt ttgtgaagat atcgacgagt gtcagaatgg ccctgtgtgc    5460
cagcgaaatg cggaatgcat caacactgca ggcagctacc gctgtgactg taagcccggc    5520
taccgcctta cctccacagg tcaatgcaac gatcgaaacg agtgccaaga aatcccgaac    5580
atatgcagtc atgccagtg catcgacacc gtgggaagct tctactgcct ttgtcacact    5640
ggcttcaaaa caaatgtgga tcagaccatg tgcttagaca taaatgagtg tgagagagac    5700
gcctgtggga acgggacttg cagaaacacg attggctcct tcaactgtcg ctgtaaccat    5760
ggcttcatac tgtctcacaa caatgactgc atagatgttg atgagtgtgc aactggaaac    5820
```

```
gggaaccttt gcagaaatgg ccagtgtgtc aataccgtgg gctcctttca gtgcaggtgc    5880
aatgaaggct atgaggtggc tccggacggc aggacctgtg tggatatcaa cgagtgtgtt    5940
ctggatcctg ggaaatgtgc acctggaacc tgtcagaacc tggatggctc ctacagatgc    6000
atttgcccgc ctgggtatag tctacagaat gacaagtgtg aagatattga tgagtgtgtt    6060
gaagagccag aaatctgtgc cttggggacc tgcagcaaca ctgagggtag cttcaaatgt    6120
ctgtgtccag aggggttctc cctgtcctcc actggaagaa ggtgccaaga tttgcgaatg    6180
agctactgct atgcgaagtt tgaaggtggg aagtgttcat cacccaaatc cagaaaccat    6240
tccaagcagg agtgctgctg tgctttgaag gagaaggct ggggagatcc ttgtgagttg    6300
tgccccactg agccagatga ggcttttccgc cagatctgcc cctttggaag tgggatcatt    6360
gtgggccctg atgactcagc agttgatatg gacgaatgca agaacctga tgtctgtaga    6420 catgggcagt gcattaacac agacggctcc tatcgatgcg agtgtccttt tggttatatt    6480
ctggaaggga atgagtgtgt ggataccgat gaatgtctg tgggcaatcc ttgtggaaat    6540
gggacctgca agaatgtgat tggaggtttt gaatgtacct gtgaggaggg gttcgagcct    6600
ggcccaatga tgacttgtga agatataaat gaatgtgccc agaatcctct gctctgcgcc    6660
ttccgctgtg taaataccta cgggtcctat gaatgcaaat gcctgttgg atacgttctc    6720 cgagaagaca ggaggatgtg taaagatgag gatgagtgtg cagagggaaa acacgactgt    6780
actgagaagc aaatggagtg taagaacctc attggtaccct acatgtgcat ctgcggccct    6840
gggtaccagc gcagacccga tggagagggc tgcatagatg agaatgagtg tcagaccaag    6900
cccgggatct gtgagaatgg gcgttgcctc aacaccctgg gtagctacac ttgtgagtgt    6960
aacgatggct tcacagccag ccccactcag gatgagtgct tggacaaccg ggaagggtac    7020
tgcttttcgg aggtcttgca aaacatgtgc cagattggct caagcaacag gaaccccgtc    7080
accaagtccg agtgctgctg tgatggaggg agaggctggg gaccccactg tgagatctgc    7140
cctttcgagg gcacagtggc ttacaagaag ctctgtcccc acggccgagg attcatgacc    7200
aacggagcag atattgatga gtgcaaggtt attcatgatg tttgccgaaa tgggagtgt    7260 gtcaacgaca gagggtccta tcactgcatc tgtaaaactg gctacactcc ggatataaca    7320
gggaccgcct gtgtagatct gaatgaatgc aaccaggctc ccaaaccctg caatttttata    7380 tgcaaaaaca cagaagggag ttaccagtgt cctgcccga agggctacat tctgcaagag    7440
gatggaagga gctgcaaaga tcttgacgag tgtgcaacca agcagcataa ctgtcagttc    7500
ctgtgtgtta acaccatcgg tggcttcaca tgcaaatgcc ctcctggggtt tacccagcat    7560 cacactgcct gcattgataa caatgagtgc acgtctgata tcaacctgtg tgggtccaag    7620 ggtgttttgcc agaacactcc aggaagcttc acctgtgaat gccacgggg gttctcactc    7680 gatcagagtg gtgccagctg tgaagatgtg gacgagtgtg agggtaacca ccgctgtcaa    7740
catggctgcc agaacatcat cggaggctat aggtgtagct gccccagggg ctacctccag    7800
cactaccaat ggaaccagtg tgtagatgaa acgagtgcc tgagtgcaca tgtctgtgga    7860
ggagcctcct gccacaacac cctggggagt tacaagtgca tgtgtcccac cggcttccag    7920
tacgaacagt tcagtggagg ctgccaagac atcaatgagt gtggctcatc ccaggccccc    7980
tgcagttacg gttgctctaa tactgagggt ggctacctgt gtggctgtcc accaggatac    8040
ttccggatag gccaagggca ttgtgttttct ggaatgggca tgggccgagg cggcccagag    8100
ccacctgcca gcagcgagat ggacgacaac tcactgtccc cagaggcctg ctatgagtgt    8160
gatcaatggc taccccaaac ggggcaggaa acggagaagc acaaacgaaa ctgatgcctc    8220
```

```
cgacatccag gacgggtctg agatggaagc caacgtgagc ctcgccagct gggatgtgga    8280
gaagccggct agctttgctt tcaatatttc ccatgtcaat aacaaggtcc gaatcctaga    8340
gctcctgccg gccctcacaa ctctgatgaa ccacaacaga tacttgattg aatctggaaa    8400
tgaagatggc ttctttaaaa tcaaccagaa agaaggggtc agctacctcc acttcacgaa    8460
gaagaagccg gtggctggga cctactcctt acaaatcagc agcacccccac tttataaaaa    8520 gaaagaactt aaccagttag aagacagata tgacaaagac tacctcagtg gtgaactggg    8580
cgataacctg aagatgaaaa ttcagatctt gctgcattaa                          8620
```

<210> SEQ ID NO 24
<211> LENGTH: 175
<212> TYPE: DNA
<213> ORGANISM: Homo sapiens

<400> SEQUENCE: 24

```
gcactgtgtt tctggaatgg gcatgggccg aggaaaccca gagccacctg tcagtggtga     60
aatggatgac aattcactct ccccagaggc ttgttacgag tgtaagatca atggctaccc    120
caaacggggc aggaaacgga gaagcacaaa cgaaactgat gcctccaata tcgag         175
```

<210> SEQ ID NO 25
<211> LENGTH: 175
<212> TYPE: DNA
<213> ORGANISM: Mus musculus

<400> SEQUENCE: 25

```
gcattgtgtt tctggaatgg gcatgggccg aggcggccca gagccacctg ccagcagcga     60
gatggacgac aactcactgt ccccagaggc ctgctatgag tgtaagatca acggctaccc    120
aaaacgaggc cggaaacgga gaagcacgaa cgaaacggat gcctccgaca tccag         175
```

<210> SEQ ID NO 26
<211> LENGTH: 176
<212> TYPE: DNA
<213> ORGANISM: Artificial Sequence
<220> FEATURE:
<223> OTHER INFORMATION: Synthetic

<400> SEQUENCE: 26

```
gcattgtgtt tctggaatgg gcatgggccg aggcggccca gagccacctg ccagcagcga     60
gatggacgac aactcactgt ccccagaggc ctgctatgag tgtaagatca acggctaccc    120
aaaacgaggc cggaaacgga gaagcacgaa cgaaaactga tgcctccgac atccag        176
```

<210> SEQ ID NO 27
<211> LENGTH: 200
<212> TYPE: DNA
<213> ORGANISM: Artificial Sequence
<220> FEATURE:
<223> OTHER INFORMATION: Synthetic

<400> SEQUENCE: 27

```
gcattgtgtt tctggaatgg gcatgggccg aggcggccca gagccacctg ccagcagcga     60
gatggacgac aactcactgt ccccagaggc ctgctatgag tgtaagatca acggctaccc    120
aaaggcggcc cagagccacc tgccagcaac gaggccggaa acggagaagc acgaacgaaa    180
cggatgcctc cgacatccag                                                200
```

<210> SEQ ID NO 28

<211> LENGTH: 173
<212> TYPE: DNA
<213> ORGANISM: Artificial Sequence
<220> FEATURE:
<223> OTHER INFORMATION: Synthetic

<400> SEQUENCE: 28

```
gcattgtgtt tctggaatgg gcatgggccg aggcggccca gagccacctg ccagcagcga    60
gatggacgac aactcactgt ccccagaggc ctgctatgag tgtgatcaat ggctacccca   120
aacggggcag gaaacggaga agcacaaacg aaactgatgc ctccgacatc cag          173
```

<210> SEQ ID NO 29
<211> LENGTH: 2871
<212> TYPE: PRT
<213> ORGANISM: Homo sapiens

<400> SEQUENCE: 29

```
Met Arg Arg Gly Arg Leu Leu Glu Ile Ala Leu Gly Phe Thr Val Leu
1               5                   10                  15

Leu Ala Ser Tyr Thr Ser His Gly Ala Asp Ala Asn Leu Glu Ala Gly
                20                  25                  30

Asn Val Lys Glu Thr Arg Ala Ser Arg Ala Lys Arg Arg Gly Gly Gly
            35                  40                  45

Gly His Asp Ala Leu Lys Gly Pro Asn Val Cys Gly Ser Arg Tyr Asn
        50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ala Pro Ser Cys Gly
                100                 105                 110

Ser Arg Ser Ile Gln His Cys Asn Ile Arg Cys Met Asn Gly Gly Ser
            115                 120                 125

Cys Ser Asp Asp His Cys Leu Cys Gln Lys Gly Tyr Ile Gly Thr His
        130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Ile Ser Asn
                180                 185                 190

Gln Met Cys Gln Gly Gln Leu Ser Gly Ile Val Cys Thr Lys Thr Leu
            195                 200                 205

Cys Cys Ala Thr Val Gly Arg Ala Trp Gly His Pro Cys Glu Met Cys
        210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Leu
                245                 250                 255

Cys Gln Gly Gly Asn Cys Ile Asn Thr Val Gly Ser Phe Glu Cys Lys
                260                 265                 270

Cys Pro Ala Gly His Lys Leu Asn Glu Val Ser Gln Lys Cys Glu Asp
            275                 280                 285

Ile Asp Glu Cys Ser Thr Ile Pro Gly Ile Cys Glu Gly Gly Glu Cys
        290                 295                 300
```

```
Thr Asn Thr Val Ser Ser Tyr Phe Cys Lys Cys Pro Gly Phe Tyr
305                 310                 315                 320

Thr Ser Pro Asp Gly Thr Arg Cys Ile Asp Val Arg Pro Gly Tyr Cys
            325                 330                 335

Tyr Thr Ala Leu Thr Asn Gly Arg Cys Ser Asn Gln Leu Pro Gln Ser
            340                 345                 350

Ile Thr Lys Met Gln Cys Cys Asp Ala Gly Arg Cys Trp Ser Pro
            355                 360                 365

Gly Val Thr Val Ala Pro Glu Met Cys Pro Ile Arg Ala Thr Glu Asp
            370                 375                 380

Phe Asn Lys Leu Cys Ser Val Pro Met Val Ile Pro Gly Arg Pro Glu
385                 390                 395                 400

Tyr Pro Pro Pro Leu Gly Pro Ile Pro Val Leu Pro Val Pro
            405                 410                 415

Pro Gly Phe Pro Pro Gly Pro Gln Ile Pro Val Pro Arg Pro Pro Val
            420                 425                 430

Glu Tyr Leu Tyr Pro Ser Arg Glu Pro Pro Arg Val Leu Pro Val Asn
            435                 440                 445

Val Thr Asp Tyr Cys Gln Leu Val Arg Tyr Leu Cys Gln Asn Gly Arg
450                 455                 460

Cys Ile Pro Thr Pro Gly Ser Tyr Arg Cys Glu Cys Asn Lys Gly Phe
465                 470                 475                 480

Gln Leu Asp Leu Arg Gly Glu Cys Ile Asp Val Asp Glu Cys Glu Lys
            485                 490                 495

Asn Pro Cys Ala Gly Gly Glu Cys Ile Asn Asn Gln Gly Ser Tyr Thr
            500                 505                 510

Cys Gln Cys Arg Ala Gly Tyr Gln Ser Thr Leu Thr Arg Thr Glu Cys
            515                 520                 525

Arg Asp Ile Asp Glu Cys Leu Gln Asn Gly Arg Ile Cys Asn Asn Gly
            530                 535                 540

Arg Cys Ile Asn Thr Asp Gly Ser Phe His Cys Val Cys Asn Ala Gly
545                 550                 555                 560

Phe His Val Thr Arg Asp Gly Lys Asn Cys Glu Asp Met Asp Glu Cys
            565                 570                 575

Ser Ile Arg Asn Met Cys Leu Asn Gly Met Cys Ile Asn Glu Asp Gly
            580                 585                 590

Ser Phe Lys Cys Ile Cys Lys Pro Gly Phe Gln Leu Ala Ser Asp Gly
            595                 600                 605

Arg Tyr Cys Lys Asp Ile Asn Glu Cys Glu Thr Pro Gly Ile Cys Met
            610                 615                 620

Asn Gly Arg Cys Val Asn Thr Asp Gly Ser Tyr Arg Cys Glu Cys Phe
625                 630                 635                 640

Pro Gly Leu Ala Val Gly Leu Asp Gly Arg Val Cys Val Asp Thr His
            645                 650                 655

Met Arg Ser Thr Cys Tyr Gly Gly Tyr Lys Arg Gly Gln Cys Ile Lys
            660                 665                 670

Pro Leu Phe Gly Ala Val Thr Lys Ser Glu Cys Cys Cys Ala Ser Thr
            675                 680                 685

Glu Tyr Ala Phe Gly Glu Pro Cys Gln Pro Cys Pro Ala Gln Asn Ser
            690                 695                 700

Ala Glu Tyr Gln Ala Leu Cys Ser Ser Gly Pro Gly Met Thr Ser Ala
705                 710                 715                 720

Gly Ser Asp Ile Asn Glu Cys Ala Leu Asp Pro Asp Ile Cys Pro Asn
```

725                 730                 735
Gly Ile Cys Glu Asn Leu Arg Gly Thr Tyr Lys Cys Ile Cys Asn Ser
            740                 745                 750
Gly Tyr Glu Val Asp Ser Thr Gly Lys Asn Cys Val Asp Ile Asn Glu
            755                 760                 765
Cys Val Leu Asn Ser Leu Leu Cys Asp Asn Gly Gln Cys Arg Asn Thr
            770                 775                 780
Pro Gly Ser Phe Val Cys Thr Cys Pro Lys Gly Phe Ile Tyr Lys Pro
785                 790                 795                 800
Asp Leu Lys Thr Cys Glu Asp Ile Asp Glu Cys Glu Ser Ser Pro Cys
            805                 810                 815
Ile Asn Gly Val Cys Lys Asn Ser Pro Gly Ser Phe Ile Cys Glu Cys
            820                 825                 830
Ser Ser Glu Ser Thr Leu Asp Pro Thr Lys Thr Ile Cys Ile Glu Thr
            835                 840                 845
Ile Lys Gly Thr Cys Trp Gln Thr Val Ile Asp Gly Arg Cys Glu Ile
            850                 855                 860
Asn Ile Asn Gly Ala Thr Leu Lys Ser Gln Cys Cys Ser Ser Leu Gly
865                 870                 875                 880
Ala Ala Trp Gly Ser Pro Cys Thr Leu Cys Gln Val Asp Pro Ile Cys
                        885                 890                 895
Gly Lys Gly Tyr Ser Arg Ile Lys Gly Thr Gln Cys Glu Asp Ile Asp
            900                 905                 910
Glu Cys Glu Val Phe Pro Gly Val Cys Lys Asn Gly Leu Cys Val Asn
            915                 920                 925
Thr Arg Gly Ser Phe Lys Cys Gln Cys Pro Ser Gly Met Thr Leu Asp
930                 935                 940
Ala Thr Gly Arg Ile Cys Leu Asp Ile Arg Leu Glu Thr Cys Phe Leu
945                 950                 955                 960
Arg Tyr Glu Asp Glu Glu Cys Thr Leu Pro Ile Ala Gly Arg His Arg
                        965                 970                 975
Met Asp Ala Cys Cys Cys Ser Val Gly Ala Ala Trp Gly Thr Glu Glu
            980                 985                 990
Cys Glu Glu Cys Pro Met Arg Asn Thr Pro Glu Tyr Glu Glu Leu Cys
            995                 1000                1005
Pro Arg Gly Pro Gly Phe Ala Thr Lys Glu Ile Thr Asn Gly Lys
            1010                1015                1020
Pro Phe Phe Lys Asp Ile Asn Glu Cys Lys Met Ile Pro Ser Leu
            1025                1030                1035
Cys Thr His Gly Lys Cys Arg Asn Thr Ile Gly Ser Phe Lys Cys
            1040                1045                1050
Arg Cys Asp Ser Gly Phe Ala Leu Asp Ser Glu Glu Arg Asn Cys
            1055                1060                1065
Thr Asp Ile Asp Glu Cys Arg Ile Ser Pro Asp Leu Cys Gly Arg
            1070                1075                1080
Gly Gln Cys Val Asn Thr Pro Gly Asp Phe Glu Cys Lys Cys Asp
            1085                1090                1095
Glu Gly Tyr Glu Ser Gly Phe Met Met Met Lys Asn Cys Met Asp
            1100                1105                1110
Ile Asp Glu Cys Gln Arg Asp Pro Leu Leu Cys Arg Gly Gly Val
            1115                1120                1125
Cys His Asn Thr Glu Gly Ser Tyr Arg Cys Glu Cys Pro Pro Gly
            1130                1135                1140

-continued

```
His Gln Leu Ser Pro Asn Ile Ser Ala Cys Ile Asp Ile Asn Glu
    1145                1150                1155
Cys Glu Leu Ser Ala His Leu Cys Pro Asn Gly Arg Cys Val Asn
    1160                1165                1170
Leu Ile Gly Lys Tyr Gln Cys Ala Cys Asn Pro Gly Tyr His Ser
    1175                1180                1185
Thr Pro Asp Arg Leu Phe Cys Val Asp Ile Asp Glu Cys Ser Ile
    1190                1195                1200
Met Asn Gly Gly Cys Glu Thr Phe Cys Thr Asn Ser Glu Gly Ser
    1205                1210                1215
Tyr Glu Cys Ser Cys Gln Pro Gly Phe Ala Leu Met Pro Asp Gln
    1220                1225                1230
Arg Ser Cys Thr Asp Ile Asp Glu Cys Glu Asp Asn Pro Asn Ile
    1235                1240                1245
Cys Asp Gly Gly Gln Cys Thr Asn Ile Pro Gly Glu Tyr Arg Cys
    1250                1255                1260
Leu Cys Tyr Asp Gly Phe Met Ala Ser Glu Asp Met Lys Thr Cys
    1265                1270                1275
Val Asp Val Asn Glu Cys Asp Leu Asn Pro Asn Ile Cys Leu Ser
    1280                1285                1290
Gly Thr Cys Glu Asn Thr Lys Gly Ser Phe Ile Cys His Cys Asp
    1295                1300                1305
Met Gly Tyr Ser Gly Lys Lys Gly Lys Thr Gly Cys Thr Asp Ile
    1310                1315                1320
Asn Glu Cys Glu Ile Gly Ala His Asn Cys Gly Lys His Ala Val
    1325                1330                1335
Cys Thr Asn Thr Ala Gly Ser Phe Lys Cys Ser Cys Ser Pro Gly
    1340                1345                1350
Trp Ile Gly Asp Gly Ile Lys Cys Thr Asp Leu Asp Glu Cys Ser
    1355                1360                1365
Asn Gly Thr His Met Cys Ser Gln His Ala Asp Cys Lys Asn Thr
    1370                1375                1380
Met Gly Ser Tyr Arg Cys Leu Cys Lys Glu Gly Tyr Thr Gly Asp
    1385                1390                1395
Gly Phe Thr Cys Thr Asp Leu Asp Glu Cys Ser Glu Asn Leu Asn
    1400                1405                1410
Leu Cys Gly Asn Gly Gln Cys Leu Asn Ala Pro Gly Gly Tyr Arg
    1415                1420                1425
Cys Glu Cys Asp Met Gly Phe Val Pro Ser Ala Asp Gly Lys Ala
    1430                1435                1440
Cys Glu Asp Ile Asp Glu Cys Ser Leu Pro Asn Ile Cys Val Phe
    1445                1450                1455
Gly Thr Cys His Asn Leu Pro Gly Leu Phe Arg Cys Glu Cys Glu
    1460                1465                1470
Ile Gly Tyr Glu Leu Asp Arg Ser Gly Gly Asn Cys Thr Asp Val
    1475                1480                1485
Asn Glu Cys Leu Asp Pro Thr Thr Cys Ile Ser Gly Asn Cys Val
    1490                1495                1500
Asn Thr Pro Gly Ser Tyr Ile Cys Asp Cys Pro Pro Asp Phe Glu
    1505                1510                1515
Leu Asn Pro Thr Arg Val Gly Cys Val Asp Thr Arg Ser Gly Asn
    1520                1525                1530
```

-continued

Cys Tyr Leu Asp Ile Arg Pro Arg Gly Asp Asn Gly Asp Thr Ala
1535                1540                1545

Cys Ser Asn Glu Ile Gly Val Gly Val Ser Lys Ala Ser Cys Cys
1550                1555                1560

Cys Ser Leu Gly Lys Ala Trp Gly Thr Pro Cys Glu Met Cys Pro
1565                1570                1575

Ala Val Asn Thr Ser Glu Tyr Lys Ile Leu Cys Pro Gly Gly Glu
1580                1585                1590

Gly Phe Arg Pro Asn Pro Ile Thr Val Ile Leu Glu Asp Ile Asp
1595                1600                1605

Glu Cys Gln Glu Leu Pro Gly Leu Cys Gln Gly Gly Lys Cys Ile
1610                1615                1620

Asn Thr Phe Gly Ser Phe Gln Cys Arg Cys Pro Thr Gly Tyr Tyr
1625                1630                1635

Leu Asn Glu Asp Thr Arg Val Cys Asp Asp Val Asn Glu Cys Glu
1640                1645                1650

Thr Pro Gly Ile Cys Gly Pro Gly Thr Cys Tyr Asn Thr Val Gly
1655                1660                1665

Asn Tyr Thr Cys Ile Cys Pro Pro Asp Tyr Met Gln Val Asn Gly
1670                1675                1680

Gly Asn Asn Cys Met Asp Met Arg Arg Ser Leu Cys Tyr Arg Asn
1685                1690                1695

Tyr Tyr Ala Asp Asn Gln Thr Cys Asp Gly Glu Leu Leu Phe Asn
1700                1705                1710

Met Thr Lys Lys Met Cys Cys Cys Ser Tyr Asn Ile Gly Arg Ala
1715                1720                1725

Trp Asn Lys Pro Cys Glu Gln Cys Pro Ile Pro Ser Thr Asp Glu
1730                1735                1740

Phe Ala Thr Leu Cys Gly Ser Gln Arg Pro Gly Phe Val Ile Asp
1745                1750                1755

Ile Tyr Thr Gly Leu Pro Val Asp Ile Asp Glu Cys Arg Glu Ile
1760                1765                1770

Pro Gly Val Cys Glu Asn Gly Val Cys Ile Asn Met Val Gly Ser
1775                1780                1785

Phe Arg Cys Glu Cys Pro Val Gly Phe Phe Tyr Asn Asp Lys Leu
1790                1795                1800

Leu Val Cys Glu Asp Ile Asp Glu Cys Gln Asn Gly Pro Val Cys
1805                1810                1815

Gln Arg Asn Ala Glu Cys Ile Asn Thr Ala Gly Ser Tyr Arg Cys
1820                1825                1830

Asp Cys Lys Pro Gly Tyr Arg Phe Thr Ser Thr Gly Gln Cys Asn
1835                1840                1845

Asp Arg Asn Glu Cys Gln Glu Ile Pro Asn Ile Cys Ser His Gly
1850                1855                1860

Gln Cys Ile Asp Thr Val Gly Ser Phe Tyr Cys Leu Cys His Thr
1865                1870                1875

Gly Phe Lys Thr Asn Asp Asp Gln Thr Met Cys Leu Asp Ile Asn
1880                1885                1890

Glu Cys Glu Arg Asp Ala Cys Gly Asn Gly Thr Cys Arg Asn Thr
1895                1900                1905

Ile Gly Ser Phe Asn Cys Arg Cys Asn His Gly Phe Ile Leu Ser
1910                1915                1920

His Asn Asn Asp Cys Ile Asp Val Asp Glu Cys Ala Ser Gly Asn

-continued

```
            1925                1930                1935

Gly Asn Leu Cys Arg Asn Gly Gln Cys Ile Asn Thr Val Gly Ser
        1940                1945                1950

Phe Gln Cys Gln Cys Asn Glu Gly Tyr Glu Val Ala Pro Asp Gly
        1955                1960                1965

Arg Thr Cys Val Asp Ile Asn Glu Cys Leu Leu Glu Pro Arg Lys
        1970                1975                1980

Cys Ala Pro Gly Thr Cys Gln Asn Leu Asp Gly Ser Tyr Arg Cys
        1985                1990                1995

Ile Cys Pro Pro Gly Tyr Ser Leu Gln Asn Glu Lys Cys Glu Asp
        2000                2005                2010

Ile Asp Glu Cys Val Glu Glu Pro Glu Ile Cys Ala Leu Gly Thr
        2015                2020                2025

Cys Ser Asn Thr Glu Gly Ser Phe Lys Cys Leu Cys Pro Glu Gly
        2030                2035                2040

Phe Ser Leu Ser Ser Ser Gly Arg Arg Cys Gln Asp Leu Arg Met
        2045                2050                2055

Ser Tyr Cys Tyr Ala Lys Phe Glu Gly Gly Lys Cys Ser Ser Pro
        2060                2065                2070

Lys Ser Arg Asn His Ser Lys Gln Glu Cys Cys Cys Ala Leu Lys
        2075                2080                2085

Gly Glu Gly Trp Gly Asp Pro Cys Glu Leu Cys Pro Thr Glu Pro
        2090                2095                2100

Asp Glu Ala Phe Arg Gln Ile Cys Pro Tyr Gly Ser Gly Ile Ile
        2105                2110                2115

Val Gly Pro Asp Asp Ser Ala Val Asp Met Asp Glu Cys Lys Glu
        2120                2125                2130

Pro Asp Val Cys Lys His Gly Gln Cys Ile Asn Thr Asp Gly Ser
        2135                2140                2145

Tyr Arg Cys Glu Cys Pro Phe Gly Tyr Ile Leu Ala Gly Asn Glu
        2150                2155                2160

Cys Val Asp Thr Asp Glu Cys Ser Val Gly Asn Pro Cys Gly Asn
        2165                2170                2175

Gly Thr Cys Lys Asn Val Ile Gly Gly Phe Glu Cys Thr Cys Glu
        2180                2185                2190

Glu Gly Phe Glu Pro Gly Pro Met Met Thr Cys Glu Asp Ile Asn
        2195                2200                2205

Glu Cys Ala Gln Asn Pro Leu Leu Cys Ala Phe Arg Cys Val Asn
        2210                2215                2220

Thr Tyr Gly Ser Tyr Glu Cys Lys Cys Pro Val Gly Tyr Val Leu
        2225                2230                2235

Arg Glu Asp Arg Arg Met Cys Lys Asp Glu Asp Glu Cys Glu Glu
        2240                2245                2250

Gly Lys His Asp Cys Thr Glu Lys Gln Met Glu Cys Lys Asn Leu
        2255                2260                2265

Ile Gly Thr Tyr Met Cys Ile Cys Gly Pro Gly Tyr Gln Arg Arg
        2270                2275                2280

Pro Asp Gly Glu Gly Cys Val Asp Glu Asn Glu Cys Gln Thr Lys
        2285                2290                2295

Pro Gly Ile Cys Glu Asn Gly Arg Cys Leu Asn Thr Arg Gly Ser
        2300                2305                2310

Tyr Thr Cys Glu Cys Asn Asp Gly Phe Thr Ala Ser Pro Asn Gln
        2315                2320                2325
```

-continued

```
Asp Glu Cys Leu Asp Asn Arg Glu Gly Tyr Cys Phe Thr Glu Val
    2330                2335                2340

Leu Gln Asn Met Cys Gln Ile Gly Ser Ser Asn Arg Asn Pro Val
    2345                2350                2355

Thr Lys Ser Glu Cys Cys Asp Gly Arg Gly Trp Gly Pro
    2360                2365                2370

His Cys Glu Ile Cys Pro Phe Gln Gly Thr Val Ala Phe Lys Lys
    2375                2380                2385

Leu Cys Pro His Gly Arg Gly Phe Met Thr Asn Gly Ala Asp Ile
    2390                2395                2400

Asp Glu Cys Lys Val Ile His Asp Val Cys Arg Asn Gly Glu Cys
    2405                2410                2415

Val Asn Asp Arg Gly Ser Tyr His Cys Ile Cys Lys Thr Gly Tyr
    2420                2425                2430

Thr Pro Asp Ile Thr Gly Thr Ser Cys Val Asp Leu Asn Glu Cys
    2435                2440                2445

Asn Gln Ala Pro Lys Pro Cys Asn Phe Ile Cys Lys Asn Thr Glu
    2450                2455                2460

Gly Ser Tyr Gln Cys Ser Cys Pro Lys Gly Tyr Ile Leu Gln Glu
    2465                2470                2475

Asp Gly Arg Ser Cys Lys Asp Leu Asp Glu Cys Ala Thr Lys Gln
    2480                2485                2490

His Asn Cys Gln Phe Leu Cys Val Asn Thr Ile Gly Gly Phe Thr
    2495                2500                2505

Cys Lys Cys Pro Pro Gly Phe Thr Gln His His Thr Ser Cys Ile
    2510                2515                2520

Asp Asn Asn Glu Cys Thr Ser Asp Ile Asn Leu Cys Gly Ser Lys
    2525                2530                2535

Gly Ile Cys Gln Asn Thr Pro Gly Ser Phe Thr Cys Glu Cys Gln
    2540                2545                2550

Arg Gly Phe Ser Leu Asp Gln Thr Gly Ser Ser Cys Glu Asp Val
    2555                2560                2565

Asp Glu Cys Glu Gly Asn His Arg Cys Gln His Gly Cys Gln Asn
    2570                2575                2580

Ile Ile Gly Gly Tyr Arg Cys Ser Cys Pro Gln Gly Tyr Leu Gln
    2585                2590                2595

His Tyr Gln Trp Asn Gln Cys Val Asp Glu Asn Glu Cys Leu Ser
    2600                2605                2610

Ala His Ile Cys Gly Gly Ala Ser Cys His Asn Thr Leu Gly Ser
    2615                2620                2625

Tyr Lys Cys Met Cys Pro Ala Gly Phe Gln Tyr Glu Gln Phe Ser
    2630                2635                2640

Gly Gly Cys Gln Asp Ile Asn Glu Cys Gly Ser Ala Gln Ala Pro
    2645                2650                2655

Cys Ser Tyr Gly Cys Ser Asn Thr Glu Gly Gly Tyr Leu Cys Gly
    2660                2665                2670

Cys Pro Pro Gly Tyr Phe Arg Ile Gly Gln Gly His Cys Val Ser
    2675                2680                2685

Gly Met Gly Met Gly Arg Gly Asn Pro Glu Pro Pro Val Ser Gly
    2690                2695                2700

Glu Met Asp Asp Asn Ser Leu Ser Pro Glu Ala Cys Tyr Glu Cys
    2705                2710                2715
```

-continued

```
Lys Ile Asn Gly Tyr Pro Lys Arg Gly Arg Lys Arg Arg Ser Thr
2720                2725                2730

Asn Glu Thr Asp Ala Ser Asn Ile Glu Asp Gln Ser Glu Thr Glu
    2735                2740                2745

Ala Asn Val Ser Leu Ala Ser Trp Asp Val Glu Lys Thr Ala Ile
    2750                2755                2760

Phe Ala Phe Asn Ile Ser His Val Ser Asn Lys Val Arg Ile Leu
    2765                2770                2775

Glu Leu Leu Pro Ala Leu Thr Thr Leu Thr Asn His Asn Arg Tyr
    2780                2785                2790

Leu Ile Glu Ser Gly Asn Glu Asp Gly Phe Phe Lys Ile Asn Gln
    2795                2800                2805

Lys Glu Gly Ile Ser Tyr Leu His Phe Thr Lys Lys Lys Pro Val
    2810                2815                2820

Ala Gly Thr Tyr Ser Leu Gln Ile Ser Ser Thr Pro Leu Tyr Lys
    2825                2830                2835

Lys Lys Glu Leu Asn Gln Leu Glu Asp Lys Tyr Asp Lys Asp Tyr
    2840                2845                2850

Leu Ser Gly Glu Leu Gly Asp Asn Leu Lys Met Lys Ile Gln Val
    2855                2860                2865

Leu Leu His
    2870

<210> SEQ ID NO 30
<211> LENGTH: 2873
<212> TYPE: PRT
<213> ORGANISM: Mus musculus

<400> SEQUENCE: 30

Met Arg Arg Gly Gly Leu Leu Glu Val Ala Leu Ala Phe Ala Leu Leu
1               5                   10                  15

Leu Glu Ser Tyr Thr Ser His Gly Ala Asp Ala Asn Leu Glu Ala Gly
            20                  25                  30

Ser Leu Lys Glu Thr Arg Ala Asn Arg Ala Lys Arg Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
        115                 120                 125

Cys Ser Asp Asp His Cys Leu Cys Gln Lys Gly Tyr Ile Gly Thr His
    130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
        195                 200                 205
```

-continued

```
Cys Cys Ala Thr Val Gly Arg Ala Trp Gly His Pro Cys Glu Met Cys
    210                 215                 220
Pro Ala Gln Pro His Pro Cys Arg Arg Gly Phe Ile Pro Asn Ile Arg
225                 230                 235                 240
Thr Gly Ala Cys Gln Asp Val Asp Glu Cys Gln Ala Ile Pro Gly Met
                245                 250                 255
Cys Gln Gly Gly Asn Cys Ile Asn Thr Val Gly Ser Phe Glu Cys Lys
                260                 265                 270
Cys Pro Ala Gly His Lys Phe Asn Glu Val Ser Gln Lys Cys Glu Asp
            275                 280                 285
Ile Asp Glu Cys Ser Thr Ile Pro Gly Val Cys Asp Gly Gly Glu Cys
290                 295                 300
Thr Asn Thr Val Ser Ser Tyr Phe Cys Lys Cys Pro Pro Gly Phe Tyr
305                 310                 315                 320
Thr Ser Pro Asp Gly Thr Arg Cys Val Asp Val Arg Pro Gly Tyr Cys
                325                 330                 335
Tyr Thr Ala Leu Ala Asn Gly Arg Cys Ser Asn Gln Leu Pro Gln Ser
                340                 345                 350
Ile Thr Lys Met Gln Cys Cys Asp Leu Gly Arg Cys Trp Ser Pro
            355                 360                 365
Gly Val Thr Val Ala Pro Glu Met Cys Pro Ile Arg Ser Thr Glu Asp
370                 375                 380
Phe Asn Lys Leu Cys Ser Val Pro Leu Val Ile Pro Gly Arg Pro Glu
385                 390                 395                 400
Tyr Pro Pro Pro Pro Ile Gly Pro Leu Pro Pro Val Gln Pro Val Pro
                405                 410                 415
Pro Gly Tyr Pro Pro Gly Pro Val Ile Pro Ala Pro Arg Pro Pro Pro
                420                 425                 430
Glu Tyr Pro Tyr Pro Ser Pro Ser Arg Glu Pro Pro Arg Val Leu Pro
                435                 440                 445
Phe Asn Val Thr Asp Tyr Cys Gln Leu Val Arg Tyr Leu Cys Gln Asn
450                 455                 460
Gly Arg Cys Ile Pro Thr Pro Gly Ser Tyr Arg Cys Glu Cys Asn Lys
465                 470                 475                 480
Gly Phe Gln Leu Asp Ile Arg Gly Glu Cys Ile Asp Val Asp Glu Cys
                485                 490                 495
Glu Lys Asn Pro Cys Thr Gly Gly Cys Ile Asn Asn Gln Gly Ser
                500                 505                 510
Tyr Thr Cys His Cys Arg Ala Gly Tyr Gln Ser Thr Leu Thr Arg Thr
            515                 520                 525
Glu Cys Arg Asp Ile Asp Glu Cys Leu Gln Asn Gly Arg Ile Cys Asn
530                 535                 540
Asn Gly Arg Cys Ile Asn Thr Asp Gly Ser Phe His Cys Val Cys Asn
545                 550                 555                 560
Ala Gly Phe His Val Thr Arg Asp Gly Lys Asn Cys Glu Asp Met Asp
                565                 570                 575
Glu Cys Ser Ile Arg Asn Met Cys Leu Asn Gly Met Cys Ile Asn Glu
                580                 585                 590
Asp Gly Ser Phe Lys Cys Ile Cys Lys Pro Gly Phe Gln Leu Ala Ser
            595                 600                 605
Asp Gly Arg Tyr Cys Lys Asp Ile Asn Glu Cys Glu Thr Pro Gly Ile
610                 615                 620
```

```
Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
            645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
            675                 680                 685

Ser Thr Glu Tyr Ala Phe Gly Glu Pro Cys Gln Pro Cys Pro Ala Gln
690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
            725                 730                 735

Pro Asn Gly Ile Cys Glu Asn Leu Arg Gly Thr Tyr Lys Cys Ile Cys
            740                 745                 750

Asn Ser Gly Tyr Glu Val Asp Ile Thr Gly Lys Asn Cys Val Asp Ile
            755                 760                 765

Asn Glu Cys Val Leu Asn Ser Leu Leu Cys Asp Asn Gly Gln Cys Arg
770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
            805                 810                 815

Pro Cys Ile Asn Gly Val Cys Lys Asn Ser Pro Gly Ser Phe Ile Cys
            820                 825                 830

Glu Cys Ser Pro Glu Ser Thr Leu Asp Pro Thr Lys Thr Ile Cys Ile
            835                 840                 845

Glu Thr Ile Lys Gly Thr Cys Trp Gln Thr Val Ile Asp Gly Arg Cys
850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
            885                 890                 895

Ile Cys Gly Lys Gly Phe Ser Arg Ile Lys Gly Thr Gln Cys Glu Asp
            900                 905                 910

Ile Asn Glu Cys Glu Val Phe Pro Gly Val Cys Lys Asn Gly Leu Cys
            915                 920                 925

Val Asn Ser Arg Gly Ser Phe Lys Cys Glu Cys Pro Asn Gly Met Thr
930                 935                 940

Leu Asp Ala Thr Gly Arg Ile Cys Leu Asp Ile Arg Leu Glu Thr Cys
945                 950                 955                 960

Phe Leu Lys Tyr Asp Asp Glu Glu Cys Thr Leu Pro Ile Ala Gly Arg
            965                 970                 975

His Arg Met Asp Ala Cys Cys Cys Ser Val Gly Ala Ala Trp Gly Thr
            980                 985                 990

Glu Glu Cys Glu Glu Cys Pro Leu Arg Asn Ser Arg Glu Tyr Glu Glu
            995                 1000                1005

Leu Cys Pro Arg Gly Pro Gly Phe Ala Thr Lys Asp Ile Thr Asn
       1010                1015                1020

Gly Lys Pro Phe Phe Lys Asp Ile Asn Glu Cys Lys Met Ile Pro
     1025                1030                1035

Ser Leu Cys Thr His Gly Lys Cys Arg Asn Thr Ile Gly Ser Phe
```

```
              1040            1045            1050
Lys Cys Arg Cys Asp Ser Gly Phe Ala Leu Asp Ser Glu Glu Arg
    1055            1060            1065
Asn Cys Thr Asp Ile Asp Glu Cys Arg Ile Ser Pro Asp Leu Cys
    1070            1075            1080
Gly Arg Gly Gln Cys Val Asn Thr Pro Gly Asp Phe Glu Cys Lys
    1085            1090            1095
Cys Asp Glu Gly Tyr Glu Ser Gly Phe Met Met Met Lys Asn Cys
    1100            1105            1110
Met Asp Ile Asp Glu Cys Gln Arg Asp Pro Leu Leu Cys Arg Gly
    1115            1120            1125
Gly Ile Cys His Asn Thr Glu Gly Ser Tyr Arg Cys Glu Cys Pro
    1130            1135            1140
Pro Gly His Gln Leu Ser Pro Asn Ile Ser Ala Cys Ile Asp Ile
    1145            1150            1155
Asn Glu Cys Glu Leu Ser Ala Asn Leu Cys Pro His Gly Arg Cys
    1160            1165            1170
Val Asn Leu Ile Gly Lys Tyr Gln Cys Ala Cys Asn Pro Gly Tyr
    1175            1180            1185
His Pro Thr His Asp Arg Leu Phe Cys Val Asp Ile Asp Glu Cys
    1190            1195            1200
Ser Ile Met Asn Gly Gly Cys Glu Thr Phe Cys Thr Asn Ser Asp
    1205            1210            1215
Gly Ser Tyr Glu Cys Ser Cys Gln Pro Gly Phe Ala Leu Met Pro
    1220            1225            1230
Asp Gln Arg Ser Cys Thr Asp Ile Asp Glu Cys Glu Asp Asn Pro
    1235            1240            1245
Asn Ile Cys Asp Gly Gly Gln Cys Thr Asn Ile Pro Gly Glu Tyr
    1250            1255            1260
Arg Cys Leu Cys Tyr Asp Gly Phe Met Ala Ser Glu Asp Met Lys
    1265            1270            1275
Thr Cys Val Asp Val Asn Glu Cys Asp Leu Asn Pro Asn Ile Cys
    1280            1285            1290
Leu Ser Gly Thr Cys Glu Asn Thr Lys Gly Ser Phe Ile Cys His
    1295            1300            1305
Cys Asp Met Gly Tyr Ser Gly Lys Lys Gly Lys Thr Gly Cys Thr
    1310            1315            1320
Asp Ile Asn Glu Cys Glu Ile Gly Ala His Asn Cys Gly Arg His
    1325            1330            1335
Ala Val Cys Thr Asn Thr Ala Gly Ser Phe Lys Cys Ser Cys Ser
    1340            1345            1350
Pro Gly Trp Ile Gly Asp Gly Ile Lys Cys Thr Asp Leu Asp Glu
    1355            1360            1365
Cys Ser Asn Gly Thr His Met Cys Ser Gln His Ala Asp Cys Lys
    1370            1375            1380
Asn Thr Met Gly Ser Tyr Arg Cys Leu Cys Lys Asp Gly Tyr Thr
    1385            1390            1395
Gly Asp Gly Phe Thr Cys Thr Asp Leu Asp Glu Cys Ser Glu Asn
    1400            1405            1410
Leu Asn Leu Cys Gly Asn Gly Gln Cys Leu Asn Ala Pro Gly Gly
    1415            1420            1425
Tyr Arg Cys Glu Cys Asp Met Gly Phe Val Pro Ser Ala Asp Gly
    1430            1435            1440
```

-continued

```
Lys Ala Cys Glu Asp Ile Asp Glu Cys Ser Leu Pro Asn Ile Cys
1445            1450                1455

Val Phe Gly Thr Cys His Asn Leu Pro Gly Leu Phe Arg Cys Glu
1460            1465                1470

Cys Glu Ile Gly Tyr Glu Leu Asp Arg Ser Gly Gly Asn Cys Thr
1475            1480                1485

Asp Val Asn Glu Cys Leu Asp Pro Thr Thr Cys Ile Ser Gly Asn
1490            1495                1500

Cys Val Asn Thr Pro Gly Ser Tyr Thr Cys Asp Cys Pro Pro Asp
1505            1510                1515

Phe Glu Leu Asn Pro Thr Arg Val Gly Cys Val Asp Thr Arg Ser
1520            1525                1530

Gly Asn Cys Tyr Leu Asp Ile Arg Pro Arg Gly Asp Asn Gly Asp
1535            1540                1545

Thr Ala Cys Ser Asn Glu Ile Gly Val Gly Val Ser Lys Ala Ser
1550            1555                1560

Cys Cys Cys Ser Leu Gly Lys Ala Trp Gly Thr Pro Cys Glu Leu
1565            1570                1575

Cys Pro Ser Val Asn Thr Ser Glu Tyr Lys Ile Leu Cys Pro Gly
1580            1585                1590

Gly Glu Gly Phe Arg Pro Asn Pro Ile Thr Val Ile Leu Glu Asp
1595            1600                1605

Ile Asp Glu Cys Gln Glu Leu Pro Gly Leu Cys Gln Gly Gly Lys
1610            1615                1620

Cys Ile Asn Thr Phe Gly Ser Phe Gln Cys Arg Cys Pro Thr Gly
1625            1630                1635

Tyr Tyr Leu Asn Glu Asp Thr Arg Val Cys Asp Asp Val Asn Glu
1640            1645                1650

Cys Glu Thr Pro Gly Ile Cys Gly Pro Gly Thr Cys Tyr Asn Thr
1655            1660                1665

Val Gly Asn Tyr Thr Cys Ile Cys Pro Pro Asp Tyr Met Gln Val
1670            1675                1680

Asn Gly Gly Asn Asn Cys Met Asp Met Arg Arg Ser Leu Cys Tyr
1685            1690                1695

Arg Asn Tyr Tyr Ala Asp Asn Gln Thr Cys Asp Gly Glu Leu Leu
1700            1705                1710

Phe Asn Met Thr Lys Lys Met Cys Cys Cys Ser Tyr Asn Ile Gly
1715            1720                1725

Arg Ala Trp Asn Lys Pro Cys Glu Gln Cys Pro Ile Pro Ser Thr
1730            1735                1740

Asp Glu Phe Ala Thr Leu Cys Gly Ser Gln Arg Pro Gly Phe Val
1745            1750                1755

Ile Asp Ile Tyr Thr Gly Leu Pro Val Asp Ile Asp Glu Cys Arg
1760            1765                1770

Glu Ile Pro Gly Val Cys Glu Asn Gly Val Cys Ile Asn Met Val
1775            1780                1785

Gly Ser Phe Arg Cys Glu Cys Pro Val Gly Phe Phe Tyr Asn Asp
1790            1795                1800

Lys Leu Leu Val Cys Glu Asp Ile Asp Glu Cys Gln Asn Gly Pro
1805            1810                1815

Val Cys Gln Arg Asn Ala Glu Cys Ile Asn Thr Ala Gly Ser Tyr
1820            1825                1830
```

```
Arg Cys Asp Cys Lys Pro Gly Tyr Arg Leu Thr Ser Thr Gly Gln
1835                1840                1845

Cys Asn Asp Arg Asn Glu Cys Gln Glu Ile Pro Asn Ile Cys Ser
1850                1855                1860

His Gly Gln Cys Ile Asp Thr Val Gly Ser Phe Tyr Cys Leu Cys
1865                1870                1875

His Thr Gly Phe Lys Thr Asn Val Asp Gln Thr Met Cys Leu Asp
1880                1885                1890

Ile Asn Glu Cys Glu Arg Asp Ala Cys Gly Asn Gly Thr Cys Arg
1895                1900                1905

Asn Thr Ile Gly Ser Phe Asn Cys Arg Cys Asn His Gly Phe Ile
1910                1915                1920

Leu Ser His Asn Asn Asp Cys Ile Asp Val Asp Glu Cys Ala Thr
1925                1930                1935

Gly Asn Gly Asn Leu Cys Arg Asn Gly Gln Cys Val Asn Thr Val
1940                1945                1950

Gly Ser Phe Gln Cys Arg Cys Asn Glu Gly Tyr Glu Val Ala Pro
1955                1960                1965

Asp Gly Arg Thr Cys Val Asp Ile Asn Glu Cys Val Leu Asp Pro
1970                1975                1980

Gly Lys Cys Ala Pro Gly Thr Cys Gln Asn Leu Asp Gly Ser Tyr
1985                1990                1995

Arg Cys Ile Cys Pro Pro Gly Tyr Ser Leu Gln Asn Asp Lys Cys
2000                2005                2010

Glu Asp Ile Asp Glu Cys Val Glu Glu Pro Glu Ile Cys Ala Leu
2015                2020                2025

Gly Thr Cys Ser Asn Thr Glu Gly Ser Phe Lys Cys Leu Cys Pro
2030                2035                2040

Glu Gly Phe Ser Leu Ser Ser Thr Gly Arg Arg Cys Gln Asp Leu
2045                2050                2055

Arg Met Ser Tyr Cys Tyr Ala Lys Phe Glu Gly Gly Lys Cys Ser
2060                2065                2070

Ser Pro Lys Ser Arg Asn His Ser Lys Gln Glu Cys Cys Cys Ala
2075                2080                2085

Leu Lys Gly Glu Gly Trp Gly Asp Pro Cys Glu Leu Cys Pro Thr
2090                2095                2100

Glu Pro Asp Glu Ala Phe Arg Gln Ile Cys Pro Phe Gly Ser Gly
2105                2110                2115

Ile Ile Val Gly Pro Asp Asp Ser Ala Val Asp Met Asp Glu Cys
2120                2125                2130

Lys Glu Pro Asp Val Cys Arg His Gly Gln Cys Ile Asn Thr Asp
2135                2140                2145

Gly Ser Tyr Arg Cys Glu Cys Pro Phe Gly Tyr Ile Leu Glu Gly
2150                2155                2160

Asn Glu Cys Val Asp Thr Asp Glu Cys Ser Val Gly Asn Pro Cys
2165                2170                2175

Gly Asn Gly Thr Cys Lys Asn Val Ile Gly Gly Phe Glu Cys Thr
2180                2185                2190

Cys Glu Glu Gly Phe Glu Pro Gly Pro Met Met Thr Cys Glu Asp
2195                2200                2205

Ile Asn Glu Cys Ala Gln Asn Pro Leu Leu Cys Ala Phe Arg Cys
2210                2215                2220

Val Asn Thr Tyr Gly Ser Tyr Glu Cys Lys Cys Pro Val Gly Tyr
```

```
            2225                2230                2235

Val Leu Arg Glu Asp Arg Arg Met Cys Lys Asp Glu Asp Glu Cys
            2240                2245                2250

Ala Glu Gly Lys His Asp Cys Thr Glu Lys Gln Met Glu Cys Lys
            2255                2260                2265

Asn Leu Ile Gly Thr Tyr Met Cys Ile Cys Gly Pro Gly Tyr Gln
            2270                2275                2280

Arg Arg Pro Asp Gly Glu Gly Cys Ile Asp Glu Asn Glu Cys Gln
            2285                2290                2295

Thr Lys Pro Gly Ile Cys Glu Asn Gly Arg Cys Leu Asn Thr Leu
            2300                2305                2310

Gly Ser Tyr Thr Cys Glu Cys Asn Asp Gly Phe Thr Ala Ser Pro
            2315                2320                2325

Thr Gln Asp Glu Cys Leu Asp Asn Arg Glu Gly Tyr Cys Phe Ser
            2330                2335                2340

Glu Val Leu Gln Asn Met Cys Gln Ile Gly Ser Ser Asn Arg Asn
            2345                2350                2355

Pro Val Thr Lys Ser Glu Cys Cys Asp Gly Gly Arg Gly Trp
            2360                2365                2370

Gly Pro His Cys Glu Ile Cys Pro Phe Glu Gly Thr Val Ala Tyr
            2375                2380                2385

Lys Lys Leu Cys Pro His Gly Arg Gly Phe Met Thr Asn Gly Ala
            2390                2395                2400

Asp Ile Asp Glu Cys Lys Val Ile His Asp Val Cys Arg Asn Gly
            2405                2410                2415

Glu Cys Val Asn Asp Arg Gly Ser Tyr His Cys Ile Cys Lys Thr
            2420                2425                2430

Gly Tyr Thr Pro Asp Ile Thr Gly Thr Ala Cys Val Asp Leu Asn
            2435                2440                2445

Glu Cys Asn Gln Ala Pro Lys Pro Cys Asn Phe Ile Cys Lys Asn
            2450                2455                2460

Thr Glu Gly Ser Tyr Gln Cys Ser Cys Pro Lys Gly Tyr Ile Leu
            2465                2470                2475

Gln Glu Asp Gly Arg Ser Cys Lys Asp Leu Asp Glu Cys Ala Thr
            2480                2485                2490

Lys Gln His Asn Cys Gln Phe Leu Cys Val Asn Thr Ile Gly Gly
            2495                2500                2505

Phe Thr Cys Lys Cys Pro Pro Gly Phe Thr Gln His His Thr Ala
            2510                2515                2520

Cys Ile Asp Asn Asn Glu Cys Thr Ser Asp Ile Asn Leu Cys Gly
            2525                2530                2535

Ser Lys Gly Val Cys Gln Asn Thr Pro Gly Ser Phe Thr Cys Glu
            2540                2545                2550

Cys Gln Arg Gly Phe Ser Leu Asp Gln Ser Gly Ala Ser Cys Glu
            2555                2560                2565

Asp Val Asp Glu Cys Glu Gly Asn His Arg Cys Gln His Gly Cys
            2570                2575                2580

Gln Asn Ile Ile Gly Gly Tyr Arg Cys Ser Cys Pro Gln Gly Tyr
            2585                2590                2595

Leu Gln His Tyr Gln Trp Asn Gln Cys Val Asp Glu Asn Glu Cys
            2600                2605                2610

Leu Ser Ala His Val Cys Gly Gly Ala Ser Cys His Asn Thr Leu
            2615                2620                2625
```

Gly Ser Tyr Lys Cys Met Cys Pro Thr Gly Phe Gln Tyr Glu Gln
                2630                2635                2640

Phe Ser Gly Gly Cys Gln Asp Ile Asn Glu Cys Gly Ser Ser Gln
        2645                2650                2655

Ala Pro Cys Ser Tyr Gly Cys Ser Asn Thr Glu Gly Gly Tyr Leu
    2660                2665                2670

Cys Gly Cys Pro Pro Gly Tyr Phe Arg Ile Gly Gln Gly His Cys
2675                2680                2685

Val Ser Gly Met Gly Met Gly Arg Gly Gly Pro Glu Pro Pro Ala
    2690                2695                2700

Ser Ser Glu Met Asp Asp Asn Ser Leu Ser Pro Glu Ala Cys Tyr
    2705                2710                2715

Glu Cys Lys Ile Asn Gly Tyr Pro Lys Arg Gly Arg Lys Arg Arg
    2720                2725                2730

Ser Thr Asn Glu Thr Asp Ala Ser Asp Ile Gln Asp Gly Ser Glu
    2735                2740                2745

Met Glu Ala Asn Val Ser Leu Ala Ser Trp Asp Val Glu Lys Pro
    2750                2755                2760

Ala Ser Phe Ala Phe Asn Ile Ser His Val Asn Asn Lys Val Arg
    2765                2770                2775

Ile Leu Glu Leu Leu Pro Ala Leu Thr Thr Leu Met Asn His Asn
    2780                2785                2790

Arg Tyr Leu Ile Glu Ser Gly Asn Glu Asp Gly Phe Phe Lys Ile
    2795                2800                2805

Asn Gln Lys Glu Gly Val Ser Tyr Leu His Phe Thr Lys Lys Lys
    2810                2815                2820

Pro Val Ala Gly Thr Tyr Ser Leu Gln Ile Ser Ser Thr Pro Leu
    2825                2830                2835

Tyr Lys Lys Lys Glu Leu Asn Gln Leu Glu Asp Arg Tyr Asp Lys
    2840                2845                2850

Asp Tyr Leu Ser Gly Glu Leu Gly Asp Asn Leu Lys Met Lys Ile
    2855                2860                2865

Gln Ile Leu Leu His
    2870

<210> SEQ ID NO 31
<211> LENGTH: 2738
<212> TYPE: PRT
<213> ORGANISM: Artificial Sequence
<220> FEATURE:
<223> OTHER INFORMATION: Synthetic

<400> SEQUENCE: 31

Met Arg Arg Gly Gly Leu Leu Glu Val Ala Leu Ala Phe Ala Leu Leu
1               5                   10                  15

Leu Glu Ser Tyr Thr Ser His Gly Ala Asp Ala Asn Leu Glu Ala Gly
                20                  25                  30

Ser Leu Lys Glu Thr Arg Ala Asn Arg Ala Lys Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

```
Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
            115                 120                 125

Cys Ser Asp Asp His Cys Leu Cys Gln Lys Gly Tyr Ile Gly Thr His
            130                 135                 140

Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
                165                 170                 175

Cys Glu Arg Asp Tyr Arg Thr Gly Pro Cys Phe Thr Val Val Ser Asn
            180                 185                 190

Gln Met Cys Gln Gly Gln Leu Ser Gly Ile Val Cys Thr Lys Thr Leu
            195                 200                 205

Cys Cys Ala Thr Val Gly Arg Ala Trp Gly His Pro Cys Glu Met Cys
            210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
            245                 250                 255

Cys Gln Gly Gly Asn Cys Ile Asn Thr Val Gly Ser Phe Glu Cys Lys
            260                 265                 270

Cys Pro Ala Gly His Lys Phe Asn Glu Val Ser Gln Lys Cys Glu Asp
            275                 280                 285

Ile Asp Glu Cys Ser Thr Ile Pro Gly Val Cys Asp Gly Gly Glu Cys
            290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
            325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
            355                 360                 365

Gly Val Thr Val Ala Pro Glu Met Cys Pro Ile Arg Ser Thr Glu Asp
            370                 375                 380

Phe Asn Lys Leu Cys Ser Val Pro Leu Val Ile Pro Gly Arg Pro Glu
385                 390                 395                 400

Tyr Pro Pro Pro Ile Gly Pro Leu Pro Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
            435                 440                 445

Phe Asn Val Thr Asp Tyr Cys Gln Leu Val Arg Tyr Leu Cys Gln Asn
450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
            500                 505                 510
```

```
Tyr Thr Cys His Cys Arg Ala Gly Tyr Gln Ser Thr Leu Thr Arg Thr
            515                 520                 525

Glu Cys Arg Asp Ile Asp Glu Cys Leu Gln Asn Gly Arg Ile Cys Asn
        530                 535                 540

Asn Gly Arg Cys Ile Asn Thr Asp Gly Ser Phe His Cys Val Cys Asn
545                 550                 555                 560

Ala Gly Phe His Val Thr Arg Asp Gly Lys Asn Cys Glu Asp Met Asp
                565                 570                 575

Glu Cys Ser Ile Arg Asn Met Cys Leu Asn Gly Met Cys Ile Asn Glu
            580                 585                 590

Asp Gly Ser Phe Lys Cys Ile Cys Lys Pro Gly Phe Gln Leu Ala Ser
            595                 600                 605

Asp Gly Arg Tyr Cys Lys Asp Ile Asn Glu Cys Glu Thr Pro Gly Ile
        610                 615                 620

Cys Met Asn Gly Arg Cys Val Asn Thr Asp Gly Ser Tyr Arg Cys Glu
625                 630                 635                 640

Cys Phe Pro Gly Leu Ala Val Gly Leu Asp Gly Arg Val Cys Val Asp
                645                 650                 655

Thr His Met Arg Ser Thr Cys Tyr Gly Gly Tyr Arg Arg Gly Gln Cys
            660                 665                 670

Val Lys Pro Leu Phe Gly Ala Val Thr Lys Ser Glu Cys Cys Cys Ala
            675                 680                 685

Ser Thr Glu Tyr Ala Phe Gly Glu Pro Cys Gln Pro Cys Pro Ala Gln
            690                 695                 700

Asn Ser Ala Glu Tyr Gln Ala Leu Cys Ser Ser Gly Pro Gly Met Thr
705                 710                 715                 720

Ser Ala Gly Thr Asp Ile Asn Glu Cys Ala Leu Asp Pro Asp Ile Cys
                725                 730                 735

Pro Asn Gly Ile Cys Glu Asn Leu Arg Gly Thr Tyr Lys Cys Ile Cys
                740                 745                 750

Asn Ser Gly Tyr Glu Val Asp Ile Thr Gly Lys Asn Cys Val Asp Ile
            755                 760                 765

Asn Glu Cys Val Leu Asn Ser Leu Leu Cys Asp Asn Gly Gln Cys Arg
770                 775                 780

Asn Thr Pro Gly Ser Phe Val Cys Thr Cys Pro Lys Gly Phe Val Tyr
785                 790                 795                 800

Lys Pro Asp Leu Lys Thr Cys Glu Asp Ile Asp Glu Cys Glu Ser Ser
                805                 810                 815

Pro Cys Ile Asn Gly Val Cys Lys Asn Ser Pro Gly Ser Phe Ile Cys
                820                 825                 830

Glu Cys Ser Pro Glu Ser Thr Leu Asp Pro Thr Lys Thr Ile Cys Ile
            835                 840                 845

Glu Thr Ile Lys Gly Thr Cys Trp Gln Thr Val Ile Asp Gly Arg Cys
            850                 855                 860

Glu Ile Asn Ile Asn Gly Ala Thr Leu Lys Ser Glu Cys Cys Ser Ser
865                 870                 875                 880

Leu Gly Ala Ala Trp Gly Ser Pro Cys Thr Ile Cys Gln Leu Asp Pro
                885                 890                 895

Ile Cys Gly Lys Gly Phe Ser Arg Ile Lys Gly Thr Gln Cys Glu Asp
                900                 905                 910

Ile Asn Glu Cys Glu Val Phe Pro Gly Val Cys Lys Asn Gly Leu Cys
            915                 920                 925

Val Asn Ser Arg Gly Ser Phe Lys Cys Glu Cys Pro Asn Gly Met Thr
```

```
                930             935             940
Leu Asp Ala Thr Gly Arg Ile Cys Leu Asp Ile Arg Leu Glu Thr Cys
945                 950             955                 960

Phe Leu Lys Tyr Asp Asp Glu Glu Cys Thr Leu Pro Ile Ala Gly Arg
                965             970             975

His Arg Met Asp Ala Cys Cys Ser Val Gly Ala Ala Trp Gly Thr
            980             985             990

Glu Glu Cys Glu Glu Cys Pro Leu Arg Asn Ser Arg Glu Tyr Glu Glu
        995             1000            1005

Leu Cys Pro Arg Gly Pro Gly Phe Ala Thr Lys Asp Ile Thr Asn
    1010            1015            1020

Gly Lys Pro Phe Phe Lys Asp Ile Asn Glu Cys Lys Met Ile Pro
    1025            1030            1035

Ser Leu Cys Thr His Gly Lys Cys Arg Asn Thr Ile Gly Ser Phe
    1040            1045            1050

Lys Cys Arg Cys Asp Ser Gly Phe Ala Leu Asp Ser Glu Glu Arg
    1055            1060            1065

Asn Cys Thr Asp Ile Asp Glu Cys Arg Ile Ser Pro Asp Leu Cys
    1070            1075            1080

Gly Arg Gly Gln Cys Val Asn Thr Pro Gly Asp Phe Glu Cys Lys
    1085            1090            1095

Cys Asp Glu Gly Tyr Glu Ser Gly Phe Met Met Met Lys Asn Cys
    1100            1105            1110

Met Asp Ile Asp Glu Cys Gln Arg Asp Pro Leu Leu Cys Arg Gly
    1115            1120            1125

Gly Ile Cys His Asn Thr Glu Gly Ser Tyr Arg Cys Glu Cys Pro
    1130            1135            1140

Pro Gly His Gln Leu Ser Pro Asn Ile Ser Ala Cys Ile Asp Ile
    1145            1150            1155

Asn Glu Cys Glu Leu Ser Ala Asn Leu Cys Pro His Gly Arg Cys
    1160            1165            1170

Val Asn Leu Ile Gly Lys Tyr Gln Cys Ala Cys Asn Pro Gly Tyr
    1175            1180            1185

His Pro Thr His Asp Arg Leu Phe Cys Val Asp Ile Asp Glu Cys
    1190            1195            1200

Ser Ile Met Asn Gly Gly Cys Glu Thr Phe Cys Thr Asn Ser Asp
    1205            1210            1215

Gly Ser Tyr Glu Cys Ser Cys Gln Pro Gly Phe Ala Leu Met Pro
    1220            1225            1230

Asp Gln Arg Ser Cys Thr Asp Ile Asp Glu Cys Glu Asp Asn Pro
    1235            1240            1245

Asn Ile Cys Asp Gly Gly Gln Cys Thr Asn Ile Pro Gly Glu Tyr
    1250            1255            1260

Arg Cys Leu Cys Tyr Asp Gly Phe Met Ala Ser Glu Asp Met Lys
    1265            1270            1275

Thr Cys Val Asp Val Asn Glu Cys Asp Leu Asn Pro Asn Ile Cys
    1280            1285            1290

Leu Ser Gly Thr Cys Glu Asn Thr Lys Gly Ser Phe Ile Cys His
    1295            1300            1305

Cys Asp Met Gly Tyr Ser Gly Lys Lys Gly Lys Thr Gly Cys Thr
    1310            1315            1320

Asp Ile Asn Glu Cys Glu Ile Gly Ala His Asn Cys Gly Arg His
    1325            1330            1335
```

```
Ala Val Cys Thr Asn Thr Ala Gly Ser Phe Lys Cys Ser Cys Ser
1340                1345                1350

Pro Gly Trp Ile Gly Asp Gly Ile Lys Cys Thr Asp Leu Asp Glu
1355                1360                1365

Cys Ser Asn Gly Thr His Met Cys Ser Gln His Ala Asp Cys Lys
1370                1375                1380

Asn Thr Met Gly Ser Tyr Arg Cys Leu Cys Lys Asp Gly Tyr Thr
1385                1390                1395

Gly Asp Gly Phe Thr Cys Thr Asp Leu Asp Glu Cys Ser Glu Asn
1400                1405                1410

Leu Asn Leu Cys Gly Asn Gly Gln Cys Leu Asn Ala Pro Gly Gly
1415                1420                1425

Tyr Arg Cys Glu Cys Asp Met Gly Phe Val Pro Ser Ala Asp Gly
1430                1435                1440

Lys Ala Cys Glu Asp Ile Asp Glu Cys Ser Leu Pro Asn Ile Cys
1445                1450                1455

Val Phe Gly Thr Cys His Asn Leu Pro Gly Leu Phe Arg Cys Glu
1460                1465                1470

Cys Glu Ile Gly Tyr Glu Leu Asp Arg Ser Gly Gly Asn Cys Thr
1475                1480                1485

Asp Val Asn Glu Cys Leu Asp Pro Thr Thr Cys Ile Ser Gly Asn
1490                1495                1500

Cys Val Asn Thr Pro Gly Ser Tyr Thr Cys Asp Cys Pro Pro Asp
1505                1510                1515

Phe Glu Leu Asn Pro Thr Arg Val Gly Cys Val Asp Thr Arg Ser
1520                1525                1530

Gly Asn Cys Tyr Leu Asp Ile Arg Pro Arg Gly Asp Asn Gly Asp
1535                1540                1545

Thr Ala Cys Ser Asn Glu Ile Gly Val Gly Val Ser Lys Ala Ser
1550                1555                1560

Cys Cys Cys Ser Leu Gly Lys Ala Trp Gly Thr Pro Cys Glu Leu
1565                1570                1575

Cys Pro Ser Val Asn Thr Ser Glu Tyr Lys Ile Leu Cys Pro Gly
1580                1585                1590

Gly Glu Gly Phe Arg Pro Asn Pro Ile Thr Val Ile Leu Glu Asp
1595                1600                1605

Ile Asp Glu Cys Gln Glu Leu Pro Gly Leu Cys Gln Gly Gly Lys
1610                1615                1620

Cys Ile Asn Thr Phe Gly Ser Phe Gln Cys Arg Cys Pro Thr Gly
1625                1630                1635

Tyr Tyr Leu Asn Glu Asp Thr Arg Val Cys Asp Asp Val Asn Glu
1640                1645                1650

Cys Glu Thr Pro Gly Ile Cys Gly Pro Gly Thr Cys Tyr Asn Thr
1655                1660                1665

Val Gly Asn Tyr Thr Cys Ile Cys Pro Pro Asp Tyr Met Gln Val
1670                1675                1680

Asn Gly Gly Asn Asn Cys Met Asp Met Arg Arg Ser Leu Cys Tyr
1685                1690                1695

Arg Asn Tyr Tyr Ala Asp Asn Gln Thr Cys Asp Gly Glu Leu Leu
1700                1705                1710

Phe Asn Met Thr Lys Lys Met Cys Cys Cys Ser Tyr Asn Ile Gly
1715                1720                1725
```

```
Arg Ala Trp Asn Lys Pro Cys Glu Gln Cys Pro Ile Pro Ser Thr
1730             1735             1740

Asp Glu Phe Ala Thr Leu Cys Gly Ser Gln Arg Pro Gly Phe Val
1745             1750             1755

Ile Asp Ile Tyr Thr Gly Leu Pro Val Asp Ile Asp Glu Cys Arg
1760             1765             1770

Glu Ile Pro Gly Val Cys Glu Asn Gly Val Cys Ile Asn Met Val
1775             1780             1785

Gly Ser Phe Arg Cys Glu Cys Pro Val Gly Phe Phe Tyr Asn Asp
1790             1795             1800

Lys Leu Leu Val Cys Glu Asp Ile Asp Glu Cys Gln Asn Gly Pro
1805             1810             1815

Val Cys Gln Arg Asn Ala Glu Cys Ile Asn Thr Ala Gly Ser Tyr
1820             1825             1830

Arg Cys Asp Cys Lys Pro Gly Tyr Arg Leu Thr Ser Thr Gly Gln
1835             1840             1845

Cys Asn Asp Arg Asn Glu Cys Gln Glu Ile Pro Asn Ile Cys Ser
1850             1855             1860

His Gly Gln Cys Ile Asp Thr Val Gly Ser Phe Tyr Cys Leu Cys
1865             1870             1875

His Thr Gly Phe Lys Thr Asn Val Asp Gln Thr Met Cys Leu Asp
1880             1885             1890

Ile Asn Glu Cys Glu Arg Asp Ala Cys Gly Asn Gly Thr Cys Arg
1895             1900             1905

Asn Thr Ile Gly Ser Phe Asn Cys Arg Cys Asn His Gly Phe Ile
1910             1915             1920

Leu Ser His Asn Asn Asp Cys Ile Asp Val Asp Glu Cys Ala Thr
1925             1930             1935

Gly Asn Gly Asn Leu Cys Arg Asn Gly Gln Cys Val Asn Thr Val
1940             1945             1950

Gly Ser Phe Gln Cys Arg Cys Asn Glu Gly Tyr Glu Val Ala Pro
1955             1960             1965

Asp Gly Arg Thr Cys Val Asp Ile Asn Glu Cys Val Leu Asp Pro
1970             1975             1980

Gly Lys Cys Ala Pro Gly Thr Cys Gln Asn Leu Asp Gly Ser Tyr
1985             1990             1995

Arg Cys Ile Cys Pro Pro Gly Tyr Ser Leu Gln Asn Asp Lys Cys
2000             2005             2010

Glu Asp Ile Asp Glu Cys Val Glu Glu Pro Glu Ile Cys Ala Leu
2015             2020             2025

Gly Thr Cys Ser Asn Thr Glu Gly Ser Phe Lys Cys Leu Cys Pro
2030             2035             2040

Glu Gly Phe Ser Leu Ser Ser Thr Gly Arg Arg Cys Gln Asp Leu
2045             2050             2055

Arg Met Ser Tyr Cys Tyr Ala Lys Phe Glu Gly Gly Lys Cys Ser
2060             2065             2070

Ser Pro Lys Ser Arg Asn His Ser Lys Gln Glu Cys Cys Cys Ala
2075             2080             2085

Leu Lys Gly Glu Gly Trp Gly Asp Pro Cys Glu Leu Cys Pro Thr
2090             2095             2100

Glu Pro Asp Glu Ala Phe Arg Gln Ile Cys Pro Phe Gly Ser Gly
2105             2110             2115

Ile Ile Val Gly Pro Asp Asp Ser Ala Val Asp Met Asp Glu Cys
```

```
                   2120             2125             2130
Lys Glu Pro Asp Val Cys Arg His Gly Gln Cys Ile Asn Thr Asp
    2135             2140             2145
Gly Ser Tyr Arg Cys Glu Cys Pro Phe Gly Tyr Ile Leu Glu Gly
    2150             2155             2160
Asn Glu Cys Val Asp Thr Asp Glu Cys Ser Val Gly Asn Pro Cys
    2165             2170             2175
Gly Asn Gly Thr Cys Lys Asn Val Ile Gly Gly Phe Glu Cys Thr
    2180             2185             2190
Cys Glu Glu Gly Phe Glu Pro Gly Pro Met Met Thr Cys Glu Asp
    2195             2200             2205
Ile Asn Glu Cys Ala Gln Asn Pro Leu Leu Cys Ala Phe Arg Cys
    2210             2215             2220
Val Asn Thr Tyr Gly Ser Tyr Glu Cys Lys Cys Pro Val Gly Tyr
    2225             2230             2235
Val Leu Arg Glu Asp Arg Arg Met Cys Lys Asp Glu Asp Glu Cys
    2240             2245             2250
Ala Glu Gly Lys His Asp Cys Thr Glu Lys Gln Met Glu Cys Lys
    2255             2260             2265
Asn Leu Ile Gly Thr Tyr Met Cys Ile Cys Gly Pro Gly Tyr Gln
    2270             2275             2280
Arg Arg Pro Asp Gly Glu Gly Cys Ile Asp Glu Asn Glu Cys Gln
    2285             2290             2295
Thr Lys Pro Gly Ile Cys Glu Asn Gly Arg Cys Leu Asn Thr Leu
    2300             2305             2310
Gly Ser Tyr Thr Cys Glu Cys Asn Asp Gly Phe Thr Ala Ser Pro
    2315             2320             2325
Thr Gln Asp Glu Cys Leu Asp Asn Arg Glu Gly Tyr Cys Phe Ser
    2330             2335             2340
Glu Val Leu Gln Asn Met Cys Gln Ile Gly Ser Ser Asn Arg Asn
    2345             2350             2355
Pro Val Thr Lys Ser Glu Cys Cys Asp Gly Gly Arg Gly Trp
    2360             2365             2370
Gly Pro His Cys Glu Ile Cys Pro Phe Glu Gly Thr Val Ala Tyr
    2375             2380             2385
Lys Lys Leu Cys Pro His Gly Arg Gly Phe Met Thr Asn Gly Ala
    2390             2395             2400
Asp Ile Asp Glu Cys Lys Val Ile His Asp Val Cys Arg Asn Gly
    2405             2410             2415
Glu Cys Val Asn Asp Arg Gly Ser Tyr His Cys Ile Cys Lys Thr
    2420             2425             2430
Gly Tyr Thr Pro Asp Ile Thr Gly Thr Ala Cys Val Asp Leu Asn
    2435             2440             2445
Glu Cys Asn Gln Ala Pro Lys Pro Cys Asn Phe Ile Cys Lys Asn
    2450             2455             2460
Thr Glu Gly Ser Tyr Gln Cys Ser Cys Pro Lys Gly Tyr Ile Leu
    2465             2470             2475
Gln Glu Asp Gly Arg Ser Cys Lys Asp Leu Asp Glu Cys Ala Thr
    2480             2485             2490
Lys Gln His Asn Cys Gln Phe Leu Cys Val Asn Thr Ile Gly Gly
    2495             2500             2505
Phe Thr Cys Lys Cys Pro Pro Gly Phe Thr Gln His His Thr Ala
    2510             2515             2520
```

-continued

```
Cys Ile Asp Asn Asn Glu Cys Thr Ser Asp Ile Asn Leu Cys Gly
    2525                2530                2535

Ser Lys Gly Val Cys Gln Asn Thr Pro Gly Ser Phe Thr Cys Glu
    2540                2545                2550

Cys Gln Arg Gly Phe Ser Leu Asp Gln Ser Gly Ala Ser Cys Glu
    2555                2560                2565

Asp Val Asp Glu Cys Glu Gly Asn His Arg Cys Gln His Gly Cys
    2570                2575                2580

Gln Asn Ile Ile Gly Gly Tyr Arg Cys Ser Cys Pro Gln Gly Tyr
    2585                2590                2595

Leu Gln His Tyr Gln Trp Asn Gln Cys Val Asp Glu Asn Glu Cys
    2600                2605                2610

Leu Ser Ala His Val Cys Gly Gly Ala Ser Cys His Asn Thr Leu
    2615                2620                2625

Gly Ser Tyr Lys Cys Met Cys Pro Thr Gly Phe Gln Tyr Glu Gln
    2630                2635                2640

Phe Ser Gly Gly Cys Gln Asp Ile Asn Glu Cys Gly Ser Ser Gln
    2645                2650                2655

Ala Pro Cys Ser Tyr Gly Cys Ser Asn Thr Glu Gly Gly Tyr Leu
    2660                2665                2670

Cys Gly Cys Pro Pro Gly Tyr Phe Arg Ile Gly Gln Gly His Cys
    2675                2680                2685

Val Ser Gly Met Gly Met Gly Arg Gly Gly Pro Glu Pro Pro Ala
    2690                2695                2700

Ser Ser Glu Met Asp Asp Asn Ser Leu Ser Pro Glu Ala Cys Tyr
    2705                2710                2715

Glu Cys Lys Ile Asn Gly Tyr Pro Lys Arg Gly Arg Lys Arg Arg
    2720                2725                2730

Ser Thr Asn Glu Asn
    2735
```

<210> SEQ ID NO 32
<211> LENGTH: 2755
<212> TYPE: PRT
<213> ORGANISM: Artificial Sequence
<220> FEATURE:
<223> OTHER INFORMATION: Synthetic

<400> SEQUENCE: 32

```
Met Arg Arg Gly Gly Leu Leu Glu Val Ala Leu Ala Phe Ala Leu Leu
1               5                   10                  15

Leu Glu Ser Tyr Thr Ser His Gly Ala Asp Ala Asn Leu Glu Ala Gly
                20                  25                  30

Ser Leu Lys Glu Thr Arg Ala Asn Arg Ala Lys Arg Gly Gly Gly
            35                  40                  45

Gly His Asp Ala Leu Lys Gly Pro Asn Val Cys Gly Ser Arg Tyr Asn
        50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
        115                 120                 125
```

```
Cys Ser Asp Asp His Cys Leu Cys Gln Lys Gly Tyr Ile Gly Thr His
    130                 135                 140
Cys Gly Gln Pro Val Cys Glu Ser Gly Cys Leu Asn Gly Arg Cys
145                 150                 155                 160
Val Ala Pro Asn Arg Cys Ala Cys Thr Tyr Gly Phe Thr Gly Pro Gln
                165                 170                 175
Cys Glu Arg Asp Tyr Arg Thr Gly Pro Cys Phe Thr Val Val Ser Asn
                180                 185                 190
Gln Met Cys Gln Gly Gln Leu Ser Gly Ile Val Cys Thr Lys Thr Leu
            195                 200                 205
Cys Cys Ala Thr Val Gly Arg Ala Trp Gly His Pro Cys Glu Met Cys
210                 215                 220
Pro Ala Gln Pro His Pro Cys Arg Arg Gly Phe Ile Pro Asn Ile Arg
225                 230                 235                 240
Thr Gly Ala Cys Gln Asp Val Asp Glu Cys Gln Ala Ile Pro Gly Met
                245                 250                 255
Cys Gln Gly Gly Asn Cys Ile Asn Thr Val Gly Ser Phe Glu Cys Lys
                260                 265                 270
Cys Pro Ala Gly His Lys Phe Asn Glu Val Ser Gln Lys Cys Glu Asp
                275                 280                 285
Ile Asp Glu Cys Ser Thr Ile Pro Gly Val Cys Asp Gly Gly Glu Cys
            290                 295                 300
Thr Asn Thr Val Ser Ser Tyr Phe Cys Lys Cys Pro Pro Gly Phe Tyr
305                 310                 315                 320
Thr Ser Pro Asp Gly Thr Arg Cys Val Asp Val Arg Pro Gly Tyr Cys
                325                 330                 335
Tyr Thr Ala Leu Ala Asn Gly Arg Cys Ser Asn Gln Leu Pro Gln Ser
                340                 345                 350
Ile Thr Lys Met Gln Cys Cys Cys Asp Leu Gly Arg Cys Trp Ser Pro
            355                 360                 365
Gly Val Thr Val Ala Pro Glu Met Cys Pro Ile Arg Ser Thr Glu Asp
            370                 375                 380
Phe Asn Lys Leu Cys Ser Val Pro Leu Val Ile Pro Gly Arg Pro Glu
385                 390                 395                 400
Tyr Pro Pro Pro Ile Gly Pro Leu Pro Val Gln Pro Val Pro
                405                 410                 415
Pro Gly Tyr Pro Pro Gly Pro Val Ile Pro Ala Pro Arg Pro Pro Pro
                420                 425                 430
Glu Tyr Pro Tyr Pro Ser Pro Arg Glu Pro Pro Arg Val Leu Pro
                435                 440                 445
Phe Asn Val Thr Asp Tyr Cys Gln Leu Val Arg Tyr Leu Cys Gln Asn
450                 455                 460
Gly Arg Cys Ile Pro Thr Pro Gly Ser Tyr Arg Cys Glu Cys Asn Lys
465                 470                 475                 480
Gly Phe Gln Leu Asp Ile Arg Gly Glu Cys Ile Asp Val Asp Glu Cys
                485                 490                 495
Glu Lys Asn Pro Cys Thr Gly Gly Glu Cys Ile Asn Asn Gln Gly Ser
            500                 505                 510
Tyr Thr Cys His Cys Arg Ala Gly Tyr Gln Ser Thr Leu Thr Arg Thr
            515                 520                 525
Glu Cys Arg Asp Ile Asp Glu Cys Leu Gln Asn Gly Arg Ile Cys Asn
530                 535                 540
```

```
Asn Gly Arg Cys Ile Asn Thr Asp Gly Ser Phe His Cys Val Cys Asn
545                 550                 555                 560
Ala Gly Phe His Val Thr Arg Asp Gly Lys Asn Cys Glu Asp Met Asp
                565                 570                 575
Glu Cys Ser Ile Arg Asn Met Cys Leu Asn Gly Met Cys Ile Asn Glu
                580                 585                 590
Asp Gly Ser Phe Lys Cys Ile Cys Lys Pro Gly Phe Gln Leu Ala Ser
                595                 600                 605
Asp Gly Arg Tyr Cys Lys Asp Ile Asn Glu Cys Glu Thr Pro Gly Ile
                610                 615                 620
Cys Met Asn Gly Arg Cys Val Asn Thr Asp Gly Ser Tyr Arg Cys Glu
625                 630                 635                 640
Cys Phe Pro Gly Leu Ala Val Gly Leu Asp Gly Arg Val Cys Val Asp
                645                 650                 655
Thr His Met Arg Ser Thr Cys Tyr Gly Gly Tyr Arg Arg Gly Gln Cys
                660                 665                 670
Val Lys Pro Leu Phe Gly Ala Val Thr Lys Ser Glu Cys Cys Cys Ala
                675                 680                 685
Ser Thr Glu Tyr Ala Phe Gly Glu Pro Cys Gln Pro Cys Pro Ala Gln
690                 695                 700
Asn Ser Ala Glu Tyr Gln Ala Leu Cys Ser Ser Gly Pro Gly Met Thr
705                 710                 715                 720
Ser Ala Gly Thr Asp Ile Asn Glu Cys Ala Leu Asp Pro Asp Ile Cys
                725                 730                 735
Pro Asn Gly Ile Cys Glu Asn Leu Arg Gly Thr Tyr Lys Cys Ile Cys
                740                 745                 750
Asn Ser Gly Tyr Glu Val Asp Ile Thr Gly Lys Asn Cys Val Asp Ile
                755                 760                 765
Asn Glu Cys Val Leu Asn Ser Leu Leu Cys Asp Asn Gly Gln Cys Arg
770                 775                 780
Asn Thr Pro Gly Ser Phe Val Cys Thr Cys Pro Lys Gly Phe Val Tyr
785                 790                 795                 800
Lys Pro Asp Leu Lys Thr Cys Glu Asp Ile Asp Glu Cys Glu Ser Ser
                805                 810                 815
Pro Cys Ile Asn Gly Val Cys Lys Asn Ser Pro Gly Ser Phe Ile Cys
                820                 825                 830
Glu Cys Ser Pro Glu Ser Thr Leu Asp Pro Thr Lys Thr Ile Cys Ile
                835                 840                 845
Glu Thr Ile Lys Gly Thr Cys Trp Gln Thr Val Ile Asp Gly Arg Cys
850                 855                 860
Glu Ile Asn Ile Asn Gly Ala Thr Leu Lys Ser Glu Cys Cys Ser Ser
865                 870                 875                 880
Leu Gly Ala Ala Trp Gly Ser Pro Cys Thr Ile Cys Gln Leu Asp Pro
                885                 890                 895
Ile Cys Gly Lys Gly Phe Ser Arg Ile Lys Gly Thr Gln Cys Glu Asp
                900                 905                 910
Ile Asn Glu Cys Glu Val Phe Pro Gly Val Cys Lys Asn Gly Leu Cys
                915                 920                 925
Val Asn Ser Arg Gly Ser Phe Lys Cys Glu Cys Pro Asn Gly Met Thr
                930                 935                 940
Leu Asp Ala Thr Gly Arg Ile Cys Leu Asp Ile Arg Leu Glu Thr Cys
945                 950                 955                 960
Phe Leu Lys Tyr Asp Asp Glu Glu Cys Thr Leu Pro Ile Ala Gly Arg
```

-continued

His Arg Met Asp Ala Cys Cys Cys Ser Val Gly Ala Ala Trp Gly Thr
965                 970                 975
Glu Glu Cys Glu Glu Cys Pro Leu Arg Asn Ser Arg Glu Tyr Glu Glu
980                 985                 990
Leu Cys Pro Arg Gly Pro Gly Phe Ala Thr Lys Asp Ile Thr Asn
995                 1000                1005
Gly Lys Pro Phe Phe Lys Asp Ile Asn Glu Cys Lys Met Ile Pro
1010                1015                1020
Ser Leu Cys Thr His Gly Lys Cys Arg Asn Thr Ile Gly Ser Phe
1025                1030                1035
Lys Cys Arg Cys Asp Ser Gly Phe Ala Leu Asp Ser Glu Glu Arg
1040                1045                1050
Asn Cys Thr Asp Ile Asp Glu Cys Arg Ile Ser Pro Asp Leu Cys
1055                1060                1065
Gly Arg Gly Gln Cys Val Asn Thr Pro Gly Asp Phe Glu Cys Lys
1070                1075                1080
Cys Asp Glu Gly Tyr Glu Ser Gly Phe Met Met Lys Asn Cys
1085                1090                1095
Met Asp Ile Asp Glu Cys Gln Arg Asp Pro Leu Leu Cys Arg Gly
1100                1105                1110
Gly Ile Cys His Asn Thr Glu Gly Ser Tyr Arg Cys Glu Cys Pro
1115                1120                1125
Pro Gly His Gln Leu Ser Pro Asn Ile Ser Ala Cys Ile Asp Ile
1130                1135                1140
Asn Glu Cys Glu Leu Ser Ala Asn Leu Cys Pro His Gly Arg Cys
1145                1150                1155
Val Asn Leu Ile Gly Lys Tyr Gln Cys Ala Cys Asn Pro Gly Tyr
1160                1165                1170
His Pro Thr His Asp Arg Leu Phe Cys Val Asp Ile Asp Glu Cys
1175                1180                1185
Ser Ile Met Asn Gly Gly Cys Glu Thr Phe Cys Thr Asn Ser Asp
1190                1195                1200
Gly Ser Tyr Glu Cys Ser Cys Gln Pro Gly Phe Ala Leu Met Pro
1205                1210                1215
Asp Gln Arg Ser Cys Thr Asp Ile Asp Glu Cys Glu Asp Asn Pro
1220                1225                1230
Asn Ile Cys Asp Gly Gly Gln Cys Thr Asn Ile Pro Gly Glu Tyr
1235                1240                1245
Arg Cys Leu Cys Tyr Asp Gly Phe Met Ala Ser Glu Asp Met Lys
1250                1255                1260
Thr Cys Val Asp Val Asn Glu Cys Asp Leu Asn Pro Asn Ile Cys
1265                1270                1275
Leu Ser Gly Thr Cys Glu Asn Thr Lys Gly Ser Phe Ile Cys His
1280                1285                1290
Cys Asp Met Gly Tyr Ser Gly Lys Lys Gly Lys Thr Gly Cys Thr
1295                1300                1305
Asp Ile Asn Glu Cys Glu Ile Gly Ala His Asn Cys Gly Arg His
1310                1315                1320
Ala Val Cys Thr Asn Thr Ala Gly Ser Phe Lys Cys Ser Cys Ser
1325                1330                1335
Pro Gly Trp Ile Gly Asp Gly Ile Lys Cys Thr Asp Leu Asp Glu
1340                1345                1350

Cys Ser Asn Gly Thr His Met Cys Ser Gln His Ala Asp Cys Lys
1370                    1375                    1380

Asn Thr Met Gly Ser Tyr Arg Cys Leu Cys Lys Asp Gly Tyr Thr
1385                    1390                    1395

Gly Asp Gly Phe Thr Cys Thr Asp Leu Asp Glu Cys Ser Glu Asn
1400                    1405                    1410

Leu Asn Leu Cys Gly Asn Gly Gln Cys Leu Asn Ala Pro Gly Gly
1415                    1420                    1425

Tyr Arg Cys Glu Cys Asp Met Gly Phe Val Pro Ser Ala Asp Gly
1430                    1435                    1440

Lys Ala Cys Glu Asp Ile Asp Glu Cys Ser Leu Pro Asn Ile Cys
1445                    1450                    1455

Val Phe Gly Thr Cys His Asn Leu Pro Gly Leu Phe Arg Cys Glu
1460                    1465                    1470

Cys Glu Ile Gly Tyr Glu Leu Asp Arg Ser Gly Gly Asn Cys Thr
1475                    1480                    1485

Asp Val Asn Glu Cys Leu Asp Pro Thr Thr Cys Ile Ser Gly Asn
1490                    1495                    1500

Cys Val Asn Thr Pro Gly Ser Tyr Thr Cys Asp Cys Pro Pro Asp
1505                    1510                    1515

Phe Glu Leu Asn Pro Thr Arg Val Gly Cys Val Asp Thr Arg Ser
1520                    1525                    1530

Gly Asn Cys Tyr Leu Asp Ile Arg Pro Arg Gly Asp Asn Gly Asp
1535                    1540                    1545

Thr Ala Cys Ser Asn Glu Ile Gly Val Gly Val Ser Lys Ala Ser
1550                    1555                    1560

Cys Cys Cys Ser Leu Gly Lys Ala Trp Gly Thr Pro Cys Glu Leu
1565                    1570                    1575

Cys Pro Ser Val Asn Thr Ser Glu Tyr Lys Ile Leu Cys Pro Gly
1580                    1585                    1590

Gly Glu Gly Phe Arg Pro Asn Pro Ile Thr Val Ile Leu Glu Asp
1595                    1600                    1605

Ile Asp Glu Cys Gln Glu Leu Pro Gly Leu Cys Gln Gly Gly Lys
1610                    1615                    1620

Cys Ile Asn Thr Phe Gly Ser Phe Gln Cys Arg Cys Pro Thr Gly
1625                    1630                    1635

Tyr Tyr Leu Asn Glu Asp Thr Arg Val Cys Asp Asp Val Asn Glu
1640                    1645                    1650

Cys Glu Thr Pro Gly Ile Cys Gly Pro Gly Thr Cys Tyr Asn Thr
1655                    1660                    1665

Val Gly Asn Tyr Thr Cys Ile Cys Pro Pro Asp Tyr Met Gln Val
1670                    1675                    1680

Asn Gly Gly Asn Asn Cys Met Asp Met Arg Arg Ser Leu Cys Tyr
1685                    1690                    1695

Arg Asn Tyr Tyr Ala Asp Asn Gln Thr Cys Asp Gly Glu Leu Leu
1700                    1705                    1710

Phe Asn Met Thr Lys Lys Met Cys Cys Cys Ser Tyr Asn Ile Gly
1715                    1720                    1725

Arg Ala Trp Asn Lys Pro Cys Glu Gln Cys Pro Ile Pro Ser Thr
1730                    1735                    1740

Asp Glu Phe Ala Thr Leu Cys Gly Ser Gln Arg Pro Gly Phe Val
1745                    1750                    1755

-continued

```
Ile Asp Ile Tyr Thr Gly Leu Pro Val Asp Ile Asp Glu Cys Arg
1760                1765                1770

Glu Ile Pro Gly Val Cys Glu Asn Gly Val Cys Ile Asn Met Val
1775                1780                1785

Gly Ser Phe Arg Cys Glu Cys Pro Val Gly Phe Phe Tyr Asn Asp
1790                1795                1800

Lys Leu Leu Val Cys Glu Asp Ile Asp Glu Cys Gln Asn Gly Pro
1805                1810                1815

Val Cys Gln Arg Asn Ala Glu Cys Ile Asn Thr Ala Gly Ser Tyr
1820                1825                1830

Arg Cys Asp Cys Lys Pro Gly Tyr Arg Leu Thr Ser Thr Gly Gln
1835                1840                1845

Cys Asn Asp Arg Asn Glu Cys Gln Glu Ile Pro Asn Ile Cys Ser
1850                1855                1860

His Gly Gln Cys Ile Asp Thr Val Gly Ser Phe Tyr Cys Leu Cys
1865                1870                1875

His Thr Gly Phe Lys Thr Asn Val Asp Gln Thr Met Cys Leu Asp
1880                1885                1890

Ile Asn Glu Cys Glu Arg Asp Ala Cys Gly Asn Gly Thr Cys Arg
1895                1900                1905

Asn Thr Ile Gly Ser Phe Asn Cys Arg Cys Asn His Gly Phe Ile
1910                1915                1920

Leu Ser His Asn Asn Asp Cys Ile Asp Val Asp Glu Cys Ala Thr
1925                1930                1935

Gly Asn Gly Asn Leu Cys Arg Asn Gly Gln Cys Val Asn Thr Val
1940                1945                1950

Gly Ser Phe Gln Cys Arg Cys Asn Glu Gly Tyr Glu Val Ala Pro
1955                1960                1965

Asp Gly Arg Thr Cys Val Asp Ile Asn Glu Cys Val Leu Asp Pro
1970                1975                1980

Gly Lys Cys Ala Pro Gly Thr Cys Gln Asn Leu Asp Gly Ser Tyr
1985                1990                1995

Arg Cys Ile Cys Pro Pro Gly Tyr Ser Leu Gln Asn Asp Lys Cys
2000                2005                2010

Glu Asp Ile Asp Glu Cys Val Glu Glu Pro Glu Ile Cys Ala Leu
2015                2020                2025

Gly Thr Cys Ser Asn Thr Glu Gly Ser Phe Lys Cys Leu Cys Pro
2030                2035                2040

Glu Gly Phe Ser Leu Ser Ser Thr Gly Arg Arg Cys Gln Asp Leu
2045                2050                2055

Arg Met Ser Tyr Cys Tyr Ala Lys Phe Glu Gly Gly Lys Cys Ser
2060                2065                2070

Ser Pro Lys Ser Arg Asn His Ser Lys Gln Glu Cys Cys Cys Ala
2075                2080                2085

Leu Lys Gly Glu Gly Trp Gly Asp Pro Cys Glu Leu Cys Pro Thr
2090                2095                2100

Glu Pro Asp Glu Ala Phe Arg Gln Ile Cys Pro Phe Gly Ser Gly
2105                2110                2115

Ile Ile Val Gly Pro Asp Asp Ser Ala Val Asp Met Asp Glu Cys
2120                2125                2130

Lys Glu Pro Asp Val Cys Arg His Gly Gln Cys Ile Asn Thr Asp
2135                2140                2145

Gly Ser Tyr Arg Cys Glu Cys Pro Phe Gly Tyr Ile Leu Glu Gly
```

-continued

```
                2150                2155                2160
Asn Glu Cys Val Asp Thr Asp Glu Cys Ser Val Gly Asn Pro Cys
    2165                2170                2175
Gly Asn Gly Thr Cys Lys Asn Val Ile Gly Gly Phe Glu Cys Thr
    2180                2185                2190
Cys Glu Glu Gly Phe Glu Pro Gly Pro Met Met Thr Cys Glu Asp
    2195                2200                2205
Ile Asn Glu Cys Ala Gln Asn Pro Leu Leu Cys Ala Phe Arg Cys
    2210                2215                2220
Val Asn Thr Tyr Gly Ser Tyr Glu Cys Lys Cys Pro Val Gly Tyr
    2225                2230                2235
Val Leu Arg Glu Asp Arg Arg Met Cys Lys Asp Glu Asp Glu Cys
    2240                2245                2250
Ala Glu Gly Lys His Asp Cys Thr Glu Lys Gln Met Glu Cys Lys
    2255                2260                2265
Asn Leu Ile Gly Thr Tyr Met Cys Ile Cys Gly Pro Gly Tyr Gln
    2270                2275                2280
Arg Arg Pro Asp Gly Glu Gly Cys Ile Asp Glu Asn Glu Cys Gln
    2285                2290                2295
Thr Lys Pro Gly Ile Cys Glu Asn Gly Arg Cys Leu Asn Thr Leu
    2300                2305                2310
Gly Ser Tyr Thr Cys Glu Cys Asn Asp Gly Phe Thr Ala Ser Pro
    2315                2320                2325
Thr Gln Asp Glu Cys Leu Asp Asn Arg Glu Gly Tyr Cys Phe Ser
    2330                2335                2340
Glu Val Leu Gln Asn Met Cys Gln Ile Gly Ser Ser Asn Arg Asn
    2345                2350                2355
Pro Val Thr Lys Ser Glu Cys Cys Cys Asp Gly Gly Arg Gly Trp
    2360                2365                2370
Gly Pro His Cys Glu Ile Cys Pro Phe Glu Gly Thr Val Ala Tyr
    2375                2380                2385
Lys Lys Leu Cys Pro His Gly Arg Gly Phe Met Thr Asn Gly Ala
    2390                2395                2400
Asp Ile Asp Glu Cys Lys Val Ile His Asp Val Cys Arg Asn Gly
    2405                2410                2415
Glu Cys Val Asn Asp Arg Gly Ser Tyr His Cys Ile Cys Lys Thr
    2420                2425                2430
Gly Tyr Thr Pro Asp Ile Thr Gly Thr Ala Cys Val Asp Leu Asn
    2435                2440                2445
Glu Cys Asn Gln Ala Pro Lys Pro Cys Asn Phe Ile Cys Lys Asn
    2450                2455                2460
Thr Glu Gly Ser Tyr Gln Cys Ser Cys Pro Lys Gly Tyr Ile Leu
    2465                2470                2475
Gln Glu Asp Gly Arg Ser Cys Lys Asp Leu Asp Glu Cys Ala Thr
    2480                2485                2490
Lys Gln His Asn Cys Gln Phe Leu Cys Val Asn Thr Ile Gly Gly
    2495                2500                2505
Phe Thr Cys Lys Cys Pro Pro Gly Phe Thr Gln His His Thr Ala
    2510                2515                2520
Cys Ile Asp Asn Asn Glu Cys Thr Ser Asp Ile Asn Leu Cys Gly
    2525                2530                2535
Ser Lys Gly Val Cys Gln Asn Thr Pro Gly Ser Phe Thr Cys Glu
    2540                2545                2550
```

Cys Gln Arg Gly Phe Ser Leu Asp Gln Ser Gly Ala Ser Cys Glu
         2555                2560                2565

Asp Val Asp Glu Cys Glu Gly Asn His Arg Cys Gln His Gly Cys
    2570                2575                2580

Gln Asn Ile Ile Gly Gly Tyr Arg Cys Ser Cys Pro Gln Gly Tyr
        2585                2590                2595

Leu Gln His Tyr Gln Trp Asn Gln Cys Val Asp Glu Asn Glu Cys
    2600                2605                2610

Leu Ser Ala His Val Cys Gly Gly Ala Ser Cys His Asn Thr Leu
    2615                2620                2625

Gly Ser Tyr Lys Cys Met Cys Pro Thr Gly Phe Gln Tyr Glu Gln
    2630                2635                2640

Phe Ser Gly Gly Cys Gln Asp Ile Asn Glu Cys Gly Ser Ser Gln
    2645                2650                2655

Ala Pro Cys Ser Tyr Gly Cys Ser Asn Thr Glu Gly Gly Tyr Leu
    2660                2665                2670

Cys Gly Cys Pro Pro Gly Tyr Phe Arg Ile Gly Gln Gly His Cys
    2675                2680                2685

Val Ser Gly Met Gly Met Gly Arg Gly Gly Pro Glu Pro Pro Ala
    2690                2695                2700

Ser Ser Glu Met Asp Asp Asn Ser Leu Ser Pro Glu Ala Cys Tyr
    2705                2710                2715

Glu Cys Lys Ile Asn Gly Tyr Pro Lys Ala Ala Gln Ser His Leu
    2720                2725                2730

Pro Ala Thr Arg Pro Glu Thr Glu Lys His Glu Arg Asn Gly Cys
    2735                2740                2745

Leu Arg His Pro Gly Arg Val
    2750                2755

<210> SEQ ID NO 33
<211> LENGTH: 2737
<212> TYPE: PRT
<213> ORGANISM: Artificial Sequence
<220> FEATURE:
<223> OTHER INFORMATION: Synthetic

<400> SEQUENCE: 33

Met Arg Arg Gly Gly Leu Leu Glu Val Ala Leu Ala Phe Ala Leu Leu
1               5                   10                  15

Leu Glu Ser Tyr Thr Ser His Gly Ala Asp Ala Asn Leu Glu Ala Gly
            20                  25                  30

Ser Leu Lys Glu Thr Arg Ala Asn Arg Ala Lys Arg Arg Gly Gly Gly
        35                  40                  45

Gly His Asp Ala Leu Lys Gly Pro Asn Val Cys Gly Ser Arg Tyr Asn
    50                  55                  60

Ala Tyr Cys Cys Pro Gly Trp Lys Thr Leu Pro Gly Gly Asn Gln Cys
65                  70                  75                  80

Ile Val Pro Ile Cys Arg His Ser Cys Gly Asp Gly Phe Cys Ser Arg
                85                  90                  95

Pro Asn Met Cys Thr Cys Pro Ser Gly Gln Ile Ser Pro Ser Cys Gly
            100                 105                 110

Ser Arg Ser Ile Gln His Cys Ser Ile Arg Cys Met Asn Gly Gly Ser
        115                 120                 125

Cys Ser Asp Asp His Cys Leu Cys Gln Lys Gly Tyr Ile Gly Thr His
    130                 135                 140

-continued

```
Cys Gly Gln Pro Val Cys Glu Ser Gly Cys Leu Asn Gly Gly Arg Cys
145                 150                 155                 160

Val Ala Pro Asn Arg Cys Ala Cys Thr Tyr Gly Phe Thr Gly Pro Gln
            165                 170                 175

Cys Glu Arg Asp Tyr Arg Thr Gly Pro Cys Phe Thr Val Ser Asn
            180                 185                 190

Gln Met Cys Gln Gly Gln Leu Ser Gly Ile Val Cys Thr Lys Thr Leu
        195                 200                 205

Cys Cys Ala Thr Val Gly Arg Ala Trp Gly His Pro Cys Glu Met Cys
    210                 215                 220

Pro Ala Gln Pro His Pro Cys Arg Arg Gly Phe Ile Pro Asn Ile Arg
225                 230                 235                 240

Thr Gly Ala Cys Gln Asp Val Asp Glu Cys Gln Ala Ile Pro Gly Met
                245                 250                 255

Cys Gln Gly Gly Asn Cys Ile Asn Thr Val Gly Ser Phe Glu Cys Lys
                260                 265                 270

Cys Pro Ala Gly His Lys Phe Asn Glu Val Ser Gln Lys Cys Glu Asp
            275                 280                 285

Ile Asp Glu Cys Ser Thr Ile Pro Gly Val Cys Asp Gly Gly Glu Cys
290                 295                 300

Thr Asn Thr Val Ser Ser Tyr Phe Cys Lys Cys Pro Pro Gly Phe Tyr
305                 310                 315                 320

Thr Ser Pro Asp Gly Thr Arg Cys Val Asp Val Arg Pro Gly Tyr Cys
                325                 330                 335

Tyr Thr Ala Leu Ala Asn Gly Arg Cys Ser Asn Gln Leu Pro Gln Ser
            340                 345                 350

Ile Thr Lys Met Gln Cys Cys Cys Asp Leu Gly Arg Cys Trp Ser Pro
        355                 360                 365

Gly Val Thr Val Ala Pro Glu Met Cys Pro Ile Arg Ser Thr Glu Asp
    370                 375                 380

Phe Asn Lys Leu Cys Ser Val Pro Leu Val Ile Pro Gly Arg Pro Glu
385                 390                 395                 400

Tyr Pro Pro Pro Ile Gly Pro Leu Pro Val Gln Pro Val Pro
                405                 410                 415

Pro Gly Tyr Pro Pro Gly Pro Val Ile Pro Ala Pro Arg Pro Pro Pro
            420                 425                 430

Glu Tyr Pro Tyr Pro Ser Pro Ser Arg Glu Pro Pro Arg Val Leu Pro
        435                 440                 445

Phe Asn Val Thr Asp Tyr Cys Gln Leu Val Arg Tyr Leu Cys Gln Asn
    450                 455                 460

Gly Arg Cys Ile Pro Thr Pro Gly Ser Tyr Arg Cys Glu Cys Asn Lys
465                 470                 475                 480

Gly Phe Gln Leu Asp Ile Arg Gly Glu Cys Ile Asp Val Asp Glu Cys
                485                 490                 495

Glu Lys Asn Pro Cys Thr Gly Gly Glu Cys Ile Asn Asn Gln Gly Ser
                500                 505                 510

Tyr Thr Cys His Cys Arg Ala Gly Tyr Gln Ser Thr Leu Thr Arg Thr
            515                 520                 525

Glu Cys Arg Asp Ile Asp Glu Cys Leu Gln Asn Gly Arg Ile Cys Asn
        530                 535                 540

Asn Gly Arg Cys Ile Asn Thr Asp Gly Ser Phe His Cys Val Cys Asn
545                 550                 555                 560
```

```
Ala Gly Phe His Val Thr Arg Asp Gly Lys Asn Cys Glu Asp Met Asp
                565                 570                 575
Glu Cys Ser Ile Arg Asn Met Cys Leu Asn Gly Met Cys Ile Asn Glu
            580                 585                 590
Asp Gly Ser Phe Lys Cys Ile Cys Lys Pro Gly Phe Gln Leu Ala Ser
            595                 600                 605
Asp Gly Arg Tyr Cys Lys Asp Ile Asn Glu Cys Glu Thr Pro Gly Ile
            610                 615                 620
Cys Met Asn Gly Arg Cys Val Asn Thr Asp Gly Ser Tyr Arg Cys Glu
625                 630                 635                 640
Cys Phe Pro Gly Leu Ala Val Gly Leu Asp Gly Arg Val Cys Val Asp
                645                 650                 655
Thr His Met Arg Ser Thr Cys Tyr Gly Gly Tyr Arg Arg Gly Gln Cys
                660                 665                 670
Val Lys Pro Leu Phe Gly Ala Val Thr Lys Ser Glu Cys Cys Cys Ala
                675                 680                 685
Ser Thr Glu Tyr Ala Phe Gly Glu Pro Cys Gln Pro Cys Pro Ala Gln
                690                 695                 700
Asn Ser Ala Glu Tyr Gln Ala Leu Cys Ser Ser Gly Pro Gly Met Thr
705                 710                 715                 720
Ser Ala Gly Thr Asp Ile Asn Glu Cys Ala Leu Asp Pro Asp Ile Cys
                725                 730                 735
Pro Asn Gly Ile Cys Glu Asn Leu Arg Gly Thr Tyr Lys Cys Ile Cys
                740                 745                 750
Asn Ser Gly Tyr Glu Val Asp Ile Thr Gly Lys Asn Cys Val Asp Ile
                755                 760                 765
Asn Glu Cys Val Leu Asn Ser Leu Leu Cys Asp Asn Gly Gln Cys Arg
770                 775                 780
Asn Thr Pro Gly Ser Phe Val Cys Thr Cys Pro Lys Gly Phe Val Tyr
785                 790                 795                 800
Lys Pro Asp Leu Lys Thr Cys Glu Asp Ile Asp Glu Cys Glu Ser Ser
                805                 810                 815
Pro Cys Ile Asn Gly Val Cys Lys Asn Ser Pro Gly Ser Phe Ile Cys
                820                 825                 830
Glu Cys Ser Pro Glu Ser Thr Leu Asp Pro Thr Lys Thr Ile Cys Ile
                835                 840                 845
Glu Thr Ile Lys Gly Thr Cys Trp Gln Thr Val Ile Asp Gly Arg Cys
                850                 855                 860
Glu Ile Asn Ile Asn Gly Ala Thr Leu Lys Ser Glu Cys Cys Ser Ser
865                 870                 875                 880
Leu Gly Ala Ala Trp Gly Ser Pro Cys Thr Ile Cys Gln Leu Asp Pro
                885                 890                 895
Ile Cys Gly Lys Gly Phe Ser Arg Ile Lys Gly Thr Gln Cys Glu Asp
                900                 905                 910
Ile Asn Glu Cys Glu Val Phe Pro Gly Val Cys Lys Asn Gly Leu Cys
                915                 920                 925
Val Asn Ser Arg Gly Ser Phe Lys Cys Glu Cys Pro Asn Gly Met Thr
                930                 935                 940
Leu Asp Ala Thr Gly Arg Ile Cys Leu Asp Ile Arg Leu Glu Thr Cys
945                 950                 955                 960
Phe Leu Lys Tyr Asp Asp Glu Glu Cys Thr Leu Pro Ile Ala Gly Arg
                965                 970                 975
His Arg Met Asp Ala Cys Cys Cys Ser Val Gly Ala Ala Trp Gly Thr
```

```
                980              985              990
      Glu Glu Cys Glu Glu Cys Pro Leu Arg Asn Ser Arg Glu Tyr Glu Glu
              995              1000             1005

Leu Cys Pro Arg Gly Pro Gly Phe Ala Thr Lys Asp Ile Thr Asn
      1010             1015             1020

Gly Lys Pro Phe Phe Lys Asp Ile Asn Glu Cys Lys Met Ile Pro
      1025             1030             1035

Ser Leu Cys Thr His Gly Lys Cys Arg Asn Thr Ile Gly Ser Phe
      1040             1045             1050

Lys Cys Arg Cys Asp Ser Gly Phe Ala Leu Asp Ser Glu Glu Arg
      1055             1060             1065

Asn Cys Thr Asp Ile Asp Glu Cys Arg Ile Ser Pro Asp Leu Cys
      1070             1075             1080

Gly Arg Gly Gln Cys Val Asn Thr Pro Gly Asp Phe Glu Cys Lys
      1085             1090             1095

Cys Asp Glu Gly Tyr Glu Ser Gly Phe Met Met Met Lys Asn Cys
      1100             1105             1110

Met Asp Ile Asp Glu Cys Gln Arg Asp Pro Leu Leu Cys Arg Gly
      1115             1120             1125

Gly Ile Cys His Asn Thr Glu Gly Ser Tyr Arg Cys Glu Cys Pro
      1130             1135             1140

Pro Gly His Gln Leu Ser Pro Asn Ile Ser Ala Cys Ile Asp Ile
      1145             1150             1155

Asn Glu Cys Glu Leu Ser Ala Asn Leu Cys Pro His Gly Arg Cys
      1160             1165             1170

Val Asn Leu Ile Gly Lys Tyr Gln Cys Ala Cys Asn Pro Gly Tyr
      1175             1180             1185

His Pro Thr His Asp Arg Leu Phe Cys Val Asp Ile Asp Glu Cys
      1190             1195             1200

Ser Ile Met Asn Gly Gly Cys Glu Thr Phe Cys Thr Asn Ser Asp
      1205             1210             1215

Gly Ser Tyr Glu Cys Ser Cys Gln Pro Gly Phe Ala Leu Met Pro
      1220             1225             1230

Asp Gln Arg Ser Cys Thr Asp Ile Asp Glu Cys Glu Asp Asn Pro
      1235             1240             1245

Asn Ile Cys Asp Gly Gly Gln Cys Thr Asn Ile Pro Gly Glu Tyr
      1250             1255             1260

Arg Cys Leu Cys Tyr Asp Gly Phe Met Ala Ser Glu Asp Met Lys
      1265             1270             1275

Thr Cys Val Asp Val Asn Glu Cys Asp Leu Asn Pro Asn Ile Cys
      1280             1285             1290

Leu Ser Gly Thr Cys Glu Asn Thr Lys Gly Ser Phe Ile Cys His
      1295             1300             1305

Cys Asp Met Gly Tyr Ser Gly Lys Lys Gly Lys Thr Gly Cys Thr
      1310             1315             1320

Asp Ile Asn Glu Cys Glu Ile Gly Ala His Asn Cys Gly Arg His
      1325             1330             1335

Ala Val Cys Thr Asn Thr Ala Gly Ser Phe Lys Cys Ser Cys Ser
      1340             1345             1350

Pro Gly Trp Ile Gly Asp Gly Ile Lys Cys Thr Asp Leu Asp Glu
      1355             1360             1365

Cys Ser Asn Gly Thr His Met Cys Ser Gln His Ala Asp Cys Lys
      1370             1375             1380
```

-continued

```
Asn Thr Met Gly Ser Tyr Arg Cys Leu Cys Lys Asp Gly Tyr Thr
            1385                1390                1395
Gly Asp Gly Phe Thr Cys Thr Asp Leu Asp Glu Cys Ser Glu Asn
    1400                1405                1410
Leu Asn Leu Cys Gly Asn Gly Gln Cys Leu Asn Ala Pro Gly Gly
    1415                1420                1425
Tyr Arg Cys Glu Cys Asp Met Gly Phe Val Pro Ser Ala Asp Gly
    1430                1435                1440
Lys Ala Cys Glu Asp Ile Asp Glu Cys Ser Leu Pro Asn Ile Cys
    1445                1450                1455
Val Phe Gly Thr Cys His Asn Leu Pro Gly Leu Phe Arg Cys Glu
    1460                1465                1470
Cys Glu Ile Gly Tyr Glu Leu Asp Arg Ser Gly Gly Asn Cys Thr
    1475                1480                1485
Asp Val Asn Glu Cys Leu Asp Pro Thr Thr Cys Ile Ser Gly Asn
    1490                1495                1500
Cys Val Asn Thr Pro Gly Ser Tyr Thr Cys Asp Cys Pro Pro Asp
    1505                1510                1515
Phe Glu Leu Asn Pro Thr Arg Val Gly Cys Val Asp Thr Arg Ser
    1520                1525                1530
Gly Asn Cys Tyr Leu Asp Ile Arg Pro Arg Gly Asp Asn Gly Asp
    1535                1540                1545
Thr Ala Cys Ser Asn Glu Ile Gly Val Gly Val Ser Lys Ala Ser
    1550                1555                1560
Cys Cys Cys Ser Leu Gly Lys Ala Trp Gly Thr Pro Cys Glu Leu
    1565                1570                1575
Cys Pro Ser Val Asn Thr Ser Glu Tyr Lys Ile Leu Cys Pro Gly
    1580                1585                1590
Gly Glu Gly Phe Arg Pro Asn Pro Ile Thr Val Ile Leu Glu Asp
    1595                1600                1605
Ile Asp Glu Cys Gln Glu Leu Pro Gly Leu Cys Gln Gly Gly Lys
    1610                1615                1620
Cys Ile Asn Thr Phe Gly Ser Phe Gln Cys Arg Cys Pro Thr Gly
    1625                1630                1635
Tyr Tyr Leu Asn Glu Asp Thr Arg Val Cys Asp Asp Val Asn Glu
    1640                1645                1650
Cys Glu Thr Pro Gly Ile Cys Gly Pro Gly Thr Cys Tyr Asn Thr
    1655                1660                1665
Val Gly Asn Tyr Thr Cys Ile Cys Pro Pro Asp Tyr Met Gln Val
    1670                1675                1680
Asn Gly Gly Asn Asn Cys Met Asp Met Arg Arg Ser Leu Cys Tyr
    1685                1690                1695
Arg Asn Tyr Tyr Ala Asp Asn Gln Thr Cys Asp Gly Glu Leu Leu
    1700                1705                1710
Phe Asn Met Thr Lys Lys Met Cys Cys Cys Ser Tyr Asn Ile Gly
    1715                1720                1725
Arg Ala Trp Asn Lys Pro Cys Glu Gln Cys Pro Ile Pro Ser Thr
    1730                1735                1740
Asp Glu Phe Ala Thr Leu Cys Gly Ser Gln Arg Pro Gly Phe Val
    1745                1750                1755
Ile Asp Ile Tyr Thr Gly Leu Pro Val Asp Ile Asp Glu Cys Arg
    1760                1765                1770
```

```
Glu Ile Pro Gly Val Cys Glu Asn Gly Val Cys Ile Asn Met Val
1775                1780                1785

Gly Ser Phe Arg Cys Glu Cys Pro Val Gly Phe Phe Tyr Asn Asp
1790                1795                1800

Lys Leu Leu Val Cys Glu Asp Ile Asp Glu Cys Gln Asn Gly Pro
1805                1810                1815

Val Cys Gln Arg Asn Ala Glu Cys Ile Asn Thr Ala Gly Ser Tyr
1820                1825                1830

Arg Cys Asp Cys Lys Pro Gly Tyr Arg Leu Thr Ser Thr Gly Gln
1835                1840                1845

Cys Asn Asp Arg Asn Glu Cys Gln Glu Ile Pro Asn Ile Cys Ser
1850                1855                1860

His Gly Gln Cys Ile Asp Thr Val Gly Ser Phe Tyr Cys Leu Cys
1865                1870                1875

His Thr Gly Phe Lys Thr Asn Val Asp Gln Thr Met Cys Leu Asp
1880                1885                1890

Ile Asn Glu Cys Glu Arg Asp Ala Cys Gly Asn Gly Thr Cys Arg
1895                1900                1905

Asn Thr Ile Gly Ser Phe Asn Cys Arg Cys Asn His Gly Phe Ile
1910                1915                1920

Leu Ser His Asn Asn Asp Cys Ile Asp Val Asp Glu Cys Ala Thr
1925                1930                1935

Gly Asn Gly Asn Leu Cys Arg Asn Gly Gln Cys Val Asn Thr Val
1940                1945                1950

Gly Ser Phe Gln Cys Arg Cys Asn Glu Gly Tyr Glu Val Ala Pro
1955                1960                1965

Asp Gly Arg Thr Cys Val Asp Ile Asn Glu Cys Val Leu Asp Pro
1970                1975                1980

Gly Lys Cys Ala Pro Gly Thr Cys Gln Asn Leu Asp Gly Ser Tyr
1985                1990                1995

Arg Cys Ile Cys Pro Pro Gly Tyr Ser Leu Gln Asn Asp Lys Cys
2000                2005                2010

Glu Asp Ile Asp Glu Cys Val Glu Glu Pro Glu Ile Cys Ala Leu
2015                2020                2025

Gly Thr Cys Ser Asn Thr Glu Gly Ser Phe Lys Cys Leu Cys Pro
2030                2035                2040

Glu Gly Phe Ser Leu Ser Ser Thr Gly Arg Arg Cys Gln Asp Leu
2045                2050                2055

Arg Met Ser Tyr Cys Tyr Ala Lys Phe Glu Gly Gly Lys Cys Ser
2060                2065                2070

Ser Pro Lys Ser Arg Asn His Ser Lys Gln Glu Cys Cys Cys Ala
2075                2080                2085

Leu Lys Gly Glu Gly Trp Gly Asp Pro Cys Glu Leu Cys Pro Thr
2090                2095                2100

Glu Pro Asp Glu Ala Phe Arg Gln Ile Cys Pro Phe Gly Ser Gly
2105                2110                2115

Ile Ile Val Gly Pro Asp Asp Ser Ala Val Asp Met Asp Glu Cys
2120                2125                2130

Lys Glu Pro Asp Val Cys Arg His Gly Gln Cys Ile Asn Thr Asp
2135                2140                2145

Gly Ser Tyr Arg Cys Glu Cys Pro Phe Gly Tyr Ile Leu Glu Gly
2150                2155                2160

Asn Glu Cys Val Asp Thr Asp Glu Cys Ser Val Gly Asn Pro Cys
```

```
            2165                2170                2175

Gly Asn Gly Thr Cys Lys Asn Val Ile Gly Gly Phe Glu Cys Thr
    2180                2185                2190

Cys Glu Glu Gly Phe Glu Pro Gly Pro Met Met Thr Cys Glu Asp
    2195                2200                2205

Ile Asn Glu Cys Ala Gln Asn Pro Leu Leu Cys Ala Phe Arg Cys
    2210                2215                2220

Val Asn Thr Tyr Gly Ser Tyr Glu Cys Lys Cys Pro Val Gly Tyr
    2225                2230                2235

Val Leu Arg Glu Asp Arg Arg Met Cys Lys Asp Glu Asp Glu Cys
    2240                2245                2250

Ala Glu Gly Lys His Asp Cys Thr Glu Lys Gln Met Glu Cys Lys
    2255                2260                2265

Asn Leu Ile Gly Thr Tyr Met Cys Ile Cys Gly Pro Gly Tyr Gln
    2270                2275                2280

Arg Arg Pro Asp Gly Glu Gly Cys Ile Asp Glu Asn Glu Cys Gln
    2285                2290                2295

Thr Lys Pro Gly Ile Cys Glu Asn Gly Arg Cys Leu Asn Thr Leu
    2300                2305                2310

Gly Ser Tyr Thr Cys Glu Cys Asn Asp Gly Phe Thr Ala Ser Pro
    2315                2320                2325

Thr Gln Asp Glu Cys Leu Asp Asn Arg Glu Gly Tyr Cys Phe Ser
    2330                2335                2340

Glu Val Leu Gln Asn Met Cys Gln Ile Gly Ser Ser Asn Arg Asn
    2345                2350                2355

Pro Val Thr Lys Ser Glu Cys Cys Cys Asp Gly Gly Arg Gly Trp
    2360                2365                2370

Gly Pro His Cys Glu Ile Cys Pro Phe Glu Gly Thr Val Ala Tyr
    2375                2380                2385

Lys Lys Leu Cys Pro His Gly Arg Gly Phe Met Thr Asn Gly Ala
    2390                2395                2400

Asp Ile Asp Glu Cys Lys Val Ile His Asp Val Cys Arg Asn Gly
    2405                2410                2415

Glu Cys Val Asn Asp Arg Gly Ser Tyr His Cys Ile Cys Lys Thr
    2420                2425                2430

Gly Tyr Thr Pro Asp Ile Thr Gly Thr Ala Cys Val Asp Leu Asn
    2435                2440                2445

Glu Cys Asn Gln Ala Pro Lys Pro Cys Asn Phe Ile Cys Lys Asn
    2450                2455                2460

Thr Glu Gly Ser Tyr Gln Cys Ser Cys Pro Lys Gly Tyr Ile Leu
    2465                2470                2475

Gln Glu Asp Gly Arg Ser Cys Lys Asp Leu Asp Glu Cys Ala Thr
    2480                2485                2490

Lys Gln His Asn Cys Gln Phe Leu Cys Val Asn Thr Ile Gly Gly
    2495                2500                2505

Phe Thr Cys Lys Cys Pro Pro Gly Phe Thr Gln His His Thr Ala
    2510                2515                2520

Cys Ile Asp Asn Asn Glu Cys Thr Ser Asp Ile Asn Leu Cys Gly
    2525                2530                2535

Ser Lys Gly Val Cys Gln Asn Thr Pro Gly Ser Phe Thr Cys Glu
    2540                2545                2550

Cys Gln Arg Gly Phe Ser Leu Asp Gln Ser Gly Ala Ser Cys Glu
    2555                2560                2565
```

Asp Val Asp Glu Cys Glu Gly Asn His Arg Cys Gln His Gly Cys
2570                2575                2580

Gln Asn Ile Ile Gly Gly Tyr Arg Cys Ser Cys Pro Gln Gly Tyr
        2585                2590                2595

Leu Gln His Tyr Gln Trp Asn Gln Cys Val Asp Glu Asn Glu Cys
2600                2605                2610

Leu Ser Ala His Val Cys Gly Ala Ser Cys His Asn Thr Leu
2615                2620                2625

Gly Ser Tyr Lys Cys Met Cys Pro Thr Gly Phe Gln Tyr Glu Gln
        2630                2635                2640

Phe Ser Gly Gly Cys Gln Asp Ile Asn Glu Cys Gly Ser Ser Gln
2645                2650                2655

Ala Pro Cys Ser Tyr Gly Cys Ser Asn Thr Glu Gly Gly Tyr Leu
2660                2665                2670

Cys Gly Cys Pro Pro Gly Tyr Phe Arg Ile Gly Gln Gly His Cys
2675                2680                2685

Val Ser Gly Met Gly Met Gly Arg Gly Pro Glu Pro Pro Ala
        2690                2695                2700

Ser Ser Glu Met Asp Asp Asn Ser Leu Ser Pro Glu Ala Cys Tyr
2705                2710                2715

Glu Cys Asp Gln Trp Leu Pro Gln Thr Gly Gln Glu Thr Glu Lys
2720                2725                2730

His Lys Arg Asn
2735

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Glu Thr Glu Lys His Lys Arg Asn
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic

<400> SEQUENCE: 35

Ile Ser Leu Arg Gln Lys Pro Met
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Arg Gly Arg Lys Arg Arg
1               5

<210> SEQ ID NO 37
<211> LENGTH: 23

<212> TYPE: RNA
<213> ORGANISM: Artificial Sequence
<220> FEATURE:
<223> OTHER INFORMATION: Synthetic

<400> SEQUENCE: 37
acggagaagc acgaacgaaa cgg    23

<210> SEQ ID NO 38
<211> LENGTH: 123
<212> TYPE: DNA
<213> ORGANISM: Artificial Sequence
<220> FEATURE:
<223> OTHER INFORMATION: Synthetic

<400> SEQUENCE: 38
cagggccctt aggtatctgc agacaaggag accctgatat acctggatgt cggaggcatc    60
agttttcgtt cgtgcttctc cgtttccggc ctcgttttgg gtagccgttg atcttacact   120
cat    123

<210> SEQ ID NO 39
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(21)
<223> OTHER INFORMATION: n = A, T, C, or G

<400> SEQUENCE: 39
gnnnnnnnnn nnnnnnnnnn ngg    23

<210> SEQ ID NO 40
<211> LENGTH: 23
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(21)
<223> OTHER INFORMATION: n = A, T, C, or G

<400> SEQUENCE: 40
nnnnnnnnnn nnnnnnnnnn ngg    23

<210> SEQ ID NO 41
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(23)
<223> OTHER INFORMATION: n = A, T, C, or G

<400> SEQUENCE: 41
ggnnnnnnnn nnnnnnnnnn nnngg    25

<210> SEQ ID NO 42
<211> LENGTH: 28
<212> TYPE: PRT
<213> ORGANISM: Artificial Sequence
<220> FEATURE:

<223> OTHER INFORMATION: Synthetic

<400> SEQUENCE: 42

Ala Ala Gln Ser His Leu Pro Ala Thr Arg Pro Glu Thr Glu Lys His
1               5                   10                  15
Glu Arg Asn Gly Cys Leu Arg His Pro Gly Arg Val
            20                  25

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Asp Gln Trp Leu Pro Gln Thr Gly Gln Glu Thr Glu Lys His Lys Arg
1               5                   10                  15
Asn

<210> SEQ ID NO 44
<211> LENGTH: 25
<212> TYPE: DNA
<213> ORGANISM: Artificial Sequence
<220> FEATURE:
<223> OTHER INFORMATION: Synthetic

<400> SEQUENCE: 44
aggcggccca gagccacctg ccagc                                         25

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Tyr Pro Lys Arg Gly Arg Lys Arg Arg Ser Thr Asn Glu Asn
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic

<400> SEQUENCE: 46

Leu Pro Gln Thr Gly Gln Glu Thr Glu Lys His Lys Arg Asn
1               5                   10

<210> SEQ ID NO 47
<211> LENGTH: 14
<212> TYPE: PRT
<213> ORGANISM: Artificial Sequence
<220> FEATURE:
<223> OTHER INFORMATION: Synthetic

<400> SEQUENCE: 47

Lys His Glu Arg Asn Gly Cys Leu Arg His Pro Gly Arg Val
1               5                   10

FIBRILLIN-1 MUTATIONS FOR MODELING NEONATAL PROGEROID SYNDROME WITH CONGENITAL LIPODYSTROPHY

CROSS-REFERENCE TO RELATED APPLICATIONS

This application claims the benefit of U.S. Application No. 62/368,924, filed Jul. 29, 2016, which is herein incorporated by reference in its entirety for all purposes.

REFERENCE TO A SEQUENCE LISTING SUBMITTED AS A TEXT FILE VIA EFS WEB

The Sequence Listing written in file 500985SEQLIST.txt is 184 kilobytes, was created on Jul. 28, 2017, and is hereby incorporated by reference.

BACKGROUND

More than 3000 mutations have been clinically identified in the Fibrillin-1 (FBN1) gene in humans. These mutations have been associated with a variety of conditions, including type I fibrillinopathies, Marfan syndrome, MASS syndrome, isolated ectopia lentis syndrome, thoracic aortic aneurysms, Weill-Marchesani syndrome, geleophysic and acromicric dysplasia, stiff skin syndrome, and neonatal progeroid syndrome with congenital lipodystrophy (NPSCL). Currently available transgenic non-human mammals engineered to have FBN1 mutations do not adequately reflect the symptoms of NPSCL.

SUMMARY

Methods and compositions are provided for modeling neonatal progeroid syndrome with congenital lipodystrophy. In one aspect, the invention provides a non-human mammal whose genome comprises a fibrillin-1 (Fbn1) gene comprising a mutation, whereby expression of the gene results in a C-terminally truncated Fbn1 protein disposing the non-human mammal to develop one or more congenital lipodystrophy-like symptoms of neonatal progeroid syndrome. Optionally, the non-human mammal is heterozygous for the mutation. Optionally, the Fbn1 gene includes an Fbn1 promoter endogenous to the non-human mammal. Optionally, the mutation is a frameshift mutation.

In some non-human mammals, the mutation results in a premature termination codon. Optionally, the premature termination codon is in the penultimate or the final exon of the Fbn1 gene. Optionally, the premature termination codon is in the final exon or is less than about 55 base pairs upstream of the last exon-exon junction in the Fbn1 gene. Optionally, the premature termination codon is less than about 55 base pairs upstream of the last exon-exon junction in the Fbn1 gene. Optionally, the premature termination codon is in the final exon or is less than about 20 base pairs upstream of the last exon-exon junction in the Fbn1 gene. Optionally, the mutation is a splice site mutation resulting in the penultimate exon being skipped. Optionally, the mutation results in a premature termination codon in the last coding exon.

In some non-human mammals, the mutation disrupts a basic amino acid recognition sequence for proprotein convertases of the furin family. In some non-human mammals, the mutation results in ablation of the asprosin C-terminal cleavage product of pro-fibrillin-1. In some non-human mammals, the mutation results in disruption of the asprosin C-terminal cleavage product of pro-fibrillin-1. In some non-human mammals, the premature termination codon results in the encoded protein having a positively charged C-terminus.

In some non-human mammals, the encoded protein (i.e., the C-terminally truncated Fbn1 protein) is truncated at a position corresponding to a position between amino acids 2700 and 2790, between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the encoded protein is optimally aligned with SEQ ID NO: 30. Optionally, the encoded protein is truncated such that the last amino acid is at a position corresponding to amino acid 2737, amino acid 2738, or amino acid 2755 in SEQ ID NO: 30 when the encoded protein is optimally aligned with SEQ ID NO: 30.

In some non-human mammals, the encoded protein (i.e., the C-terminally truncated Fbn1 protein) has a C-terminus consisting of the sequence set forth in SEQ ID NO: 8, 42, or 43. In some non-human mammals, the encoded protein has a C-terminus consisting of the sequence set forth in SEQ ID NO: 8, 42, 43, 45, 46, or 47. Optionally, the encoded protein is truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43. Optionally, the encoded protein is truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43 or 46. Optionally, the encoded protein is truncated such that the last amino acid is at a position corresponding to amino acid 2738 in SEQ ID NO: 30 when the encoded protein is optimally aligned with SEQ ID NO: 30, and the C-terminus of the encoded protein consists of the sequence set forth in SEQ ID NO: 8. Optionally, the encoded protein is truncated such that the last amino acid is at a position corresponding to amino acid 2738 in SEQ ID NO: 30 when the encoded protein is optimally aligned with SEQ ID NO: 30, and the C-terminus of the encoded protein consists of the sequence set forth in SEQ ID NO: 8 or 45. Optionally, the encoded protein is truncated such that the last amino acid is at a position corresponding to amino acid 2755 in SEQ ID NO: 30 when the encoded protein is optimally aligned with SEQ ID NO: 30, and the C-terminus of the encoded protein consists of the sequence set forth in SEQ ID NO: 42. Optionally, the encoded protein is truncated such that the last amino acid is at a position corresponding to amino acid 2755 in SEQ ID NO: 30 when the encoded protein is optimally aligned with SEQ ID NO: 30, and the C-terminus of the encoded protein consists of the sequence set forth in SEQ ID NO: 42 or 47.

In some non-human mammals, the Fbn1 gene comprises a mutation in the penultimate exon. Optionally, the penultimate exon of the Fbn1 gene comprises mutations corresponding to the mutations in SEQ ID NO: 26, 27, or 28 relative to the wild type mouse Fbn1 penultimate exon sequence set forth in SEQ ID NO: 25 when the penultimate exon is optimally aligned with SEQ ID NO: 26, 27, or 28.

In some non-human mammals, all or part of the Fbn1 gene has been deleted and replaced with an orthologous human FBN1 gene sequence. Optionally, the mutation resulting in a C-terminal truncation of the encoded protein is located in the orthologous human FBN1 gene sequence.

Optionally, the orthologous human FBN1 gene sequence is located at the endogenous non-human mammal Fbn1 locus.

In some non-human mammals, the protein encoded by the mutated Fbn1 gene consists of the sequence set forth in SEQ ID NO: 31, 32, or 33.

In some non-human mammals, the mammal is a rodent. Optionally, the rodent is a rat or a mouse.

In some non-human mammals, the mammal is a mouse. In some non-human mammals or mice, the mutation comprises an insertion or deletion in exon 64 of the endogenous mouse Fbn1 gene that causes a −1 frameshift and results in a premature termination codon at the 3' end of exon 64 or the 5' end of exon 65. Optionally, the mutation comprises an insertion in exon 64 that causes a −1 frameshift and results in a premature termination codon at the 5' end of exon 65. Optionally, the insertion is between positions corresponding to positions 8179 and 8180 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is optimally aligned with SEQ ID NO: 20. Optionally, the mutation comprises an insertion or deletion in exon 64 that causes a −1 frameshift and results in a premature termination codon at the 3' end of exon 64. Optionally, the mutation comprises an insertion between positions corresponding to positions 8209 and 8210 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20. Optionally, the mutation comprises a deletion starting at a position corresponding to position 8161 in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20. Optionally, the C-terminally truncated Fbn1 protein has a positively charged C-terminus.

In some non-human mammals, the symptoms comprise one or more of the following: decreased body weight, decreased lean mass, decreased fat mass, decreased body fat percentage, increased food intake normalized by body weight, and increased kyphosis. In some non-human mammals, the symptoms comprise one or more of the following: decreased body weight, decreased lean mass, decreased fat mass, decreased white adipose tissue normalized by body weight, decreased white adipose tissue in combination with preserved brown adipose tissue normalized by body weight, decreased body fat percentage, increased food intake normalized by body weight, and increased kyphosis. Optionally, the non-human mammal has one or more of the following: normal glucose tolerance, normal serum cholesterol levels, normal serum triglyceride levels, and normal serum non-esterified fatty acid levels. Optionally, the non-human mammal has one or more of the following: increased metabolic rate, improved insulin sensitivity, normal glucose tolerance, normal serum cholesterol levels, normal serum triglyceride levels, and normal serum non-esterified fatty acid levels. Optionally, the symptoms comprise at least one of decreased fat mass and decreased body fat percentage and at least one of normal glucose tolerance, normal serum cholesterol levels, normal serum triglyceride levels, and normal serum non-esterified fatty acid levels. Optionally, the symptoms comprise decreased fat mass, decreased body fat percentage, normal glucose tolerance, normal serum cholesterol levels, normal serum triglyceride levels, and normal serum non-esterified fatty acid levels. Optionally, the symptoms comprise decreased white adipose tissue normalized by body weight and at least one of improved insulin sensitivity, normal glucose tolerance, normal serum cholesterol levels, normal serum triglyceride levels, and normal serum non-esterified fatty acid levels. Optionally, the symptoms comprise decreased white adipose tissue normalized by body weight and improved insulin sensitivity.

In another aspect, the invention provides a method of making any of the non-human mammals described herein, comprising: (a) contacting the genome of a non-human mammal pluripotent cell that is not a one-cell stage embryo with: (i) a Cas9 protein; and (ii) a first guide RNA that hybridizes to a first guide RNA recognition sequence within a target genomic locus in the Fbn1 gene, wherein the Fbn1 gene is modified to comprise the mutation resulting in a C-terminal truncation of the encoded protein; (b) introducing the modified non-human mammal pluripotent cell into a host embryo; and (c) implanting the host embryo into a surrogate mother to produce a genetically modified F0 generation non-human mammal in which the Fbn1 gene is modified to comprise the mutation resulting in a C-terminal truncation of the encoded protein, wherein the mutation produces congenital lipodystrophy-like symptoms in the F0 generation non-human mammal. Optionally, the pluripotent cell is an embryonic stem (ES) cell.

In some methods, step (a) further comprises contacting the genome of the non-human mammal pluripotent cell with a second guide RNA that hybridizes to a second guide RNA recognition sequence within the target genomic locus in the Fbn1 gene. In some methods, the method further comprises selecting a modified non-human mammal pluripotent cell after step (a) and before step (b), wherein the modified non-human mammal pluripotent cell is heterozygous for the mutation resulting in a C-terminal truncation of the encoded protein.

In some methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus. Optionally, the exogenous repair template further comprises a nucleic acid insert flanked by the 5' homology arm and the 3' homology arm. Optionally, the nucleic acid insert is homologous or orthologous to the target genomic locus. Optionally, the exogenous repair template is between about 50 nucleotides to about 1 kb in length. Optionally, the exogenous repair template is between about 80 nucleotides to about 200 nucleotides in length. Optionally, the exogenous repair template is a single-stranded oligodeoxynucleotide.

In another aspect, the invention provides a method of making any of the non-human mammals described herein, comprising: (a) contacting the genome of a non-human mammal one-cell stage embryo with: (i) a Cas9 protein; and (ii) a first guide RNA that hybridizes to a first guide RNA recognition sequence within a target genomic locus in the Fbn1 gene, wherein the Fbn1 gene is modified to comprise the mutation resulting in a C-terminal truncation of the encoded protein; and (b) implanting the modified non-human mammal one-cell stage embryo into a surrogate mother to produce a genetically modified F0 generation non-human mammal in which the Fbn1 gene is modified to comprise the mutation resulting in a C-terminal truncation of the encoded protein, wherein the mutation produces congenital lipodystrophy-like symptoms in the F0 generation non-human mammal.

In some methods, step (a) further comprises contacting the genome of the non-human one-cell stage embryo with a second guide RNA that hybridizes to a second guide RNA recognition sequence within the target genomic locus in the Fbn1 gene. In some methods, the method further comprises selecting a modified non-human mammal one-cell stage embryo after step (a) and before step (b), wherein the modified non-human one-cell stage embryo is heterozygous for the mutation resulting in a C-terminal truncation of the encoded protein.

In some methods, the contacting step (a) further comprises contacting the genome with an exogenous repair template comprising a 5' homology arm that hybridizes to a 5' target sequence at the target genomic locus and a 3' homology arm that hybridizes to a 3' target sequence at the target genomic locus. Optionally, the exogenous repair template further comprises a nucleic acid insert flanked by the 5' homology arm and the 3' homology arm. Optionally, the nucleic acid insert is homologous or orthologous to the target genomic locus. Optionally, the exogenous repair template is between about 50 nucleotides to about 1 kb in length. Optionally, the exogenous repair template is between about 80 nucleotides to about 200 nucleotides in length. Optionally, the exogenous repair template is a single-stranded oligodeoxynucleotide.

In another aspect, the invention provides a method of screening a compound for activity for ameliorating congenital lipodystrophy-like symptoms, comprising: (a) contacting any subject non-human mammal described above with the compound; and (b) determining the presence of congenital lipodystrophy-like symptoms of the subject non-human mammal relative to a control non-human mammal not contacted with the compound, wherein the control non-human mammal comprises the same Fbn1 mutation as the subject non-human mammal; whereby activity for ameliorating congenital lipodystrophy-like symptoms is identified by decreased appearance of congenital lipodystrophy-like symptoms in the subject non-human mammal compared with the control non-human mammal.

In some methods, the symptoms comprise one or more of the following: decreased body weight, decreased lean mass, decreased fat mass, decreased body fat percentage, increased food intake normalized by body weight, and increased kyphosis. Optionally, the symptoms comprise at least one of decreased fat mass and decreased body fat percentage. Optionally, the symptoms comprise decreased fat mass and decreased body fat percentage. In some methods, the symptoms comprise one or more of the following: decreased body weight, decreased lean mass, decreased fat mass, decreased white adipose tissue normalized by body weight, decreased white adipose tissue in combination with preserved brown adipose tissue normalized by body weight, decreased body fat percentage, increased food intake normalized by body weight, and increased kyphosis. Optionally, the symptoms comprise decreased white adipose tissue normalized by body weight.

BRIEF DESCRIPTION OF THE FIGURES

FIG. 3 shows the nucleotide sequence (and encoded amino acid sequence) of a region in the penultimate exon of the wild type human FBN1 gene and the nucleotide and amino acid sequences for the corresponding regions in a mutant human FBN1 gene variant associated with neonatal progeroid syndrome with congenital lipodystrophy, a wild-type mouse Fbn1 gene, and an engineered mouse Fbn1 gene variant MAID 8502. FIG. 3 also shows the encoded amino acid sequence of a region in the penultimate exon of the mouse Fbn1 gene for the expected MAID 8502 variant and the MAID 8520 variant that was generated. The forward slash in the amino acid sequences between the "R" and the "S" indicates the furin cleavage site.

FIG. 8A shows body weight of wild type mice and Fbn1 gene variant MAID 8520 heterozygous mice on either a 21% fat breeder diet or a 60% high-fat diet. FIG. 8B shows fat mass (grams of fat mass and percentage of fat mass) of wild type mice and Fbn1 gene variant MAID 8520 heterozygous mice on either a 21% fat breeder diet or a 60% high-fat diet as measured by ECHOMRI™. FIG. 8C shows lean mass (grams of lean mass and percentage of lean mass) of wild type mice and Fbn1 gene variant MAID 8520 heterozygous mice on either a 21% fat breeder diet or a 60% high-fat diet as measured by ECHOMRI™. All mice were 31 weeks of age. Mice were on the 60% high-fat diet for 22 weeks at the time of scan. Asterisks indicate $p<0.0001$ by unpaired t-test.

FIGS. 9A-9C show assays related to glucose homeostasis in male mice. FIG. 9A shows body weight for male wild type mice and Fbn1 gene variant MAID 8520 heterozygous mice on a chow diet. FIG. 9B shows overnight fasting glucose for male wild type mice and Fbn1 gene variant MAID 8520 heterozygous mice on a chow diet. FIG. 9C shows oral glucose tolerance for male wild type mice and Fbn1 gene variant MAID 8520 heterozygous mice on a chow diet.

FIGS. 9D-9F show assays related to glucose homeostasis in female mice. FIG. 9D shows body weight for female wild type mice and Fbn1 gene variant MAID 8520 heterozygous mice on a chow diet. FIG. 9E shows overnight fasting glucose for female wild type mice and Fbn1 gene variant MAID 8520 heterozygous mice on a chow diet. FIG. 9F shows oral glucose tolerance for female wild type mice and Fbn1 gene variant MAID 8520 heterozygous mice on a chow diet.

FIGS. 10A-10C show assays related to circulating lipids in male mice. FIG. 10A shows serum cholesterol levels for male wild type mice and Fbn1 gene variant MAID 8520 heterozygous mice on a chow diet. FIG. 10B shows triglyceride levels for male wild type mice and Fbn1 gene variant MAID 8520 heterozygous mice on a chow diet. FIG. 10C shows non-esterified fatty acids (NEFA-C) levels for male wild type mice and Fbn1 gene variant MAID 8520 heterozygous mice on a chow diet.

FIGS. 10D-10F show assays relating to circulating lipids in female mice. FIG. 10D shows serum cholesterol levels for female wild type mice and Fbn1 gene variant MAID 8520 heterozygous mice on a chow diet. FIG. 10E shows triglyceride levels for female wild type mice and Fbn1 gene variant MAID 8520 heterozygous mice on a chow diet. FIG. 10F shows non-esterified fatty acids (NEFA-C) levels for female wild type mice and Fbn1 gene variant MAID 8520 heterozygous mice on a chow diet.

FIGS. 11A-11G show terminal liver and fat pad weights relative to body weights. FIG. 11A shows the body weights for 34 week-old female Fbn1 gene variant MAID 8520 heterozygous mice on a chow diet. FIGS. 11B-11D show the raw liver, brown adipose tissue (BAT) and visceral white adipose tissue (WAT) weights for each group. FIGS. 11E-11G show those weights as a percentage of body weight.

FIGS. 12A-12H show metabolic cage data from a Columbia Instruments Oxymax CLAMS system of female Fbn1 gene variant MAID 8520 heterozygous mice placed on a 60% high-fat diet for 12 weeks.

DEFINITIONS

Figures 1, 2:
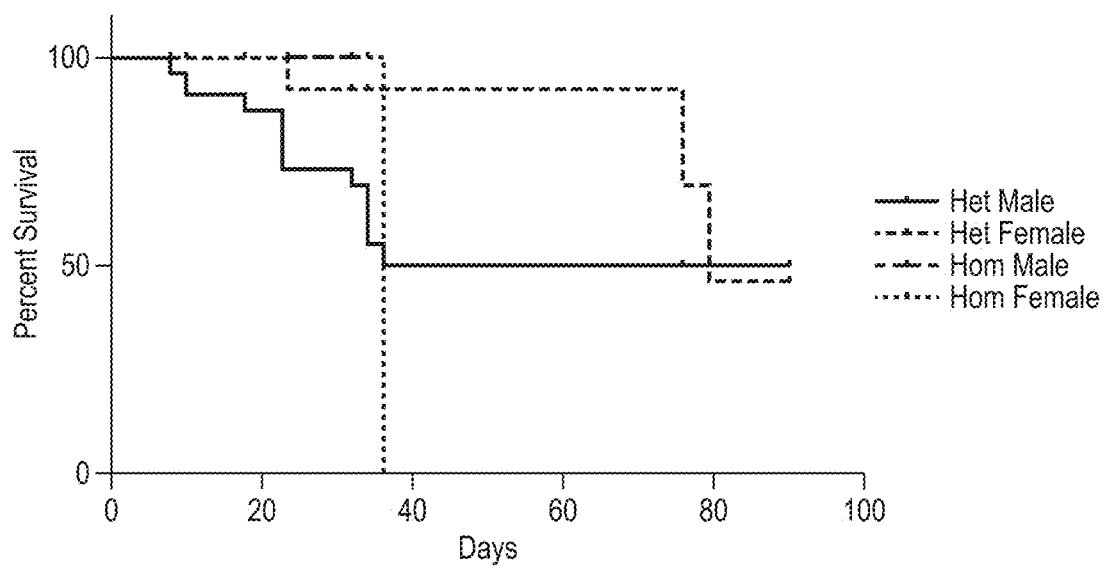
FIG. 1 shows the nucleotide sequence (and encoded amino acid sequence) of a region in the penultimate exon of the wild type human FBN1 gene and the nucleotide and amino acid sequences for the corresponding regions in a mutant human FBN1 gene variant associated with neonatal progeroid syndrome with congenital lipodystrophy, a wild-type mouse Fbn1 gene, and an engineered mouse Fbn1 gene variant MAID 8501. The forward slash in the amino acid sequences between the "R" and the "S" indicates the furin cleavage site.
FIG. 2 shows the percent survival of the male and female F0 founder mice heterozygous or homozygous for the engineered mouse Fbn1 gene variant MAID 8501.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "wild type" includes entities having a structure and/or activity as found in a normal (as contrasted with mutant, diseased, altered, or so forth) state or context. Wild type gene and polypeptides often exist in multiple different forms (e.g., alleles).

The term "isolated" with respect to proteins and nucleic acid includes proteins and nucleic acids that are relatively purified with respect to other bacterial, viral or cellular components that may normally be present in situ, up to and including a substantially pure preparation of the protein and the polynucleotide. The term "isolated" also includes proteins and nucleic acids that have no naturally occurring counterpart, have been chemically synthesized and are thus substantially uncontaminated by other proteins or nucleic acids, or has been separated or purified from most other cellular components with which they are naturally accompanied (e.g., other cellular proteins, polynucleotides, or cellular components).

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

"Codon optimization" generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a polynucleotide encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, an "Fbn1 locus" may refer to the specific location of an Fbn1 gene, Fbn1 sequence, Fbn1-encoding sequence, or Fbn1 position on a chromosome of the genome of an organism that has been identified as to where such a sequence resides. An "Fbn1 locus" may comprise a regulatory element of an Fbn1 gene, including, for example, an enhancer, a promoter, 5' and/or 3' UTR, or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs known in the art (Altschul et al. (1990) *J. Mol. Biol.* 215:403-410; Zhang and Madden (1997) *Genome Res.* 7:649-656) or by using the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, 1981, 2, 482-489).

The methods and compositions provided herein employ a variety of different components. It is recognized throughout the description that some components can have active variants and fragments. Such components include, for example, Cas9 proteins, CRISPR RNAs, tracrRNAs, and guide RNAs. Biological activity for each of these components is described elsewhere herein.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

"Percentage of sequence identity" includes the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "substantial identity" as used herein to refer to shared epitopes includes sequences that contain identical residues in corresponding positions. For example, two sequences can be considered to be substantially identical if at least 70%, 75%, 80%, 85%, 90%, 91%, 92%, 93%, 94%, 95%, 96%, 97%, 98%, 99% or more of their corresponding residues are identical over a relevant stretch of residues. The relevant stretch can be, for example, a complete sequence or can be at least 5, 10, 15, or more residues.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized below.

| Alanine | Ala | A | Nonpolar | Neutral | 1.8 |
|---|---|---|---|---|---|
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

Compositions or methods "comprising" or "including" one or more recited elements may include other elements not specifically recited. For example, a composition that "comprises" or "includes" a protein may contain the protein alone or in combination with other ingredients.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The singular forms of the articles "a," "an," and "the" include plural references unless the context clearly dictates otherwise. For example, the term "a Cas9 protein" or "at least one Cas9 protein" can include a plurality of Cas9 proteins, including mixtures thereof.

Statistically significant means p≤0.05.

DETAILED DESCRIPTION

I. Overview

The present invention provides non-human animals comprising a mutation in the Fbn1 gene to model neonatal progeroid syndrome with congenital lipodystrophy (NPSCL). Also provided are methods of making such non-human animal models. The non-human animal models can be used for screening compounds for activity in inhibiting or reducing NPSCL or ameliorating NPSCL-like symptoms or screening compounds for activity potentially harmful in promoting or exacerbating NPSCL as well as to provide insights in to the mechanism of NPSCL and potentially new therapeutic and diagnostic targets.

II. Non-Human Animal Models of Neonatal Progeroid Syndrome with Congenital Lipodystrophy Provided herein are non-human animals (e.g., non-human mammals, such as rats or mice) comprising a mutation in the Fbn1 gene. Such non-human animals model neonatal progeroid syndrome with congenital lipodystrophy (NPSCL) and exhibit NPSCL-like symptoms (e.g., congenital lipodystrophy-like symptoms).

A. Neonatal Progeroid Syndrome with Congenital Lipodystrophy (NPSCL).

Neonatal progeroid syndrome (NPS) is characterized by congenital, partial lipodystrophy predominantly affecting the face and extremities. O'Neill et al. (2007) *Am. J. Med. Gen. A.* 143A:1421-1430, herein incorporated by reference in its entirety for all purposes. It is also referred to as neonatal progeroid syndrome with congenital lipodystrophy (NPSCL), marfanoid-progeroid syndrome, or marfanoid-progeroid-lipodystrophy (MPL) syndrome. It is characterized by congenital, extreme thinness due to a reduction in subcutaneous adipose tissue, predominantly affecting the face and extremities. See Hou et al. (2009) *Pediatrics and Neonatology* 50:102-109 and O'Neill et al. (2007) *Am. J. Med. Gen. A.* 143A:1421-1430, each of which is herein incorporated by reference in its entirety for all purposes. The phenotype is typically apparent at birth, and even before birth as intrauterine growth retardation, with thin skin and prominent vasculature due to paucity of subcutaneous fat. O'Neill et al. (2007). Patients display a body mass index (BMI) several standard deviations below normal for age, at all ages. O'Neill et al. (2007). Although NPS patients appear progeroid, due to facial dysmorphic features and reduced subcutaneous fat, they do not have the usual features of true progeria such as cataracts, premature greying of hair or insulin resistance. O'Neill et al. (2007). Patients can have normal fasting plasma glucose and insulin levels suggesting that they have normal insulin sensitivity and glucose handling. O'Neill et al. (2007).

The cardinal features of patients with NPSCL include: (1) congenital lipodystrophy; (2) premature birth with an accelerated linear growth disproportionate to the weight gain; and (3) a progeroid appearance with distinct facial features. See, e.g., Takenouchi et al. (2013) *Am. J. Med. Genet. Part A* 161A:3057-3062, herein incorporated by reference in its entirety for al purposes. Jacquinet et al. report the marfanoid-progeroid phenotype as including the following: intrauterine growth retardation and/or preterm birth, senile facial appearance and decreased subcutaneous fat at birth, and progressive marfanoid features. Aortic root dilation, ectopic lentis and dural ectasia can appear with time. Developmental milestones and intelligence appear to be normal. Jacquinet et al. (2014) *Eur. J. Med. Genet.* 57(5):203-234, herein incorporated by reference in its entirety for all purposes.

The phenotype observed in human NPSCL patients, unlike many lipodystrophic syndromes, is a normal metabolic profile in terms of glucose homeostasis and circulating lipids despite having no visceral adipose tissue. Human NPSCL patients have normal glucose homeostasis despite loss of white adipose tissue.

The non-human animal models disclosed herein exhibit NPSCL-like symptoms (e.g., congenital lipodystrophy-like symptoms). Such symptoms can include, for example, one or more of the following: decreased body weight, decreased lean mass, decreased fat mass, decreased white adipose tissue (e.g., normalized by body weight), decreased white adipose tissue in combination with preservation of brown adipose tissue (e.g., normalized by body weight), decreased body fat percentage, increased food intake normalized by body weight, and increased kyphosis. Such symptoms can include, for example, one or more of the following: decreased body weight, decreased lean mass, decreased fat mass, decreased body fat percentage, increased food intake normalized by body weight, and increased kyphosis. Such symptoms can be in combination with one or more of the following: increased metabolic rate, improved insulin sensitivity, normal glucose tolerance, normal serum cholesterol levels, normal serum triglyceride levels, and normal serum non-esterified fatty acid levels. Alternatively, such symptoms can be in combination with one or more of the following: normal glucose tolerance, normal serum cholesterol levels, normal serum triglyceride levels, and normal serum non-esterified fatty acid levels. For example, the symptoms can comprise at least one of decreased fat mass and decreased body fat percentage and at least one of normal glucose tolerance, normal serum cholesterol levels, normal serum triglyceride levels, and normal serum non-esterified fatty acid levels. Alternatively, the symptoms can comprise decreased fat mass, decreased body fat percentage, normal glucose tolerance, normal serum cholesterol levels, normal serum triglyceride levels, and normal serum non-esterified fatty acid levels. Other possible phenotypes include one or more of decreased liver weight, decreased brown adipose tissue (BAT) weight, decreased visceral white adipose tissue (WAT) weight, decreased WAT weight normalized to body weight, elevated metabolic rate normalized to body weight, increased energy expenditure, improved glucose tolerance, and improved insulin sensitivity on high-fat diet. For example, the symptoms can comprise decreased white adipose tissue (e.g., in combination with preserved brown adipose tissue) normalized by body weight in combination with at least one of improved metabolic rate, improved insulin sensitivity, normal glucose tolerance, normal serum cholesterol levels, normal serum triglyceride levels, and normal serum non-esterified fatty acid levels. For example, the symptoms can comprise decreased white adipose tissue (e.g., in combination with preserved brown adipose tissue) normalized by body weight in combination improved insulin sensitivity.

The decrease or increase can be statistically significant. For example, the decrease or increase can be by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100% compared with a control wild type non-human animal.

B. Fbn1 Mutations

NPSCL is associated with mutations in the FBN1 gene in humans. See, e.g., Takenouchi et al. (2013) *Am. J. Med. Genet. Part A* 161A:3057-3062; Graul-Neumann et al. (2010) *Am. J. Med. Genet. A.* 152A(11):2749-2755; Goldblatt et al. (2011) *Am. J. Med. Genet. A* 155A(4):717-720; Horn and Robinson (2011) *Am. J. Med. Genet. A.* 155A(4); 721-724; Jacquinet et al. (2014) *Eur. J. Med. Genet.* 57(5): 203-234; and Romere et al. (2016) *Cell* 165(3):566-579, each of which is herein incorporated by reference in its entirety for all purposes. FBN1 is a 230 kb gene with 65 coding exons (66 total exons) that encode the structural glycoprotein fibrillin-1, a major component of the microfibrils in elastic and non-elastic extracellular matrix. Profibrillin-1 is translated as a 2871-amino-acid long proprotein, which is cleaved at the C-terminus by the protease furin. This generates a 140-amino-acid long C-terminal cleavage product (i.e., asprosin), in addition to mature fibrillin-1 (an extracellular matrix component). An exemplary human fibrillin-1 sequence is assigned UniProt Accession No. P35555.

More than 3000 mutations have been clinically identified in the FBN1 gene. See, e.g., Wang et al. (2016) *Forensic Science International* 261:e1-e4 and www.umd/be/FBN1/, each of which is herein incorporated by reference in its entirety for all purposes. These mutations have been associated with a variety of conditions, including type I fibrillinopathies, Marfan syndrome, MASS syndrome, isolated ectopia lentis syndrome, thoracic aortic aneurysms, Weill-Marchesani syndrome, geleophysic and acromicric dysplasia, stiff skin syndrome, and neonatal progeroid syndrome with congenital lipodystrophy. See, e.g., Davis and Summers (2012) *Mol. Genet. Metab.* 107(4):635-647, herein incorporated by reference in its entirety for all purposes. The most common of these is the autosomal dominant Marfan syndrome comprising ocular, cardiovascular, and skeletal manifestations. See Loeys et al. (2010) *J. Med. Genet.* 47(7):476-485 and Jacquinet et al. (2014) *Eur. J. Med. Genet.* 57(5):203-234, each of which is herein incorporated by reference in its entirety for all purposes. Mutations in classical Marfan syndrome are scattered throughout the FBN1 gene with limited genotype-phenotype relationship. See, e.g., Faivre et al. (2007) *Am. J. Hum. Genet.* 81(3): 454-466 and Jacquinet et al. (2014) *Eur. J. Med. Genet.* 57(5):203-234, each of which is herein incorporated by reference in its entirety for all purposes.

The non-human animal models of NPSCL disclosed herein comprise a mutation in the Fbn1 gene that produces NPSCL-like symptoms (e.g., congenital lipodystrophy-like symptoms) in the non-human animal. The mutations can be in the endogenous Fbn1 gene in the non-human animal. Alternatively, the non-human animal can comprise a humanized Fbn1 locus in which all or part of the endogenous Fbn1 gene has been deleted and replaced with the corresponding orthologous sequence from the human FBN1 gene or other orthologous sequences from other mammals, such as non-human primates. The replacement by orthologous sequence can occur in a particular exon or intron to introduce a mutation from the orthologous sequences. The replacement can also be of all exons, or all exons and introns, or of all exons, introns and flanking sequences including regulatory sequences. Depending on the extent of replacement by orthologous sequences, regulatory sequences, such as a promoter, can be endogenous or supplied by the replacing orthologous sequence.

Preferably, the non-human animal is heterozygous for the mutation. Preferably the mutation results in a C-terminal truncation of the encoded protein. For example, the mutation can cause a frameshift. A frameshift mutation is a sequence change between the translation initiation codon (start codon) and termination codon (stop codon) in which, compared to a reference sequence, translation shifts to another frame. For example, the reading frame can be shifted one nucleotide in the 5' direction (−1 frameshift) or one nucleotide in the 3' direction (+1 frameshift). A protein encoded by a gene with a frameshift mutation will be identical to the protein encoded by the wild type gene from the N-terminus to the frameshift mutation, but different beyond that point. Such frameshifts can result in a premature termination codon. Such premature codons can be, for example, in the penultimate exon or the last exon. Optionally, the premature termination codon is less than about 100 base pairs upstream or less than about 55 base pairs upstream of the last exon-exon junction. For example, the premature termination codon can be less than about 100 base pairs, 90 base pairs, 80 base pairs, 70 base pairs, 60 base pairs, 55 base pairs, 50 base pairs, 40 base pairs, 30 base pairs, 25 base pairs, or 20 base pairs upstream of the last exon-exon junction within the penultimate coding exon. Alternatively, the premature termination codon can be in the last coding exon (e.g., as the result of a splice site mutation resulting in skipping of the penultimate coding exon). Optionally, the premature termination codon is within the last coding exon (e.g., exon 65 of mouse Fbn1) or is in the penultimate exon (e.g., exon 64 of mouse Fbn1), wherein if the premature termination codon is in the penultimate exon, it is less than about 55 base pairs (e.g., less than about 20 base pairs, such as 19 base pairs) upstream of the last exon-exon junction. Optionally, if the premature codon is within the last coding exon, it is less than about 100 base pairs, 90 base pairs, 80 base pairs, 70 base pairs, 60 base pairs, 55 base pairs, 50 base pairs, 40 base pairs, 30 base pairs, 25 base pairs, 20 base pairs, 15 base pairs, or 10 base pairs (e.g., 9 base pairs) downstream of the last exon-exon junction. Optionally, the premature termination codon is between positions corresponding to positions 8150 and 8300, 8160 and 8290, 8170 and 8280, 8180 and 8270, 8190 and 8260, 8200 and 8250, 8210 and 8300, 8210 and 8290, 8210 and 8280, 8210 and 8270, 8210 and 8260, 8210 and 8250, 8200 and 8300, 8200 and 8290, 8200 and 8280, 8200 and 8270, 8200 and 8260, 8200 and 8250, 8150 and 8245, 8160 and 8245, 8170 and 8245, 8180 and 8245, 8190 and 8245, 8200 and 8245, 8150 and 8250, 8160 and 8250, 8170 and 8250, 8180 and 8250, 8190 and 8250, 8200 and 8250, or 8210 and 8245 in the wild type mouse Fbn1 coding sequence set forth in SEQ ID NO: 20 when the Fbn1 gene comprising the mutation is optimally aligned with SEQ ID NO: 20.

The premature termination codon can result in a truncated protein with a positively charged C-terminus. Among the 20 common amino acids, five have a side chain which can be charged. At pH=7, two are negatively-charged (aspartic acid (Asp, D), and glutamic acid (Glu, E)) and three are positively charged (lysine (Lys, K), arginine (Arg, R), and histidine (His, H)). In some cases, the premature termination codon can result in a truncated protein with an extremely positively charged C-terminus (e.g., ETEKHKRN (SEQ ID NO: 34)). Alternatively, the premature termination codon can result in a truncated protein with a less positively charged C-terminus (e.g., ISLRQKPM (SEQ ID NO: 35)).

Optionally, the mutation disrupts a basic amino acid recognition sequence for proprotein convertases of the furin family (RGRKRR (SEQ ID NO: 36)). For example, the mutation can result in a protein truncated upstream of the furin recognition sequence, can mutate the furin recognition sequence, or can result in a frameshift upstream of the furin recognition sequence. Optionally, the mutation is within 100 base pairs of the basic amino acid recognition sequence for proprotein convertases of the furin family. For example, the mutation can be within about 90 base pairs, 80 base pairs, 70 base pairs, 60 base pairs, 50 base pairs, 40 base pairs, or 30 base pairs of the furin recognition sequence. As an example, such mutations can include insertions or deletions of nucleotides resulting in a frameshift in the penultimate exon or the last exon. As another example, such mutations can include donor splice site mutations that result in skipping of the penultimate exon and a subsequent frameshift that results in a premature termination codon in the last exon.

In some non-human animals, the mutation results in disruption or ablation (e.g., heterozygous ablation) of the C-terminal cleavage product (i.e., asprosin) of profibrillin-1. Disruption or ablation of the C-terminal cleavage product can result, for example, from disruption of the basic amino acid recognition sequence for proprotein convertases of the furin family. Alternatively, disruption or ablation of the C-terminal cleavage product can result, for example, from the mutation creating a premature termination codon such that the C-terminal cleavage product is truncated. Disruption of asprosin results in either decreased production of asprosin or production of asprosin with decreased activity. In some non-human animals, the Fbn1 gene comprises a mutation in the penultimate exon. For example, the penultimate exon of the Fbn1 gene can comprise mutations corresponding to the mutations in SEQ ID NO: 26, 27, or 28 (the penultimate exons from MAID alleles 8501, 8520, and 8502, respectively) relative to the penultimate exon from the wild type mouse Fbn1 (SEQ ID NO: 25) when the penultimate exon is optimally aligned with SEQ ID NO: 26, 27, or 28.

In some non-human animals, the Fbn1 protein encoded by the mutated Fbn1 gene is truncated at a position corresponding to a position between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the encoded protein is optimally aligned with SEQ ID NO: 30. For example, the encoded protein can be truncated such that the last amino acid is at a position corresponding to amino acid 2737, amino acid 2738, or amino acid 2755 in the wild type mouse Fbn1 protein set forth in SEQ ID NO: 30 when the encoded protein is optimally aligned with SEQ ID NO: 30. Likewise, the encoded protein can be truncated such that the last amino acid is at a position corresponding to the last amino acid of the truncated Fbn1 proteins encoded by the MAID 8501, 8502, and 8520 Fbn1 variants described herein.

As another example, the encoded protein can have a C-terminus consisting of the sequence set forth in SEQ ID NO: 8, 42, or 43, or the encoded protein can have a C-terminus corresponding to the C-terminus of the proteins encoded by the MAID 8501, 8502, and 8520 Fbn1 variants described herein. For example, the encoded protein can be truncated such that the last amino acid is at a position corresponding to amino acid 2737 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 43. As another example, the encoded protein can be truncated such that the last amino acid is at a position corresponding to amino acid 2738 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 8. As another example, the encoded protein can be truncated such that the last amino acid is at a position corresponding to amino acid 2755 in the wild type mouse Fbn1 protein set forth in SEQ ID NO: 30 when the encoded protein is optimally aligned with SEQ ID NO: 30, and the C-terminus of the encoded protein consists of the sequence set forth in SEQ ID NO: 42. Exemplary truncated Fbn1 proteins include SEQ ID NO: 31, 32 and 33.

An Fbn1 gene refers to any known gene encoding an Fbn1 protein, such as described in Swiss-Prot and GenBank databases, and including variants of these proteins as described in such databases or otherwise having at least 95, 96, 97, 98 or 99% identity to wild type sequences, including hybrids of such genes, and including any such gene or hybrid of such genes modified by a mutation to produce NPSCL-like symptoms (e.g., congenital lipodystrophy-like symptoms) as further described herein. If any variations are present other than residues mutated to produce NPSCL-like symptoms, the variations preferably do not affect coding sequences or if they do affect coding sequences preferably do so by introducing conservative substitutions.

In some of the non-human animals disclosed herein, the endogenous Fbn1 gene is mutated to produce NPSCL-like symptoms. Exemplary mouse Fibrillin-1 sequences are assigned Accession No. NM_007993.2 or UniProt Accession No. Q61554. Exemplary rat Fibrillin-1 sequences are assigned Accession No. NM_031825.1 or UniProt Accession No. Q9WUH8. Other exemplary Fibrillin-1 sequences include Accession Nos. NM_001001771.1 (pig), NM_001287085.1 (dog), and NM_174053.2 (cow). The mouse Fbn1 gene lies on the long arm of chromosome 15 at 15q15-q21.1. Megenis et al. (1991) *Genomics* 11:346-351, herein incorporated by reference in its entirety for all purposes. Like human FBN1, it is a very large gene that is highly fragmented into 65 exons. Pereira et al. (1993) *Hum. Mol. Genet.* 2:961-968, herein incorporated by reference in its entirety for all purposes.

Such mutations in the endogenous Fbn1 gene can correspond with mutations identified in the human FBN1 gene in patients diagnosed with NPSCL as disclosed elsewhere herein. A residue (e.g., nucleotide or amino acid) in an endogenous Fbn1 gene (or protein) can be determined to correspond with a residue in the human FBN1 gene (or protein) by optimally aligning the two sequences for maximum correspondence over a specified comparison window (e.g., the Fbn1 coding sequence), wherein the portion of the polynucleotide (or amino acid) sequence in the comparison window may comprise additions or deletions (i.e., gaps) as compared to the reference sequence (which does not comprise additions or deletions) for optimal alignment of the two sequences (see, e.g., discussion elsewhere herein with regard to sequence identity and complementarity). Two residues correspond if they are located at the same position when optimally aligned.

A specific example of a mutation in a mouse Fbn1 gene that produces NPSCL-like symptoms is c.8207_8208 ins1bp (reference sequence NM_007993.2 or reference sequence SEQ ID NO: 20). Some non-human animals disclosed herein comprise an Fbn1 gene with a mutation corresponding to c.8207_8208 ins1bp in NM_007993.2 or SEQ ID NO: 20 when the Fbn1 gene optimally aligned with NM_007933.2 or SEQ ID NO: 20. A specific example of mutations within a mouse Fbn1 gene sequence that can produce NPSCL-like symptoms are the mutations in SEQ ID NO: 21, 22, or 23 relative to SEQ ID NO: 20 (mouse WT Fbn1 cDNA), or the mutations in SEQ ID NO: 26, 27, or 28 relative to SEQ ID NO: 25 (penultimate exon of WT Fbn1 cDNA). Specific examples of mutated mouse Fbn1 proteins that can produce NPSCL-like symptoms are SEQ ID NOS: 31, 32, and 33.

In other non-human animals disclosed herein, all or part of the endogenous Fbn1 gene has been deleted and replaced with the corresponding sequence from the human Fbn1 gene. For example, the human Fbn1 gene sequence can be located at the endogenous Fbn1 locus (i.e., all or part of the endogenous Fbn1 locus has been humanized). In such non-human animals, the corresponding sequence of the human FBN1 gene can include a mutation that produces NPSCL-like symptoms. An exemplary human FBN1 cDNA sequence is assigned Accession No. NM_000138.3, and an exemplary human Fibrillin-1 protein sequence is assigned UniProt Accession No. P35555. When specific mutation positions in the human FBN1 gene are referred to herein, they are in reference to FBN1 cDNA NM_000138.3 (Ensembl transcript FBN1-201=ENST00000316623). Likewise, when human FBN1 gene introns or exons are referred to herein, they are in reference to reference sequence NM_000138.3 and ENST00000316623, with exon numbering starting from exon 2 according to the localization of the ATG start codon (i.e., exon numbering starting from the first coding exon). Numbering of mutation positions is based on the Human Genome Variation Society (HGVS) sequence variant nomenclature (varnomen.hgvs.org). The prefix "c" indicates that the reference sequence is a coding DNA reference sequence (based on a protein coding transcript). Numbering starts with "c.1" at the "A" of the "ATG" translation initiation (start) codon and ends with the last nucleotide of the translation termination (stop) codon (i.e., TAA, TAG, or TGA). Nucleotides at the 5' end of an intron are numbered relative to the last nucleotide of the directly upstream exon, followed by a "+" (plus) and their position in to the intron (e.g., c.87+1). Nucleotides at the 3' end of an intron are numbered relative to the first nucleotide of the directly downstream exon, followed by a "−" (minus) and their position out of the intron (e.g., c.88-3). Substitution mutations where, compared to the reference sequence, one nucleotide is replaced by one other nucleotide are in the format of "prefix" "position_substituted" "reference_nucleotide">"new_nucleotide" (e.g., c.123A>G indicates that the reference sequence is a coding DNA reference sequence and the "A" at position 123 in the reference sequence is substituted with a "G." Deletion mutations where, compared to a reference sequence, one or more nucleotides are not present are in the format of "prefix" "position(s)_deleted" "del" (e.g., c.123_127del indicates that nucleotides at positions 123-127 in the coding DNA reference sequence are deleted). Insertion mutations where, compared to the reference sequence, one or more nucleotides are inserted and where the insertion is not a copy of a sequence immediately 5' are in the format "prefix" "positions_flanking" "ins" "inserted_sequence" (e.g., c.123_124insAGC indicates that the sequence AGC is inserted between positions 123 and 124 of the coding DNA reference sequence). Insertion/deletion (indel) mutations where, compared to a reference sequence, one or more nucleotides are replaced by one or more other nucleotides (and wherein the mutation is not a substitution, inversion, or conversion) are in the format "prefix" "position(s)_deleted" "delins" "inserted_sequence" (e.g., c.123_127delinsAG indicates that the sequence between positions 123 and 127 was deleted and replaced with the sequence "AG" in the coding DNA reference sequence).

Preferably, the mutation is between c.8100 and c.8300 or c.8150 and c.8250 in the human FBN1 sequence or corresponding positions in a non-human Fbn1 sequence when optimally aligned with the human FBN1 sequence. Exemplary mutations in the human FBN1 gene include insertions or deletions of nucleotides resulting in a frameshift. See, e.g., Takenouchi et al. (2013) *Am. J. Med. Genet. Part A* 161A:3057-3062; Graul-Neumann et al. (2010) *Am. J. Med. Genet. A.* 152A(11):2749-2755; and Goldblatt et al. (2011) *Am. J. Med. Genet. A* 155A(4):717-720, each of which is herein incorporated by reference in its entirety for all purposes. One example of such a mutation in the human FBN1 gene is c.8155_8156del. This is a deletion of two base pairs in coding exon 64 (the penultimate exon), which causes a frameshift with a subsequent premature termination codon 17 codons downstream of p.Lys2719. See, e.g., Graul-Neumann et al. (2010) *Am. J. Med. Genet. A.* 152A(11): 2749-2755. Another example of such a mutation in the human FBN1 gene that results in a frameshift resulting in the same premature termination codon is c.8156_8175del. See, e.g., Goldblatt et al. (2011) *Am. J. Med. Genet. A* 155A(4): 717-720. Yet another example of such a mutation in the human FBN1 gene that results in a frameshift resulting in the same premature termination codon is c.8175_8182del. See, e.g., Takenouchi et al. (2013) *Am. J. Med. Genet. Part A* 161A:3057-3062. Another example of such a mutation in the human FBN1 gene resulting in a premature termination codon in coding exon 64 is c.8206_8207insA. See, e.g., Romere et al. (2016) *Cell* 165(3):566-579. The non-human animals described herein can comprise an Fbn1 gene with mutations corresponding to any of these mutations when the Fbn1 gene sequence is optimally aligned with the human FBN1 gene corresponding to the cDNA sequence set forth in Accession No. NM_000138.3.

Other exemplary mutations in the human FBN1 gene include donor splice site mutations that result in skipping of the penultimate exon (exon 64) and a subsequent frameshift that results in a premature termination codon in the last exon (exon 65). See, e.g., Horn and Robinson (2011) *Am. J. Med.*

Genet. A. 155A(4):721-724 and Jacquinet et al. (2014) Eur. J. Med. Genet. 57(5):203-234, each of which is herein incorporated by reference in its entirety for all purposes. One example of such a mutation in the human FBN1 gene is c.8226+1G>A. See, e.g., Jacquinet et al. (2014) Eur. J. Med. Genet. 57(5):203-234. Another example of such a mutation in the human FBN1 gene is c.8226+1G>T. See, e.g., Horn and Robinson (2011) Am. J. Med. Genet. A. 155A(4):721-724 and Romere et al. (2016) Cell 165(3):566-579. These mutations affect the splice-donor site of intron 64, changing the highly conserved GT dinucleotide, and lead to skipping of coding exon 64 and the production of a stable mRNA that should allow synthesis of a truncated profibrillin-1 in which the C-terminal furin cleavage site is altered. Skipping of exon 64 results in a frameshift at the beginning of coding exon 65 and the generation of a premature termination codon at the ninth downstream codon.

The non-human animals described herein can comprise an Fbn1 gene with mutations corresponding to any of these mutations when the Fbn1 gene sequence is optimally aligned with the human FBN1 gene sequence corresponding to the cDNA sequence set forth in Accession No. NM_000138.3. Likewise, the non-human animals described herein can comprise an Fbn1 gene with mutations such that the mutant Fbn1 gene encodes an Fbn1 protein corresponding to any of the human FBN1 proteins encoded by any of the mutant human FBN1 genes described herein. Similarly, the encoded protein can be truncated such that the last amino acid is at a position corresponding to the last amino acid of the truncated Fbn1 proteins encoded by any of the mutant human FBN1 genes described herein, and/or can have a C-terminus identical to the C-terminus of the truncated Fbn1 proteins encoded by any of the mutant human FBN1 genes described herein.

Certain exemplary mutant Fbn1 alleles are mutant mouse Fbn1 alleles. For example, the mutation in the mutant mouse Fbn1 allele can comprise an insertion or deletion in the penultimate exon (exon 64) that causes a −1 frameshift and results in a premature termination codon at the 3' end of the penultimate exon (exon 64) or the 5' end of the final exon (exon 65) of Fbn1.

As one example, the mutation can comprise an insertion or a deletion in exon 64 that causes a −1 frameshift and results in a premature termination codon at the 5' end of exon 65, as in the MAID 8520 allele described in Example 2 and set forth in SEQ ID NO: 22. Optionally, the insertion or deletion is upstream of a position corresponding to position 8241 (e.g., an insertion between positions corresponding to positions 8179 and 8180) in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is optimally aligned with SEQ ID NO: 20.

As another example, the mutation can comprise an insertion or deletion in the penultimate exon (exon 64) that causes a −1 frameshift and results in a premature termination codon at the 3' end of the penultimate exon (exon 64), as in the MAID 8501 allele described in Example 1 and set forth in SEQ ID NO: 21 or the MAID 8502 allele described in Example 2 and set forth in SEQ ID NO: 23. Optionally, the insertion or deletion is upstream of a position corresponding to position 8214 (e.g., an insertion between positions corresponding to positions 8209 and 8210, or a deletion starting at a position corresponding to position 8161) in the wild type mouse Fbn1 coding sequence set forth in SEQ ID NO: 20 when the Fbn1 gene comprising the mutation is optimally aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is optimally aligned with SEQ ID NO: 20.

One exemplary mutant mouse Fbn1 allele is the MAID 8501 allele described in Example 1 and set forth in SEQ ID NO: 21. The protein encoded by the MAID 8501 allele is set forth in SEQ ID NO: 31. Using NM_007993.2 as a reference sequence, the mutation in this mutant Fbn1 allele is c.8213_8214delinsACT. This mutation, which was created by inserting an A between c.8212 and 8213 and making a G>T substitution at c.8214, results in a premature termination codon in the penultimate exon (exon 64) of Fbn1, 19 nucleotides upstream of the boundary between exons 64 and 65. The mutation is within the last 50 nucleotides (the last 24 nucleotides) of the penultimate exon and is predicted to escape mRNA nonsense-mediated decay (NMD), leading to expression of a mutant, truncated profibrillin protein.

Another exemplary mouse allele is the MAID 8502 allele described in Example 2 and set forth in SEQ ID NO: 23. The protein encoded by the MAID 8502 allele is set forth in SEQ ID NO: 33. This is a mutant Fbn1 allele corresponding to the human c.8155_8156del Fbn1 allele, which has a deletion of two base pairs in coding exon 64 (the penultimate exon) causing a frameshift with a subsequent premature termination codon 17 codons downstream of p.Lys2719. In the MAID 8502 allele, the deletion of two base pairs is 71 nucleotides upstream of the boundary between exons 64 and 65. The mutation results in a premature termination codon in the penultimate exon (exon 64) of mouse Fbn1, 19 nucleotides upstream of the boundary between exons 64 and 65.

Another exemplary mouse allele is the MAID 8520 allele described in Example 2 and set forth in SEQ ID NO: 22. The protein encoded by the MAID 8520 allele is set forth in SEQ ID NO: 32. Using NM_007993.2 as a reference sequence, the mutation in this mutant Fbn1 allele is 8179_8180insAG-GCGGCCCAGAGCCACCTGCCAGC. This mutation was created through a 25-bp insertion (inserted sequence set forth in SEQ ID NO: 44) in the penultimate exon (exon 64), 54 nucleotides upstream of the boundary between exons 64 and 65. It results in a frameshift in the penultimate exon (exon 64) of mouse Fbn1. The mutation results in a premature termination codon in the final exon (exon 65) of mouse Fbn1, 9 nucleotides downstream of the boundary between exons 64 and 65.

Each of the above exemplary mouse Fbn1 alleles results in a frameshift mutation in the penultimate exon (exon 64) of the mouse Fbn1 gene. Each frameshift mutation results in a premature termination codon within either the 3' end of the penultimate exon (exon 64) or the 5' end of the final exon (exon 65) of the mouse Fbn1 gene. Because each mutation results in a premature termination codon, each mutation disrupts or ablates the C-terminal cleavage product (i.e., asprosin) of profibrillin-1 because the C-terminal cleavage product, if produced, will necessarily be truncated as well. In addition, each of the above exemplary mouse Fbn1 alleles results in a positively charged C-terminal end due to a greater number of lysines, arginines, and histidines relative to aspartic acids and glutamic acids. The last 14 amino acids of the Fbn1 proteins encoded by the MAID 8501, MAID 8502, and MAID 8520 alleles, which are set forth in SEQ ID NOS: 45, 46, and 47, respectively.

C. Non-Human Animals

Any suitable non-human animal can be used as a model of NPSCL as disclosed herein. Such non-human animals are preferably mammals, such as rodents (e.g., rats, mice, and hamsters). Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). The term "non-human" excludes humans.

Mice employed in the non-human animal models disclosed herein can be from any strain, including, for example, from a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice have a strain comprising 50% BALB/c, 25% C57BL/6, and 25% 129. Alternatively, the mice can comprise a strain or strain combination that excludes BALB/c.

Examples of 129 strains include 129P1, 129P2, 129P3, 129X1, 129S1 (e.g., 129S1/SV, 129S1/Sv1m), 129S2, 129S4, 129S5, 12959/SvEvH, 129S6 (129/SvEvTac), 129S7, 129S8, 129T1, and 129T2. See, e.g., Festing et al. (1999) *Mammalian Genome* 10(8):836, herein incorporated by reference in its entirety for all purposes. Examples of C57BL strains include C57BL/A, C57BL/An, C57BL/GrFa, C57BL/Ka1_wN, C57BL/6, C57BL/6J, C57BL/6ByJ, C57BL/6NJ, C57BL/10, C57BL/10ScSn, C57BL/10Cr, and C57BL/Ola. Mice employed in the non-human animal models provided herein can also be from a mix of an aforementioned 129 strain and an aforementioned C57BL/6 strain (e.g., 50% 129 and 50% C57BL/6). Likewise, mice employed in the non-human animal models provided herein can be from a mix of aforementioned 129 strains or a mix of aforementioned BL/6 strains (e.g., the 129S6 (129/SvEvTac) strain).

Rats employed in the non-human animal models provided herein can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be from a strain derived from a mix of two or more strains recited above. For example, the rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. In some cases, the rats are from an inbred rat strain. See, e.g., US 2014/0235933 A1, herein incorporated by reference in its entirety for all purposes.

II. Generation of Animal Models of Neonatal Progeroid Syndrome with Congenital Lipodystrophy A. Generating Fbn1 Mutations in Cells Various methods are provided for modifying an Fbn1 gene in a genome within a cell (e.g., a pluripotent cell or a one-cell stage embryo) through use of nuclease agents and/or exogenous repair templates. The methods can occur in vitro, ex vivo, or in vivo. The nuclease agent can be used alone or in combination with an exogenous repair template. Alternatively, the exogenous repair template can be used alone or in combination with a nuclease agent.

Repair in response to double-strand breaks (DSBs) occurs principally through two conserved DNA repair pathways: non-homologous end joining (NHEJ) and homologous recombination (HR). See Kasparek & Humphrey (2011) *Seminars in Cell & Dev. Biol.* 22:886-897, herein incorporated by reference in its entirety for all purposes. NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break.

Repair of a target nucleic acid (e.g., the Fbn1 gene) mediated by an exogenous repair template can include any process of exchange of genetic information between the two polynucleotides. For example, NHEJ can also result in the targeted integration of an exogenous repair template through direct ligation of the break ends with the ends of the exogenous repair template (i.e., NHEJ-based capture). Such NHEJ-mediated targeted integration can be preferred for insertion of an exogenous repair template when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site (beyond the overhangs created by Cas-mediated cleavage) is not needed, which can be beneficial when attempting targeted insertion into organisms that have genomes for which there is limited knowledge of the genomic sequence. The integration can proceed via ligation of blunt ends between the exogenous repair template and the cleaved genomic sequence, or via ligation of sticky ends (i.e., having 5' or 3' overhangs) using an exogenous repair template that is flanked by overhangs that are compatible with those generated by the Cas protein in the cleaved genomic sequence. See, e.g., US 2011/020722, WO 2014/033644, WO 2014/089290, and Maresca et al. (2013) *Genome Res.* 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

Repair can also occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Targeted genetic modifications to an Fbn1 gene in a genome can be generated by contacting a cell with an exogenous repair template comprising a 5' homology arm that hybridizes to a 5' target sequence at a target genomic locus within the Fbn1 gene and a 3' homology arm that hybridizes to a 3' target sequence at the target genomic locus within the Fbn1 gene. The exogenous repair template can recombine with the target genomic locus to generate the targeted genetic modification to the Fbn1 gene. Such methods can result, for example, in an Fbn1 gene modified to comprise a mutation resulting in a C-terminal truncation of the encoded protein. Examples of exogenous repair templates are disclosed elsewhere herein.

Targeted genetic modifications to an Fbn1 gene in a genome can also be generated by contacting a cell with a nuclease agent that induces one or more nicks or double-strand breaks at a recognition sequence at a target genomic locus within the Fbn1 gene. Such methods can result, for example, in an Fbn1 gene modified to comprise a mutation resulting in a C-terminal truncation of the encoded protein. Examples and variations of nuclease agents that can be used in the methods are described elsewhere herein.

For example, targeted genetic modifications to an Fbn1 gene in a genome can be generated by contacting a cell with a Cas protein and one or more guide RNAs that hybridize to one or more guide RNA recognition sequences within a target genomic locus in the Fbn1 gene. For example, such methods can comprise contacting a cell with a Cas protein and a guide RNA that hybridizes to a guide RNA recognition sequence within the Fbn1 gene. The Cas protein and the guide RNA form a complex, and the Cas protein cleaves the guide RNA recognition sequence. Cleavage by the Cas9 protein can create a double-strand break or a single-strand break (e.g., if the Cas9 protein is a nickase). Such methods can result, for example, in an Fbn1 gene modified to comprise a mutation resulting in a C-terminal truncation of the encoded protein. Examples and variations of Cas9 proteins and guide RNAs that can be used in the methods are described elsewhere herein.

Optionally, the cell can be further contacted with one or more additional guide RNAs that hybridize to additional guide RNA recognition sequences within the target genomic locus in the Fbn1 gene. By contacting the zygote with one or more additional guide RNAs (e.g., a second guide RNA that hybridizes to a second guide RNA recognition sequence), cleavage by the Cas protein can create two or more double-strand breaks or two or more single-strand breaks (e.g., if the Cas protein is a nickase).

Optionally, the cell can additionally be contacted with one or more exogenous repair templates which recombine with the target genomic locus in the Fbn1 gene to generate a targeted genetic modification. Examples and variations of exogenous repair templates that can be used in the methods are disclosed elsewhere herein.

The Cas protein, guide RNA(s), and exogenous repair template(s) can be introduced into the cell in any form and by any means as described elsewhere herein, and all or some of the Cas protein, guide RNA(s), and exogenous repair template(s) can be introduced simultaneously or sequentially in any combination.

In some such methods, the repair of the target nucleic acid (e.g., the Fbn1 gene) by the exogenous repair template occurs via homology-directed repair (HDR). Homology-directed repair can occur when the Cas protein cleaves both strands of DNA in the Fbn1 gene to create a double-strand break, when the Cas protein is a nickase that cleaves one strand of DNA in the target nucleic acid to create a single-strand break, or when Cas nickases are used to create a double-strand break formed by two offset nicks. In such methods, the exogenous repair template comprises 5' and 3' homology arms corresponding to 5' and 3' target sequences. The guide RNA recognition sequence(s) or cleavage site(s) can be adjacent to the 5' target sequence, adjacent to the 3' target sequence, adjacent to both the 5' target sequence and the 3' target sequence, or adjacent to neither the 5' target sequence nor the 3' target sequence. Optionally, the exogenous repair template can further comprise a nucleic acid insert flanked by the 5' and 3' homology arms, and the nucleic acid insert is inserted between the 5' and 3' target sequences. For example, the nucleic acid insert can comprise one or more modifications when compared with the wild type non-human animal Fbn1 sequence, or it can comprise all or part of a human FBN1 coding sequence comprising one or more modifications when compared with the wild type human FBN1 sequence. If no nucleic acid insert is present, the exogenous repair template can function to delete the genomic sequence between the 5' and 3' target sequences. Examples of exogenous repair templates are disclosed elsewhere herein.

Alternatively, the repair of the Fbn1 gene mediated by the exogenous repair template can occur via non-homologous end joining (NHEJ)-mediated ligation. In such methods, at least one end of the exogenous repair template comprises a short single-stranded region that is complementary to at least one overhang created by Cas-mediated cleavage in the Fbn1 gene. The complementary end in the exogenous repair template can flank a nucleic acid insert. For example, each end of the exogenous repair template can comprise a short single-stranded region that is complementary to an overhang created by Cas-mediated cleavage in the Fbn1 gene, and these complementary regions in the exogenous repair template can flank a nucleic acid insert. For example, the nucleic acid insert can comprise one or more modifications when compared with the wild type non-human animal Fbn1 sequence, or it can comprise all or part of a human FBN1 coding sequence comprising one or more modifications when compared with the wild type human FBN1 sequence.

Overhangs (i.e., staggered ends) can be created by resection of the blunt ends of a double-strand break created by Cas-mediated cleavage. Such resection can generate the regions of microhomology needed for fragment joining, but this can create unwanted or uncontrollable alterations in the Fbn1 gene. Alternatively, such overhangs can be created by using paired Cas nickases. For example, the cell can be contacted with first and second nickases that cleave opposite strands of DNA, whereby the genome is modified through double nicking. This can be accomplished by contacting a cell with a first Cas protein nickase, a first guide RNA that hybridizes to a first guide RNA recognition sequence within the target genomic locus in the Fbn1 gene, a second Cas protein nickase, and a second guide RNA that hybridizes to a second guide RNA recognition sequence within target genomic locus in the Fbn1 gene. The first Cas protein and the first guide RNA form a first complex, and the second Cas protein and the second guide RNA form a second complex. The first Cas protein nickase cleaves a first strand of genomic DNA within the first guide RNA recognition sequence, the second Cas protein nickase cleaves a second strand of genomic DNA within the second guide RNA recognition sequence, and optionally the exogenous repair template recombines with the target genomic locus in the Fbn1 gene to generate the targeted genetic modification.

The first nickase can cleave a first strand of genomic DNA (i.e., the complementary strand), and the second nickase can cleave a second strand of genomic DNA (i.e., the non-complementary strand). The first and second nickases can be created, for example, by mutating a catalytic residue in the RuvC domain (e.g., the D10A mutation described elsewhere herein) of Cas9 or mutating a catalytic residue in the HNH domain (e.g., the H840A mutation described elsewhere herein) of Cas9. In such methods, the double nicking can be employed to create a double-strand break having staggered ends (i.e., overhangs). The first and second guide RNA recognition sequences can be positioned to create a cleavage site such that the nicks created by the first and second nickases on the first and second strands of DNA create a double-strand break. Overhangs are created when the nicks within the first and second CRISPR RNA recognition sequences are offset. The offset window can be, for example, at least about 5 bp, 10 bp, 20 bp, 30 bp, 40 bp, 50 bp, 60 bp, 70 bp, 80 bp, 90 bp, 100 bp or more. See, e.g., Ran et al. (2013) *Cell* 154:1380-1389; Mali et al. (2013) *Nat. Biotech.* 31:833-838; and Shen et al. (2014) *Nat. Methods* 11:399-404.

B. Nuclease Agents

Any nuclease agent that induces a nick or double-strand break into a desired recognition sequence can be used in the methods and compositions disclosed herein. A naturally occurring or native nuclease agent can be employed so long as the nuclease agent induces a nick or double-strand break in a desired recognition sequence. Alternatively, a modified or engineered nuclease agent can be employed. An "engineered nuclease agent" includes a nuclease that is engineered (modified or derived) from its native form to specifically recognize and induce a nick or double-strand break in the desired recognition sequence. Thus, an engineered nuclease agent can be derived from a native, naturally occurring nuclease agent or it can be artificially created or synthesized. The engineered nuclease can induce a nick or double-strand break in a recognition sequence, for example, wherein the recognition sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a recognition sequence or other DNA can be referred to herein as "cutting" or "cleaving" the recognition sequence or other DNA.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired recognition sequence and hence retain nick or double-strand-break-inducing activity. For example, any of the nuclease agents described herein can be modified from a native endonuclease sequence and designed to recognize and induce a nick or double-strand break at a recognition sequence that was not recognized by the native nuclease agent. Thus, some engineered nucleases have a specificity to induce a nick or double-strand break at a recognition sequence that is different from the corresponding native nuclease agent recognition sequence. Assays for nick or double-strand-break-inducing activity are known and generally measure the overall activity and specificity of the endonuclease on DNA substrates containing the recognition sequence.

The term "recognition sequence for a nuclease agent" includes a DNA sequence at which a nick or double-strand break is induced by a nuclease agent. The recognition sequence for a nuclease agent can be endogenous (or native) to the cell or the recognition sequence can be exogenous to the cell. A recognition sequence that is exogenous to the cell is not naturally occurring in the genome of the cell. The recognition sequence can also be exogenous to the polynucleotides of interest that one desires to be positioned at the target locus. In some cases, the recognition sequence is present only once in the genome of the host cell.

Active variants and fragments of the exemplified recognition sequences are also provided. Such active variants can comprise at least 65%, 70%, 75%, 80%, 85%, 90%, 91%, 92%, 93%, 94%, 95%, 96%, 97%, 98%, 99% or more sequence identity to the given recognition sequence, wherein the active variants retain biological activity and hence are capable of being recognized and cleaved by a nuclease agent in a sequence-specific manner. Assays to measure the double-strand break of a recognition sequence by a nuclease agent are known in the art (e.g., TAQMAN® qPCR assay, Frendewey et al. (2010) *Methods in Enzymology* 476:295-307, herein incorporated by reference in its entirety for all purposes).

The length of the recognition sequence can vary, and includes, for example, recognition sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

The recognition sequence of the nuclease agent can be positioned anywhere in or near the target genomic locus. The recognition sequence can be located within a coding region of a gene (e.g., the Fbn1 gene), or within regulatory regions that influence the expression of the gene. A recognition sequence of the nuclease agent can be located in an intron, an exon, a promoter, an enhancer, a regulatory region, or any non-protein coding region.

One type of nuclease agent that can be employed in the various methods and compositions disclosed herein is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease such as FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *Proc. Natl. Acad. Sci. U.S.A.* 107(50:21617-21622; Scholze & Boch (2010) *Virulence* 1:428-432; Christian et al. (2010) *Genetics* 186:757-761; Li et al. (2011) *Nucleic Acids Res.* 39(1):359-372; and Miller et al. (2011) *Nature Biotechnology* 29:143-148, each of which is herein incorporated by reference in its entirety for all purposes.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety for all purposes. In various embodiments, TAL effector nucleases are engineered that cut in or near a target nucleic acid sequence in, for example, a genomic locus of interest, wherein the target nucleic acid sequence is at or near a sequence to be modified by a an exogenous repair template. The TAL nucleases suitable for use with the various methods and compositions provided herein include those that are specifically designed to bind at or near target nucleic acid sequences to be modified by exogenous repair templates as described elsewhere herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

Another example of a nuclease agent that can be employed in the various methods and compositions disclosed herein is a zinc-finger nuclease (ZFN). In some ZFNs, each monomer of the ZFN comprises three or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US 2006/0246567; US 2008/0182332; US 2002/0081614; US 2003/0021776; WO 2002/057308 A2; US 2013/0123484; US 2010/0291048; WO 2011/017293 A2; and Gaj et al. (2013) *Trends in Biotechnology* 31(7):397-405, each of which is herein incorporated by reference in its entirety for all purposes.

Another type of nuclease agent that can be employed in the various methods and compositions disclosed herein is a meganuclease. Meganucleases have been classified into four families based on conserved sequence motifs: the LAGLIDADG, GIY-YIG, H-N-H, and His-Cys box families. These motifs participate in the coordination of metal ions and hydrolysis of phosphodiester bonds. Meganucleases are notable for their long recognition sequences and for tolerating some sequence polymorphisms in their DNA substrates. Meganuclease domains, structure, and function are known. See, e.g., Guhan and Muniyappa (2003) *Crit Rev Biochem Mol Biol.* 38:199-248; Lucas et al. (2001) *Nucleic Acids Res.* 29:960-969; Jurica and Stoddard, (1999) *Cell Mol Life Sci* 55:1304-1326; Stoddard (2006) *Q Rev Biophys* 38:49-95; and Moure et al. (2002) *Nat Struct Biol* 9:764. In some examples, a naturally occurring variant and/or engineered derivative meganuclease is used. Methods for modifying the kinetics, cofactor interactions, expression, optimal conditions, and/or recognition sequence specificity are known, and methods for screening for activity are known. See, e.g., Epinat et al., (2003) *Nucleic Acids Res.* 31:2952-2962; Chevalier et al. (2002) *Mol. Cell* 10:895-905; Gimble et al. (2003) *Mol. Biol.* 334:993-1008; Seligman et al. (2002) *Nucleic Acids Res.* 30:3870-3879; Sussman et al. (2004) *J. Mol. Biol.* 342:31-41; Rosen et al. (2006) *Nucleic Acids Res.* 34:4791-4800; Chames et al. (2005) *Nucleic Acids Res.* 33:e178; Smith et al. (2006) *Nucleic Acids Res.* 34:e149; Gruen et al. (2002) *Nucleic Acids Res.* 30:e29; Chen and Zhao (2005) *Nucleic Acids Res* 33:e154; WO 2005/105989; WO 2003/078619; WO 2006/097854; WO 2006/097853; WO 2006/097784; and WO 2004/031346, each of which is herein incorporated by reference in its entirety for all purposes.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, a meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Suitable nuclease agents also include restriction endonucleases, which include Type I, Type II, Type III, and Type IV endonucleases. Type I and Type III restriction endonucleases recognize specific recognition sequences but typically cleave at a variable position from the nuclease binding site, which can be hundreds of base pairs away from the cleavage site (recognition sequence). In Type II systems, the restriction activity is independent of any methylase activity, and cleavage typically occurs at specific sites within or near to the binding site. Most Type II enzymes cut palindromic sequences. However, Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example, in the REBASE database (webpage at rebase.neb.com; Roberts et al. (2003) *Nucleic Acids Res.* 31:418-420; Roberts et al. (2003) *Nucleic Acids Res.* 31:1805-1812; and Belfort et al. (2002) in *Mobile DNA II*, pp. 761-783, Eds. Craigie et al., (ASM Press, Washington, D.C.), each of which is herein incorporated by reference in its entirety for all purposes.

Other suitable nuclease agents for use in the methods and compositions described herein include CRISPR-Cas systems, which are described elsewhere herein.

The nuclease agent may be introduced into the cell by any means known in the art. A polypeptide encoding the nuclease agent may be directly introduced into the cell. Alternatively, a polynucleotide encoding the nuclease agent can be introduced into the cell. When a polynucleotide encoding the nuclease agent is introduced into the cell, the nuclease agent can be transiently, conditionally, or constitutively expressed within the cell. For example, the polynucleotide encoding the nuclease agent can be contained in an expression cassette and be operably linked to a conditional promoter, an inducible promoter, a constitutive promoter, or a tissue-specific promoter. Such promoters are discussed in further detail elsewhere herein. Alternatively, the nuclease agent can be introduced into the cell as an mRNA encoding a nuclease agent.

A polynucleotide encoding a nuclease agent can be stably integrated in the genome of the cell and operably linked to a promoter active in the cell. Alternatively, a polynucleotide encoding a nuclease agent can be in a targeting vector or in a vector or a plasmid that is separate from the targeting vector comprising the insert polynucleotide.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given prokaryotic or eukaryotic cell of interest, including a bacterial cell, a yeast cell, a human cell, a non-human cell, a mammalian cell, a rodent cell, a mouse cell, a rat cell or any other host cell of interest, as compared to the naturally occurring polynucleotide sequence.

C. CRISPR-Cas Systems

The methods disclosed herein can utilize Clustered Regularly Interspersed Short Palindromic Repeats (CRISPR)/CRISPR-associated (Cas) systems or components of such systems to modify a genome within a cell. CRISPR-Cas systems include transcripts and other elements involved in the expression of, or directing the activity of, Cas genes. A CRISPR-Cas system can be a type I, a type II, or a type III system. Alternatively a CRISPR/Cas system can be, for example, a type V system (e.g., subtype V-A or subtype V-B). The methods and compositions disclosed herein can employ CRISPR-Cas systems by utilizing CRISPR complexes (comprising a guide RNA (gRNA) complexed with a Cas protein) for site-directed cleavage of nucleic acids.

The CRISPR-Cas systems used in the methods disclosed herein are non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, some CRISPR-Cas systems employ non-naturally occurring CRISPR complexes comprising a gRNA and a Cas protein that do not naturally occur together.

(1) Cas Proteins

Cas proteins generally comprise at least one RNA recognition or binding domain that can interact with guide RNAs (gRNAs, described in more detail below). Cas proteins can also comprise nuclease domains (e.g., DNase or RNase domains), DNA binding domains, helicase domains, protein interaction domains, dimerization domains, and other domains. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break in the Fbn1 gene (e.g., a double-strand break with blunt ends), or it can be a nickase that creates a single-strand break in the Fbn1 gene.

Examples of Cas proteins include Cas1, Cas1B, Cas2, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

Preferably, the Cas protein is a Cas9 protein or is derived from a Cas9 protein from a type II CRISPR-Cas system. Cas9 proteins are from a type II CRISPR-Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* Additional examples of the Cas9 family members are described in WO 2014/131833, herein incorporated by reference in its entirety for all purposes. Cas9 from *S. pyogenes* (assigned SwissProt accession number Q99ZW2) is a preferred enzyme. Cas9 from *S. aureus* (assigned UniProt accession number J7RUA5) is another preferred enzyme.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida*, *Prevotella albensis*, *Lachnospiraceae bacterium* MC2017 1, *Butyrivibrio proteoclasticus*, *Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum*, *Eubacterium eligens*, *Moraxella bovoculi* 237, *Leptospira inadai*, *Lachnospiraceae bacterium* ND2006, *Porphyromonas crevioricanis* 3, *Prevotella disiens*, and *Porphyromonas macacae*. Cpf1 from *Francisella novicida* U112 (FnCpf1; assigned UniProt accession number A0Q7Q2) is a preferred enzyme.

Cas proteins can be wild type proteins (i.e., those that occur in nature), modified Cas proteins (i.e., Cas protein variants), or fragments of wild type or modified Cas proteins. Cas proteins can also be active variants or fragments of wild type or modified Cas proteins. Active variants or fragments can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity of the Cas protein.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or both of the nuclease domains can be deleted or mutated so that they are no longer functional or have reduced nuclease activity. If one of the nuclease domains is deleted or mutated, the resulting Cas protein (e.g., Cas9) can be referred to as a nickase and can generate a single-strand break at a guide RNA recognition sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null Cas protein). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839) or H840A (histidine to alanine at amino acid position 840) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes.

Cas proteins can also be operably linked to heterologous polypeptides as fusion proteins. For example, a Cas protein can be fused to a cleavage domain, an epigenetic modification domain, a transcriptional activation domain, or a transcriptional repressor domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

An example of a Cas fusion protein is a Cas protein fused to a heterologous polypeptide that provides for subcellular localization. Such heterologous polypeptides can include, for example, one or more nuclear localization signals (NLS) such as the SV40 NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence.

Cas proteins can also be operably linked to a cell-penetrating domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290, herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g. eBFP, eBFP2, Azurite, mKalama1, GFPuv, Sapphire, T-sapphire), cyan fluorescent proteins (e.g. eCFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly (NANP), tandem affinity purification (TAP) tag, myc, AcV5, AU1, AU5, E, ECS, E2, FLAG, hemagglutinin (HA), nus, Softag 1, Softag 3, Strep, SBP, Glu-Glu, HSV, KT3, S, 51, T7, V5, VSV-G, histidine (His), biotin carboxyl carrier protein (BCCP), and calmodulin.

Cas9 proteins can also be tethered to exogenous repair templates or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous repair template or labeled nucleic acid can be tethered to the C-terminus, the N-terminus, or to an internal region within the Cas9 protein. Preferably, the exogenous repair template or labeled nucleic acid is tethered to the C-terminus or the N-terminus of the Cas9 protein. Likewise, the Cas9 protein can be tethered to the 5' end, the 3' end, or to an internal region within the exogenous repair template or labeled nucleic acid. That is, the exogenous repair template or labeled nucleic acid can be tethered in any orientation and polarity. Preferably, the Cas9 protein is tethered to the 5' end or the 3' end of the exogenous repair template or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

(2) Guide RNAs

A "guide RNA" or "gRNA" is an RNA molecule that binds to a Cas protein (e.g., Cas9 protein) and targets the Cas protein to a specific location within a target DNA (e.g., the Fbn1 gene). Guide RNAs can comprise two segments: a "DNA-targeting segment" and a "protein-binding segment." "Segment" includes a section or region of a molecule, such as a contiguous stretch of nucleotides in an RNA. Some gRNAs comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve cleavage. The terms "guide RNA" and "gRNA" include both double-molecule gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA" or "scaffold") molecule. A crRNA comprises both the DNA-targeting segment (single-stranded) of the gRNA and a stretch of nucleotides that forms one half of the dsRNA duplex of the protein-binding segment of the gRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA.

The crRNA and the corresponding tracrRNA hybridize to form a gRNA. In systems in which only a crRNA is needed, the crRNA can be the gRNA. The crRNA additionally provides the single-stranded DNA-targeting segment that hybridizes to a guide RNA recognition sequence. If used for modification within a cell, the exact sequence of a given crRNA or tracrRNA molecule can be designed to be specific to the species in which the RNA molecules will be used. See, e.g., Mali et al. (2013) *Science* 339:823-826; Jinek et al. (2012) *Science* 337:816-821; Hwang et al. (2013) *Nat. Biotechnol.* 31:227-229; Jiang et al. (2013) *Nat. Biotechnol.* 31:233-239; and Cong et al. (2013) *Science* 339:819-823, each of which is herein incorporated by reference in its entirety for all purposes.

The DNA-targeting segment (crRNA) of a given gRNA comprises a nucleotide sequence that is complementary to a sequence (i.e., the guide RNA recognition sequence) in a target DNA. The DNA-targeting segment of a gRNA interacts with a target DNA (e.g., the Fbn1 gene) in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR-Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of *S. pyogenes*, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from *S. pyogenes*, a typical DNA-targeting segment is between 16 and 20 nucleotides in length or between 17 and 20 nucleotides in length. For Cas9 from *S. aureus*, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrR-NAs or active partial tracrRNAs) and of varying lengths. They can include primary transcripts or processed forms. For example, tracrRNAs (as part of a single-guide RNA or as a separate molecule as part of a two-molecule gRNA) may comprise or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from *S. pyogenes* include 171-nucleotide, 89-nucleotide, 75-nucleotide, and 65-nucleotide versions. See, e.g., Deltcheva et al. (2011) *Nature* 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting sequence and the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting sequence and the guide RNA recognition sequence within the target DNA can be at least 60% over about 20 contiguous nucleotides. As an example, the percent complementarity between the DNA-targeting sequence and the guide RNA recognition sequence within the target DNA is 100% over the 14 contiguous nucleotides at the 5' end of the guide RNA recognition sequence within the complementary strand of the target DNA and as low as 0% over the remainder. In such a case, the DNA-targeting sequence can be considered to be 14 nucleotides in length. As another example, the percent complementarity between the DNA-targeting sequence and the guide RNA recognition sequence within the target DNA is 100% over the seven contiguous nucleotides at the 5' end of the guide RNA recognition sequence within the complementary strand of the target DNA and as low as 0% over the remainder. In such a case, the DNA-targeting sequence can be considered to be 7 nucleotides in length. In some guide RNAs, at least 17 nucleotides within the DNA-target sequence are complementary to the target DNA. For example, the DNA-targeting sequence can be 20 nucleotides in length and can comprise 1, 2, or 3 mismatches with the target DNA (the guide RNA recognition sequence). Preferably, the mismatches are not adjacent to a protospacer adjacent motif (PAM) sequence (e.g., the mismatches are in the 5' end of the DNA-targeting sequence, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including transcriptional activators, transcriptional repressors, DNA methyltransferases, DNA demethylases, histone acetyltransferases, histone deacetylases, and the like); and combinations thereof.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be prepared by chemical synthesis.

The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising an exogenous repair template and/or a vector comprising a nucleic acid encoding a Cas protein. Alternatively, it can be in a vector or a plasmid that is separate from the vector comprising an exogenous repair template and/or the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

(3) Guide RNA Recognition Sequences

The term "guide RNA recognition sequence" includes nucleic acid sequences present in a target DNA (e.g., the Fbn1 gene) to which a DNA-targeting segment of a gRNA will bind, provided sufficient conditions for binding exist. For example, guide RNA recognition sequences include sequences to which a guide RNA is designed to have complementarity, where hybridization between a guide RNA recognition sequence and a DNA targeting sequence promotes the formation of a CRISPR complex. Full complementarity is not necessarily required, provided that there is sufficient complementarity to cause hybridization and promote formation of a CRISPR complex. Guide RNA recognition sequences also include cleavage sites for Cas proteins, described in more detail below. A guide RNA recognition sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known in the art (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "noncomplementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence." The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence of the nickase on the first strand is separated from the guide RNA recognition sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA recognition sequence. Optionally, the guide RNA recognition sequence can be flanked on the 3' end by the PAM. Alternatively, the guide RNA recognition sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA. As such, the PAM sequence of the complementary strand would be 5'-CC$N_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT (SEQ ID NO: 146) or NNGRR (SEQ ID NO: 147), where N can A, G, C, or T, and R can be G or A. In some cases (e.g., for FnCpf1), the PAM sequence can be upstream of the 5' end and have the sequence 5'-TTN-3'.

Examples of guide RNA recognition sequences include a DNA sequence complementary to the DNA-targeting segment of a gRNA, or such a DNA sequence in addition to a PAM sequence. For example, the target motif can be a 20-nucleotide DNA sequence immediately preceding an NGG motif recognized by a Cas9 protein, such as G$N_{19}$NGG (SEQ ID NO: 39) or $N_{20}$NGG (SEQ ID NO: 40) (see, e.g., WO 2014/165825, herein incorporated by reference in its entirety for all purposes). The guanine at the 5' end can facilitate transcription by RNA polymerase in cells. Other examples of guide RNA recognition sequences can include two guanine nucleotides at the 5' end (e.g., GG$N_{20}$NGG; SEQ ID NO: 41) to facilitate efficient transcription by T7 polymerase in vitro. See, e.g., WO 2014/065596, herein incorporated by reference in its entirety for all purposes. Other guide RNA recognition sequences can have between 4-22 nucleotides in length of SEQ ID NOS: 39-41, including the 5' G or GG and the 3' GG or NGG. Yet other guide RNA recognition sequences can have between 14 and 20 nucleotides in length of SEQ ID NOS: 39-41.

The guide RNA recognition sequence can be any nucleic acid sequence endogenous or exogenous to a cell. The guide RNA recognition sequence can be a sequence coding a gene product (e.g., a protein) or a non-coding sequence (e.g., a regulatory sequence) or can include both.

D. Exogenous Repair Templates

The methods and compositions disclosed herein can utilize exogenous repair templates to modify an Fbn1 gene following cleavage of the Fbn1 gene with a nuclease agent. For example, the cell can be a one-cell stage embryo, and the exogenous repair template can be less 5 kb in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein (e.g., a targeting vector having a length of at least 10 kb or having 5' and 3' homology arms having a sum total of at least 10 kb). Using exogenous repair templates in combination with nuclease agents may result in more precise modifications within the Fbn1 gene by promoting homology-directed repair.

In such methods, the nuclease agent cleaves the Fbn1 gene to create a single-strand break (nick) or double-strand break, and the exogenous repair template recombines the Fbn1 gene via non-homologous end joining (NHEJ)-mediated ligation or through a homology-directed repair event. Optionally, repair with the exogenous repair template removes or disrupts the nuclease cleavage site so that alleles that have been targeted cannot be re-targeted by the nuclease agent.

Exogenous repair templates can comprise deoxyribonucleic acid (DNA) or ribonucleic acid (RNA), they can be single-stranded or double-stranded, and they can be in linear or circular form. For example, an exogenous repair template can be a single-stranded oligodeoxynucleotide (ssODN). See, e.g., Yoshimi et al. (2016) *Nat. Commun.* 7:10431, herein incorporated by reference in its entirety for all purposes. An exemplary exogenous repair template is between about 50 nucleotides to about 5 kb in length, is between about 50 nucleotides to about 3 kb in length, or is between about 50 to about 1,000 nucleotides in length. Other exemplary exogenous repair templates are between about 40 to about 200 nucleotides in length. For example, an exogenous repair template can be between about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Alternatively, an exogenous repair template can be between about 50 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Alternatively, an exogenous repair template can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. Alternatively, an exogenous repair template can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. In cell types other than one-cell stage embryos, the exogenous repair template (e.g., targeting vector) can be longer. For example, in cell types other than one-cell stage embryos, the exogenous repair template can be a large targeting vector (LTVEC) as described elsewhere herein.

In one example, an exogenous repair template is an ssODN that is between about 80 nucleotides and about 200 nucleotides in length. In another example, an exogenous repair templates is an ssODN that is between about 80 nucleotides and about 3 kb in length. Such an ssODN can have homology arms, for example, that are each between about 40 nucleotides and about 60 nucleotides in length. Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous repair templates can include modifications or sequences that provide for additional desirable features (e.g., modified or regulated stability; tracking or detecting with a fluorescent label; a binding site for a protein or protein complex; and so forth). Exogenous repair templates can comprise one or more fluorescent labels, purification tags, epitope tags, or a combination thereof. For example, an exogenous repair template can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous repair template that has been directly integrated into a cleaved Fbn1 gene having protruding ends compatible with the ends of the exogenous repair template. The label or tag can be at the 5' end, the 3' end, or internally within the exogenous repair template. For example, an exogenous repair template can be conjugated at 5' end with the IR700 fluorophore from Integrated DNA Technologies (5'IRDYE® 700).

Exogenous repair templates can also comprise nucleic acid inserts including segments of DNA to be integrated in the Fbn1 gene. Integration of a nucleic acid insert in the Fbn1 gene can result in addition of a nucleic acid sequence of interest in the Fbn1 gene, deletion of a nucleic acid sequence of interest in the Fbn1 gene, or replacement of a nucleic acid sequence of interest in the Fbn1 gene (i.e., deletion and insertion). Some exogenous repair templates are designed for insertion of a nucleic acid insert in the Fbn1 gene without any corresponding deletion in the Fbn1 gene. Other exogenous repair templates are designed to delete a nucleic acid sequence of interest in the Fbn1 gene without any corresponding insertion of a nucleic acid insert. Yet other exogenous repair templates are designed to delete a nucleic acid sequence of interest in the Fbn1 gene and replace it with a nucleic acid insert.

The nucleic acid insert or the corresponding nucleic acid in the Fbn1 gene being deleted and/or replaced can be various lengths. An exemplary nucleic acid insert or corresponding nucleic acid in the Fbn1 gene being deleted and/or replaced is between about 1 nucleotide to about 5 kb in length or is between about 1 nucleotide to about 1,000 nucleotides in length. For example, a nucleic acid insert or a corresponding nucleic acid in the Fbn1 gene being deleted and/or replaced can be between about 1 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150, about 150 to about 160, about 160 to about 170, about 170 to about 180, about 180 to about 190, or about 190 to about 200 nucleotides in length. Likewise, a nucleic acid insert or a corresponding nucleic acid in the Fbn1 gene being deleted and/or replaced can be between about 1 to about 100, about 100 to about 200, about 200 to about 300, about 300 to about 400, about 400 to about 500, about 500 to about 600, about 600 to about 700, about 700 to about 800, about 800 to about 900, or about 900 to about 1,000 nucleotides in length. Likewise, a nucleic acid insert or a corresponding nucleic acid in the Fbn1 gene being deleted and/or replaced can be between about 1 kb to about 1.5 kb, about 1.5 kb to about 2 kb, about 2 kb to about 2.5 kb, about 2.5 kb to about 3 kb, about 3 kb to about 3.5 kb, about 3.5 kb to about 4 kb, about 4 kb to about 4.5 kb, or about 4.5 kb to about 5 kb in length. A nucleic acid being deleted from the Fbn1 gene can also be between about 1 kb to about 5 kb, about 5 kb to about 10 kb, about 10 kb to about 20 kb, about 20 kb to about 30 kb, about 30 kb to about 40 kb, about 40 kb to about 50 kb, about 50 kb to about 60 kb, about 60 kb to about 70 kb, about 70 kb to about 80 kb, about 80 kb to about 90 kb, about 90 kb to about 100 kb, about 100 kb to about 200 kb, about 200 kb to about 300 kb, about 300 kb to about 400 kb, about 400 kb to about 500 kb, about 500 kb to about 600 kb, about 600 kb to about 700 kb, about 700 kb to about 800 kb, about 800 kb to about 900 kb, about 900 kb to about 1 Mb or longer. Alternatively, a nucleic acid being deleted from the Fbn1 gene can be between about 1 Mb to about 1.5 Mb, about 1.5 Mb to about 2 Mb, about 2 Mb to about 2.5 Mb, about 2.5 Mb to about 3 Mb, about 3 Mb to about 4 Mb, about 4 Mb to about 5 Mb, about 5 Mb to about 10 Mb, about 10 Mb to about 20 Mb, about 20 Mb to about 30 Mb, about 30 Mb to about 40 Mb, about 40 Mb to about 50 Mb, about 50 Mb to about 60 Mb, about 60 Mb to about 70 Mb, about 70 Mb to about 80 Mb, about 80 Mb to about 90 Mb, or about 90 Mb to about 100 Mb.

The nucleic acid insert can comprise genomic DNA or any other type of DNA. For example, the nucleic acid insert can be from a prokaryote, a eukaryote, a yeast, a bird (e.g., chicken), a non-human mammal, a rodent, a human, a rat, a mouse, a hamster, a rabbit, a pig, a bovine, a deer, a sheep, a goat, a cat, a dog, a ferret, a primate (e.g., marmoset, rhesus monkey), a domesticated mammal, an agricultural mammal, a turtle, or any other organism of interest.

The nucleic acid insert can comprise a sequence that is homologous or orthologous to all or part of the Fbn1 gene (e.g., a portion of the gene encoding a particular motif or region of the Fibrillin-1 protein). The homologous sequence can be from a different species or the same species. For example, the nucleic acid insert can comprise a sequence that comprises one or more point mutations (e.g., 1, 2, 3, 4, 5, or more) compared with a sequence targeted for replacement in the Fbn1 gene. In some cases, the nucleic acid insert is a human Fbn1 sequence. This can result in humanization of all or part of the Fbn1 locus in the non-human animal if insertion of the nucleic acid insert results in replacement of all or part of the Fbn1 non-human nucleic acid sequence with the corresponding orthologous human nucleic acid sequence (i.e., the nucleic acid insert is inserted in place of the corresponding non-human DNA sequence at its endogenous genomic locus). The inserted human sequence can further comprise one or more mutations in the human Fbn1 gene.

The nucleic acid insert or the corresponding nucleic acid in the Fbn1 gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

The nucleic acid insert can also comprise a conditional allele. The conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

Nucleic acid inserts can also comprise a polynucleotide encoding a selection marker. Alternatively, the nucleic acid inserts can lack a polynucleotide encoding a selection marker. The selection marker can be contained in a selection cassette. Optionally, the selection cassette can be a self-deleting cassette. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. Exemplary selection markers include neomycin phosphotransferase (neo$^r$), hygromycin B phosphotransferase (hyg$^r$), puromycin-N-acetyltransferase (puro$_r$), blasticidin S deaminase (bsr$^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A given cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein.

The nucleic acid insert can comprise a nucleic acid flanked with site-specific recombination target sequences. Alternatively, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In one example, the site-specific recombination sites flank a polynucleotide encoding a selection marker and/or a reporter gene contained within the nucleic acid insert. Following integration of the nucleic acid insert in the Fbn1 gene, the sequences between the site-specific recombination sites can be removed. Optionally, two exogenous repair templates can be used, each with a nucleic acid insert comprising a site-specific recombination site. The exogenous repair templates can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example in the REBASE database (webpage at rebase.neb.com; Roberts et al., (2003) *Nucleic Acids Res.* 31:418-420; Roberts et al., (2003) *Nucleic Acids Res.* 31:1805-1812; and Belfort et al. (2002) in *Mobile DNA II*, pp. 761-783, Eds. Craigie et al., (ASM Press, Washington, D.C.)).

(1) Repair Templates for Non-Homologous-End-Joining-Mediated Insertion

Some exogenous repair templates have short single-stranded regions at the 5' end and/or the 3' end that are complementary to one or more overhangs created by Cas-protein-mediated cleavage at the target genomic locus (e.g., in the Fbn1 gene). These overhangs can also be referred to as 5' and 3' homology arms. For example, some exogenous repair templates have short single-stranded regions at the 5' end and/or the 3' end that are complementary to one or more overhangs created by Cas-protein-mediated cleavage at 5' and/or 3' target sequences at the target genomic locus. Some such exogenous repair templates have a complementary region only at the 5' end or only at the 3' end. For example, some such exogenous repair templates have a complementary region only at the 5' end complementary to an overhang created at a 5' target sequence at the target genomic locus or only at the 3' end complementary to an overhang created at a 3' target sequence at the target genomic locus. Other such exogenous repair templates have complementary regions at both the 5' and 3' ends. For example, other such exogenous repair templates have complementary regions at both the 5' and 3' ends e.g., complementary to first and second overhangs, respectively, generated by Cas-mediated cleavage at the target genomic locus. For example, if the exogenous repair template is double-stranded, the single-stranded complementary regions can extend from the 5' end of the top strand of the repair template and the 5' end of the bottom strand of the repair template, creating 5' overhangs on each end. Alternatively, the single-stranded complementary region can extend from the 3' end of the top strand of the repair template and from the 3' end of the bottom strand of the template, creating 3' overhangs.

The complementary regions can be of any length sufficient to promote ligation between the exogenous repair template and the Fbn1 gene. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5 to about 10, about 10 to about 20, about 20 to about 30, about 30 to about 40, about 40 to about 50, about 50 to about 60, about 60 to about 70, about 70 to about 80, about 80 to about 90, about 90 to about 100, about 100 to about 110, about 110 to about 120, about 120 to about 130, about 130 to about 140, about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). Preferably, the nicks within the first and second guide RNA recognition sequences and/or the third and fourth guide RNA recognition sequences can be offset nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous repair template can be designed with single-stranded complementary regions that are complementary to the overhangs created by the nicks within the first and second guide RNA recognition sequences and by the nicks within the third and fourth guide RNA recognition sequences. Such an exogenous repair template can then be inserted by non-homologous-end-joining-mediated ligation.

(2) Repair Templates for Insertion by Homology-Directed Repair

Some exogenous repair templates comprise homology arms. If the exogenous repair template also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous repair template. The 5' and 3' homology arms correspond to regions within the Fbn1 gene, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous repair template can be any degree of sequence identity that allows for homologous recombination to occur. For example, the amount of sequence identity shared by the homology arm of the exogenous repair template (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25 to about 30, about 30 to about 40, about 40 to about 50, about 50 to about 60, about 60 to about 70, about 70 to about 80, about 80 to about 90, about 90 to about 100, about 100 to about 150, about 150 to about 200, about 200 to about 250, about 250 to about 300, about 300 to about 350, about 350 to about 400, about 400 to about 450, or about 450 to about 500 nucleotides in length, such that the homology arms have sufficient homology to undergo homologous recombination with the corresponding target sequences within the Fbn1 gene. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternatively, for example, they can correspond to a region of a heterologous or exogenous segment of DNA that was integrated into the genome of the cell, including, for example, transgenes, expression cassettes, or heterologous or exogenous regions of DNA. Alternatively, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

When a nuclease agent is used in combination with an exogenous repair template, the 5' and 3' target sequences are preferably located in sufficient proximity to the nuclease cleavage site so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the Fbn1 gene that correspond to the 5' and 3' homology arms of the exogenous repair template are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous repair template can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous repair template and the nuclease cleavage site can vary. For example, target sequences can be located 5' to the nuclease cleavage site, target sequences can be located 3' to the nuclease cleavage site, or the target sequences can flank the nuclease cleavage site.

In cells other than one-cell stage embryos, the exogenous repair template can be a "large targeting vector" or "LTVEC," which includes targeting vectors that comprise homology arms that correspond to and are derived from nucleic acid sequences larger than those typically used by other approaches intended to perform homologous recombination in cells. LTVECs also include targeting vectors comprising nucleic acid inserts having nucleic acid sequences larger than those typically used by other approaches intended to perform homologous recombination in cells. For example, LTVECs make possible the modification of large loci that cannot be accommodated by traditional plasmid-based targeting vectors because of their size limitations. For example, the targeted locus can be (i.e., the 5' and 3' homology arms can correspond to) a locus of the cell that is not targetable using a conventional method or that can be targeted only incorrectly or only with significantly low efficiency in the absence of a nick or double-strand break induced by a nuclease agent (e.g., a Cas protein).

Examples of LTVECs include vectors derived from a bacterial artificial chromosome (BAC), a human artificial chromosome, or a yeast artificial chromosome (YAC). Non-limiting examples of LTVECs and methods for making them are described, e.g., in U.S. Pat. Nos. 6,586,251; 6,596,541; and 7,105,348; and in WO 2002/036789, each of which is herein incorporated by reference in its entirety for all purposes. LTVECs can be in linear form or in circular form.

LTVECs can be of any length and are typically at least 10 kb in length. For example, an LTVEC can be from about 50 kb to about 300 kb, from about 50 kb to about 75 kb, from about 75 kb to about 100 kb, from about 100 kb to 125 kb, from about 125 kb to about 150 kb, from about 150 kb to about 175 kb, about 175 kb to about 200 kb, from about 200 kb to about 225 kb, from about 225 kb to about 250 kb, from about 250 kb to about 275 kb or from about 275 kb to about 300 kb. Alternatively, an LTVEC can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 150 kb, at least 200 kb, at least 250 kb, at least 300 kb, at least 350 kb, at least 400 kb, at least 450 kb, or at least 500 kb or greater. The size of an LTVEC can be too large to enable screening of targeting events by conventional assays, e.g., southern blotting and long-range (e.g., 1 kb to 5 kb) PCR The sum total of the 5' homology arm and the 3' homology arm in an LTVEC is typically at least 10 kb. As an example, the 5' homology arm can range from about 5 kb to about 100 kb and/or the 3' homology arm can range from about 5 kb to about 100 kb. Each homology arm can be, for example, from about 5 kb to about 10 kb, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. The sum total of the 5' and 3' homology arms can be, for example, from about 10 kb to about 20 kb, from about 20 kb to about 30 kb, from about 30 kb to about 40 kb, from about 40 kb to about 50 kb, from about 50 kb to about 60 kb, from about 60 kb to about 70 kb, from about 70 kb to about 80 kb, from about 80 kb to about 90 kb, from about 90 kb to about 100 kb, from about 100 kb to about 110 kb, from about 110 kb to about 120 kb, from about 120 kb to about 130 kb, from about 130 kb to about 140 kb, from about 140 kb to about 150 kb, from about 150 kb to about 160 kb, from about 160 kb to about 170 kb, from about 170 kb to about 180 kb, from about 180 kb to about 190 kb, or from about 190 kb to about 200 kb. Alternatively, each homology arm can be at least 5 kb, at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb. Likewise, the sum total of the 5' and 3' homology arms can be at least 10 kb, at least 15 kb, at least 20 kb, at least 30 kb, at least 40 kb, at least 50 kb, at least 60 kb, at least 70 kb, at least 80 kb, at least 90 kb, at least 100 kb, at least 110 kb, at least 120 kb, at least 130 kb, at least 140 kb, at least 150 kb, at least 160 kb, at least 170 kb, at least 180 kb, at least 190 kb, or at least 200 kb.

LTVECs can comprise nucleic acid inserts having nucleic acid sequences larger than those typically used by other approaches intended to perform homologous recombination in cells. For example, an LTVEC can comprise a nucleic acid insert ranging from about 5 kb to about 10 kb, from about 10 kb to about 20 kb, from about 20 kb to about 40 kb, from about 40 kb to about 60 kb, from about 60 kb to about 80 kb, from about 80 kb to about 100 kb, from about 100 kb to about 150 kb, from about 150 kb to about 200 kb, from about 200 kb to about 250 kb, from about 250 kb to about 300 kb, from about 300 kb to about 350 kb, from about 350 kb to about 400 kb, or greater.

E. Contacting the Genome of a Cell and Introducing Nucleic Acids into Cells

Contacting the genome of a cell can comprise introducing one or more nuclease agents or nucleic acids encoding nuclease agents (e.g., one or more Cas proteins or nucleic acids encoding one or more Cas proteins, and one or more guide RNAs or nucleic acids encoding one or more guide RNAs (i.e., one or more CRISPR RNAs and one or more tracrRNAs)) and/or one or more exogenous repair templates into the cell, provided that if the cell is a one-cell stage embryo, for example, the exogenous repair template can be less than 5 kb in length. Contacting the genome of cell (i.e., contacting a cell) can comprise introducing only one of the above components, one or more of the components, or all of the components into the cell. "Introducing" includes presenting to the cell the nucleic acid or protein in such a manner that the sequence gains access to the interior of the cell. The introducing can be accomplished by any means, and one or more of the components (e.g., two of the components, or all of the components) can be introduced into the cell simultaneously or sequentially in any combination. For example, an exogenous repair template can be introduced prior to the introduction of a nuclease agent, or it can be introduced following introduction of nuclease agent (e.g., the exogenous repair template can be administered about 1, 2, 3, 4, 8, 12, 24, 36, 48, or 72 hours before or after introduction of the nuclease agent). See, e.g., US 2015/0240263 and US 2015/0110762, each of which is herein incorporated by reference in its entirety for all purposes.

A nuclease agent can be introduced into the cell in the form of a protein or in the form of a nucleic acid encoding the nuclease agent, such as an RNA (e.g., messenger RNA (mRNA)) or DNA. When introduced in the form of a DNA, the DNA can be operably linked to a promoter active in the cell. Such DNAs can be in one or more expression constructs.

For example, a Cas protein can be introduced into the cell in the form of a protein, such as a Cas protein complexed with a gRNA, or in the form of a nucleic acid encoding the Cas protein, such as an RNA (e.g., messenger RNA (mRNA)) or DNA. A guide RNA can be introduced into the cell in the form of an RNA or in the form of a DNA encoding the guide RNA. When introduced in the form of a DNA, the DNA encoding the Cas protein and/or the guide RNA can be operably linked to a promoter active in the cell. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs, DNAs encoding one or more tracrRNAs, and DNA encoding a Cas protein can be components of separate nucleic acid molecules).

In some methods, DNA encoding a nuclease agent (e.g., a Cas protein and a guide RNA) and/or DNA encoding an exogenous repair template can be introduced into a cell via DNA minicircles. See, e.g., WO 2014/182700, herein incorporated by reference in its entirety for all purposes. DNA minicircles are supercoiled DNA molecules that can be used for non-viral gene transfer that have neither an origin of replication nor an antibiotic selection marker. Thus, DNA minicircles are typically smaller in size than plasmid vector. These DNAs are devoid of bacterial DNA, and thus lack the unmethylated CpG motifs found in bacterial DNA.

The methods provided herein do not depend on a particular method for introducing a nucleic acid or protein into the cell, only that the nucleic acid or protein gains access to the interior of a least one cell. Methods for introducing nucleic acids and proteins into various cell types are known in the art and include, for example, stable transfection methods, transient transfection methods, and virus-mediated methods.

Transfection protocols as well as protocols for introducing nucleic acids or proteins into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEOFECTOR™ system.

Introduction of nucleic acids or proteins into a cell (e.g., a one-cell stage embryo) can also be accomplished by microinjection. In one-cell stage embryos, microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a protein or a DNA encoding a DNA encoding a Cas protein is preferably into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a nuclease agent protein is injected into the cytoplasm, the protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell can include, for example, vector delivery, particle-mediated delivery, exosome-mediated delivery, lipid-nanoparticle-mediated delivery, cell-penetrating-peptide-mediated delivery, or implantable-device-mediated delivery.

The introduction of nucleic acids or proteins into the cell can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

In some cases, the cells employed in the methods and compositions have a DNA construct stably incorporated into their genome. In such cases, the contacting can comprise providing a cell with the construct already stably incorporated into its genome. For example, a cell employed in the methods disclosed herein may have a preexisting Cas-encoding gene stably incorporated into its genome (i.e., a Cas-ready cell). "Stably incorporated" or "stably introduced" or "stably integrated" includes the introduction of a polynucleotide into the cell such that the nucleotide sequence integrates into the genome of the cell and is capable of being inherited by progeny thereof. Any protocol may be used for the stable incorporation of the DNA constructs or the various components of the targeted genomic integration system.

F. Types of Targeted Genetic Modifications

Various types of targeted genetic modifications can be introduced using the methods described herein. Such targeted modifications can include, for example, additions of one or more nucleotides, deletions of one or more nucleotides, substitutions of one or more nucleotides, a point mutation, a knockout of a polynucleotide of interest or a portion thereof, a knock-in of a polynucleotide of interest or a portion thereof, a replacement of an endogenous nucleic acid sequence with a heterologous, exogenous, homologous, or orthologous nucleic acid sequence, a domain swap, an exon swap, an intron swap, a regulatory sequence swap, a gene swap, or a combination thereof. For example, at least 1, 2, 3, 4, 5, 7, 8, 9, 10 or more nucleotides can be changed (e.g., deleted, inserted, or substituted) to form the targeted genomic modification. The deletions, insertions, or replacements can be of any size, as disclosed elsewhere herein. See, e.g., Wang et al. (2013) *Cell* 153:910-918; Mandalos et al. (2012) *PLOS ONE* 7:e45768:1-9; and Wang et al. (2013) *Nat Biotechnol.* 31:530-532, each of which is herein incorporated by reference in its entirety for all purposes.

Such targeted genetic modifications can result in disruption of a target genomic locus, can introduce disease-causing mutations or disease-causing alleles, can result in humanization of a target genomic locus (i.e., replacement of a non-human nucleic acid sequence with a homologous or an orthologous human nucleic acid sequence), can create conditional alleles, and so forth. Disruption can include alteration of a regulatory element (e.g., promoter or enhancer), a missense mutation, a nonsense mutation, a frame-shift mutation, a truncation mutation, a null mutation, or an insertion or deletion of small number of nucleotides (e.g., causing a frameshift mutation), and it can result in inactivation (i.e., loss of function) or loss of an allele.

The targeted genetic modification can be, for example, a biallelic modification or a monoallelic modification. Preferably, the targeted genetic modification is a monoallelic modification. Biallelic modifications include events in which the same modification is made to the same locus on corresponding homologous chromosomes (e.g., in a diploid cell), or in which different modifications are made to the same locus on corresponding homologous chromosomes. In some methods, the targeted genetic modification is a monoallelic modification. A monoallelic modification includes events in which a modification is made to only one allele (i.e., a modification to the Fbn1 gene in only one of the two homologous chromosomes). Homologous chromosomes include chromosomes that have the same genes at the same loci but possibly different alleles (e.g., chromosomes that are paired during meiosis). The term allele includes any of one or more alternative forms of a genetic sequence. In a diploid cell or organism, the two alleles of a given sequence typically occupy corresponding loci on a pair of homologous chromosomes.

A monoallelic mutation can result in a cell that is heterozygous for the targeted Fbn1 modification. Heterozygosity includes situation in which only one allele of the Fbn1 gene (i.e., corresponding alleles on both homologous chromosomes) have the targeted modification.

A biallelic modification can result in homozygosity for a targeted modification. Homozygosity includes situations in which both alleles of the Fbn1 gene (i.e., corresponding alleles on both homologous chromosomes) have the targeted modification. For example, the biallelic modification can be generated when a Cas protein cleaves a pair of first and second homologous chromosomes within a first guide RNA recognition sequence (i.e., at a first cleavage site within the first guide RNA recognition sequence), thereby generating end sequences in the first and second homologous chromosomes. The end sequences in each of the first and second homologous chromosomes can then undergo a repair process mediated by an exogenous repair template to form a genome with a biallelic modification comprising the targeted genetic modification. For example, if the exogenous repair template comprises a nucleic acid insert, the nucleic acid insert can be inserted in the Fbn1 gene in the pair of first and second homologous chromosomes, thereby resulting in a homozygous modified genome.

Alternatively, a biallelic modification can result in compound heterozygosity (e.g., hemizygosity) for the targeted modification. Compound heterozygosity includes situations in which both alleles of the target locus (i.e., the alleles on both homologous chromosomes) have been modified, but they have been modified in different ways (e.g., a targeted modification in one allele and inactivation or disruption of the other allele). For example, in the allele without the targeted modification, a double-strand break created by the Cas protein may have been repaired by non-homologous end joining (NHEJ)-mediated DNA repair, which generates a mutant allele comprising an insertion or a deletion of a nucleic acid sequence and thereby causes disruption of that genomic locus. For example, a biallelic modification can result in compound heterozygosity if the cell has one allele with the targeted modification and another allele that is not capable of being expressed. Compound heterozygosity includes hemizygosity. Hemizygosity includes situations in which only one allele (i.e., an allele on one of two homologous chromosomes) of the target locus is present. For example, a biallelic modification can result in hemizygosity for a targeted modification if the targeted modification occurs in one allele with a corresponding loss or deletion of the other allele.

G. Identifying Cells with Targeted Genetic Modifications

The methods disclosed herein can further comprise identifying a cell having a modified Fbn1 gene. Various methods can be used to identify cells having a targeted genetic modification, such as a deletion or an insertion. Such methods can comprise identifying one cell having the targeted genetic modification in the Fbn1 gene. Screening can be done to identify such cells with modified genomic loci.

The screening step can comprise a quantitative assay for assessing modification of allele (MOA) (e.g., loss-of-allele (LOA) and/or gain-of-allele (GOA) assays) of a parental chromosome. For example, the quantitative assay can be carried out via a quantitative PCR, such as a real-time PCR (qPCR). The real-time PCR can utilize a first primer set that recognizes the target genomic locus and a second primer set that recognizes a non-targeted reference locus. The primer set can comprise a fluorescent probe that recognizes the amplified sequence.

The screening step can also comprise a retention assay, which is an assay used to distinguish between correct targeted insertions of a nucleic acid insert into a target genomic locus from random transgenic insertions of the nucleic acid insert into genomic locations outside of the target genomic locus. Conventional assays for screening for targeted modifications, such as long-range PCR or Southern blotting, link the inserted targeting vector to the targeted locus. Because of their large homology arm sizes, however, LTVECs do not permit screening by such conventional assays. To screen LTVEC targeting, modification-of-allele (MOA) assays including loss-of-allele (LOA) and gain-of-allele (GOA) assays can be used (see, e.g., US 2014/0178879 and Frendewey et al. (2010) *Methods Enzymol.* 476:295-307, each of which is herein incorporated by reference in its entirety for all purposes). The loss-of-allele (LOA) assay inverts the conventional screening logic and quantifies the number of copies of the native locus to which the mutation was directed. In a correctly targeted cell clone, the LOA assay detects one of the two native alleles (for genes not on the X or Y chromosome), the other allele being disrupted by the targeted modification. The same principle can be applied in reverse as a gain-of-allele (GOA) assay to quantify the copy number of the inserted targeting vector. For example, the combined use of GOA and LOA assays will reveal a correctly targeted heterozygous clone as having lost one copy of the native target gene and gained one copy of the drug resistance gene or other inserted marker.

As an example, quantitative polymerase chain reaction (qPCR) can be used as the method of allele quantification, but any method that can reliably distinguish the difference between zero, one, and two copies of the target gene or between zero, one, and two copies of the nucleic acid insert can be used to develop a MOA assay. For example, TAQMAN® can be used to quantify the number of copies of a DNA template in a genomic DNA sample, especially by comparison to a reference gene (see, e.g., U.S. Pat. No. 6,596,541, herein incorporated by reference in its entirety for all purposes). The reference gene is quantitated in the same genomic DNA as the target gene(s) or locus(loci). Therefore, two TAQMAN® amplifications (each with its respective probe) are performed. One TAQMAN® probe determines the "Ct" (Threshold Cycle) of the reference gene, while the other probe determines the Ct of the region of the targeted gene(s) or locus(loci) which is replaced by successful targeting (i.e., a LOA assay). The Ct is a quantity that reflects the amount of starting DNA for each of the TAQMAN® probes, i.e. a less abundant sequence requires more cycles of PCR to reach the threshold cycle. Decreasing by half the number of copies of the template sequence for a TAQMAN® reaction will result in an increase of about one Ct unit. TAQMAN® reactions in cells where one allele of the target gene(s) or locus(loci) has been replaced by homologous recombination will result in an increase of one Ct for the target TAQMAN® reaction without an increase in the Ct for the reference gene when compared to DNA from non-targeted cells. For a GOA assay, another TAQMAN® probe can be used to determine the Ct of the nucleic acid insert that is replacing the targeted gene(s) or locus(loci) by successful targeting.

Because paired gRNAs can create large Cas-mediated deletions at a target genomic locus, it can be useful augment standard LOA and GOA assays to verify correct targeting by LTVECs (i.e., in cells other than one-cell stage embryos). For example, LOA and GOA assays alone may not distinguish correctly targeted cell clones from clones in which a large Cas-induced deletion of the target genomic locus coincides with random integration of a LTVEC elsewhere in the genome, particularly if the GOA assay employs a probe against a selection cassette within the LTVEC insert. Because the selection pressure in the targeted cell is based on the selection cassette, random transgenic integration of the LTVEC elsewhere in the genome will generally include the selection cassette and adjacent regions of the LTVEC but will exclude more distal regions of the LTVEC. For example, if a portion of an LTVEC is randomly integrated into the genome, and the LTVEC comprises a nucleic acid insert of around 5 kb or more in length with a selection cassette adjacent to the 3' homology arm, generally the 3' homology arm but not the 5' homology arm will be transgenically integrated with the selection cassette. Alternatively, if the selection cassette adjacent to the 5' homology arm, generally the 5' homology arm but not the 3' homology arm will be transgenically integrated with the selection cassette. As an example, if LOA and GOA assays are used to assess targeted integration of the LTVEC, and the GOA assay utilizes probes against the selection cassette, a heterozygous deletion at the target genomic locus combined with a random transgenic integration of the LTVEC will give the same readout as a heterozygous targeted integration of the LTVEC at the target genomic locus. To verify correct targeting by the LTVEC, retention assays can be used, alone or in conjunction with LOA and/or GOA assays.

Retention assays determine copy numbers of a DNA template in the 5' target sequence (corresponding to the 5' homology arm of the LTVEC) and/or the 3' target sequence (corresponding to the 3' homology arm of the LTVEC). In particular, determining the copy number of a DNA template in the target sequence corresponding to the homology arm that is adjacent to the selection cassette is useful. In diploid cells, copy numbers greater than two generally indicate transgenic integration of the LTVEC randomly outside of the target genomic locus rather than at the target genomic locus, which is undesirable. Correctly targeted clones will retain a copy number of two. In addition, copy numbers of less than two in such retention assays generally indicate large Cas-mediated deletions extending beyond the region targeted for deletion, which are also undesirable. See, e.g., US 2016/0145646 and WO 2016/081923, each of which is herein incorporated by reference in its entirety for all purposes.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes). Conventional assays for screening for targeted modifications, such as long-range PCR, Southern blotting, or Sanger sequencing, can also be used. Such assays typically are used to obtain evidence for a linkage between the inserted targeting vector and the targeted genomic locus. For example, for a long-range PCR assay, one primer can recognize a sequence within the inserted DNA while the other recognizes a target genomic locus sequence beyond the ends of the targeting vector's homology arms.

Next generation sequencing (NGS) can also be used for screening, particularly in one-cell stage embryos that have been modified. Next-generation sequencing can also be referred to as "NGS" or "massively parallel sequencing" or "high throughput sequencing." Such NGS can be used as a screening tool in addition to the MOA assays and retention assays to define the exact nature of the targeted genetic modification and to detect mosaicism. Mosaicism refers to the presence of two or more populations of cells with different genotypes in one individual who has developed from a single fertilized egg (i.e., zygote). In the methods disclosed herein, it is not necessary to screen for targeted clones using selection markers. For example, the MOA and NGS assays described herein can be relied on without using selection cassettes.

H. Methods of Making Genetically Modified Non-Human Animals

Genetically modified non-human animals can be generated employing the various methods disclosed herein. Any convenient method or protocol for producing a genetically modified organism, including the methods described herein, is suitable for producing such a genetically modified non-human animal. Such methods starting with genetically modifying a pluripotent cell such as an embryonic stem (ES) cell generally comprise: (1) modifying the genome of a pluripotent cell that is not a one-cell stage embryo using the methods described herein; (2) identifying or selecting the genetically modified pluripotent cell; (3) introducing the genetically modified pluripotent cell into a host embryo; and (4) implanting and gestating the host embryo comprising the genetically modified pluripotent cell in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein. The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. The pluripotent cell can be, for example, an ES cell (e.g., a rodent ES cell, a mouse ES cell, or a rat ES cell) as discussed elsewhere herein. See, e.g., U.S. Pat. No. 7,294,754, herein incorporated by reference in its entirety for all purposes.

Alternatively, such methods starting with genetically modifying a one-cell stage embryo generally comprise: (1) modifying the genome of a one-cell stage embryo using the methods described herein; (2) identifying or selecting the genetically modified embryo; and (3) implanting and gestating the genetically modified embryo in a surrogate mother. The surrogate mother can then produce F0 generation non-human animals comprising the targeted genetic modification and capable of transmitting the targeted genetic modification though the germline. Animals bearing the genetically modified genomic locus can be identified via a modification of allele (MOA) assay as described herein.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of a non-human animal to form an embryo; and (5) allowing the embryo to develop. In such methods, oocytes are generally retrieved from deceased animals, although they may be isolated also from either oviducts and/or ovaries of live animals. Oocytes can be matured in a variety of media known to those of ordinary skill in the art prior to enucleation. Enucleation of the oocyte can be performed in a number of manners well known to those of ordinary skill in the art. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in medium well known to those of ordinary skill in the art and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal that comprise the targeted genetic modification. It is recognized that depending on the method used to generate the F0 animal, the number of cells within the F0 animal that have the targeted genetic modification will vary. The introduction of the donor ES cells into a pre-morula stage embryo from a corresponding organism (e.g., an 8-cell stage mouse embryo) via, for example, the VELOCIMOUSE® method allows for a greater percentage of the cell population of the F0 animal to comprise cells having the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted genetic modification. In addition, at least one or more of the germ cells of the F0 animal can have the targeted genetic modification.

I. Types of Non-Human Animals and Cells

The methods provided herein employ non-human animals and cells and embryos from non-human animals. Such non-human animals are preferably mammals, such as rodents (e.g., rats, mice, and hamsters). Other non-human mammals include, for example, non-human primates, monkeys, apes, cats, dogs, rabbits, horses, bulls, deer, bison, livestock (e.g., bovine species such as cows, steer, and so forth; ovine species such as sheep, goats, and so forth; and porcine species such as pigs and boars). The term "non-human" excludes humans.

A non-human animal cell employed in the methods provided herein can be, for example, a totipotent cell or a pluripotent cell (e.g., an embryonic stem (ES) cell such as a rodent ES cell, a mouse ES cell, or a rat ES cell). Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The non-human animal cells employed in the methods provided herein can also include one-cell stage embryos (i.e., fertilized oocytes or zygotes). Such one-cell stage embryos can be from any genetic background (e.g., BALB/c, C57BL/6, 129, or a combination thereof), can be fresh or frozen, and can be derived from natural breeding or in vitro fertilization.

Mice and mouse cells employed in the methods provided herein can be from any strain, including, for example, a 129 strain, a C57BL/6 strain, a BALB/c strain, a Swiss Webster strain, a mix of 129 and C57BL/6, strains, a mix of BALB/c and C57BL/6 strains, a mix of 129 and BALB/c strains, and a mix of BALB/c, C57BL/6, and 129 strains. For example, a mouse or mouse cell employed in the methods provided herein can be at least partially from a BALB/c strain (e.g., at least about 25%, at least about 50%, at least about 75% derived from a BALB/c strain, or about 25%, about 50%, about 75%, or about 100% derived from a BALB/c strain). In one example, the mice or mouse cells can have a strain comprising 50% BALB/c, 25% C57BL/6, and 25% 129. Alternatively, the mice or mouse cells can comprise a strain or strain combination that excludes BALB/c.

Examples of 129 strains and C57BL strains are disclosed elsewhere herein. Mice and mouse cells employed in the methods provided herein can also be from a mix of an aforementioned 129 strain and an aforementioned C57BL/6 strain (e.g., 50% 129 and 50% C57BL/6). Likewise, mice and mouse cells employed in the methods provided herein can be from a mix of aforementioned 129 strains or a mix of aforementioned BL/6 strains (e.g., the 129S6 (129/SvEvTac) strain). A specific example of a mouse ES cell is a VGF1 mouse ES cell. VGF1 mouse ES cells (also known as F1H4) were derived from hybrid embryos produced by crossing a female C57BL/6NTac mouse to a male 129S6/SvEvTac mouse. See, e.g., Auerbach et al. (2000) *Biotechniques* 29, 1024-1028, herein incorporated by reference in its entirety for all purposes.

Rats or rat cells employed in the methods provided herein can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats or rat cells can also be obtained from a strain derived from a mix of two or more strains recited above. For example, the rat or rat cell can be from a DA strain or an ACI strain. The ACI rat strain is characterized as having black agouti, with white belly and feet and an $RT1^{av1}$ haplotype. Such strains are available from a variety of sources including Harlan Laboratories. An example of a rat ES cell line from an ACI rat is an ACI.G1 rat ES cell. The Dark Agouti (DA) rat strain is characterized as having an agouti coat and an $RT1^{av1}$ haplotype. Such rats are available from a variety of sources including Charles River and Harlan Laboratories. Examples of rat ES cell lines from a DA rat are the DA.2B rat ES cell line and the DA.2C rat ES cell line. In some cases, the rats or rat cells are from an inbred rat strain. See, e.g., US 2014/0235933 A1, herein incorporated by reference in its entirety for all purposes.

Cells that have been implanted into a host embryo can be referred to as "donor cells." The donor cell can be from the same strain as the host embryo or from a different strain. Likewise, the surrogate mother can be from the same strain as the donor cell and/or the host embryo, or the surrogate mother can be from a different strain as the donor cell and/or the host embryo.

A variety of host embryos can be employed in the methods and compositions disclosed herein. For example, a donor cell (e.g., donor ES cell) can be introduced into a pre-morula stage embryo (e.g., an 8-cell stage embryo) from a corresponding organism. See, e.g., U.S. Pat. Nos. 7,576,259; 7,659,442; 7,294,754; and US 2008/0078000, each of which is herein incorporated by reference in its entirety for all purposes. In other methods, the donor cells may be implanted into a host embryo at the 2-cell stage, 4-cell stage, 8-cell stage, 16-cell stage, 32-cell stage, or 64-cell stage. The host embryo can also be a blastocyst or can be a pre-blastocyst embryo, a pre-morula stage embryo, a morula stage embryo (e.g., an aggregated morula stage embryo), an uncompacted morula stage embryo, or a compacted morula stage embryo. When employing a mouse embryo, the host embryo stage can be a Theiler Stage 1 (TS1), a TS2, a TS3, a TS4, a TS5, and a TS6, with reference to the Theiler stages described in Theiler (1989) "The House Mouse: Atlas of Mouse Development," Springer-Verlag, New York, herein incorporated by reference in its entirety for all purposes. For example, the Theiler Stage can be selected from TS1, TS2, TS3, and TS4. In some methods, the host embryo comprises a zona pellucida, and the donor cell is an ES cell that is introduced into the host embryo through a hole in the zona pellucida. In other methods, the host embryo is a zona-less embryo.

III. Methods of Screening Compounds

The non-human animals having the Fbn1 mutations described herein can be used for screening compounds for activity potentially useful in inhibiting or reducing neonatal progeroid syndrome with congenital lipodystrophy (NPSCL) or ameliorating NPSCL-like symptoms (e.g., congenital lipodystrophy-like symptoms) or screening compounds for activity potentially harmful in promoting or exacerbating NPSCL. Compounds having activity inhibiting or reducing NPSCL or ameliorating NPSCL-like symptoms are potentially useful as therapeutics or prophylactics against NPSCL. Compounds having activity promoting or exacerbating NPSCL are identified as toxic and should be avoided as therapeutics or in other circumstances in which they may come into contact with humans (e.g., in foods, agriculture, construction, or water supply).

Examples of compounds that can be screened include antibodies, antigen-binding proteins, site-specific DNA binding proteins (e.g., CRISPR-Cas complexes), polypeptides, beta-turn mimetics, polysaccharides, phospholipids, hormones, prostaglandins, steroids, aromatic compounds, heterocyclic compounds, benzodiazepines, oligomeric N-substituted glycines, and oligocarbamates. Large combinatorial libraries of the compounds can be constructed by the encoded synthetic libraries (ESL) method described in WO 1995/012608, WO 1993/006121, WO 1994/008051, WO 1995/035503, and WO 1995/030642, each of which is herein incorporated by reference in its entirety for all purposes. Peptide libraries can also be generated by phage display methods. See, e.g., U.S. Pat. No. 5,432,018, herein incorporated by reference in its entirety for all purposes. Use of libraries of guide RNAs for targeting CRISPR-Cas systems to different genes are disclosed, e.g., in WO 2014/204727, WO 2014/093701, WO 2015/065964, and WO 2016/011080, each of which is herein incorporated by reference in its entirety for all purposes.

Animal-based assays generally involve administering a compound to the Fbn1 mutant non-human animal and assessing symptoms closely resembling those of NPSCL in humans for change in response. The change can be assessed from levels of the symptom before and after contacting the non-human animal with the compound or by performing a control experiment performed with a control animal having the same Fbn1 mutation (e.g., wild type cohort sibling) without the compound.

Suitable NPSCL-like signs or symptoms that can be monitored include body weight, lean mass, fat mass, white adipose mass (e.g., normalized by body weight), body fat percentage, food intake normalized by body weight, and kyphosis, as disclosed elsewhere herein. For example, white adipose tissue mass (e.g., normalized by body weight) can be monitored. These symptoms can be monitored in combination with one or more of the following: glucose tolerance, serum cholesterol levels, serum triglyceride levels, and serum non-esterified fatty acid levels. Likewise, these symptoms can be monitored in combination with one or more of the following: glucose tolerance, serum cholesterol levels, serum triglyceride levels, serum non-esterified fatty acid levels, liver weight, brown adipose tissue (BAT) weight, visceral white adipose tissue (WAT) weight, WAT weight normalized to body weight, metabolic rate normalized to body weight, energy expenditure, and insulin sensitivity on high-fat diet. For example, exacerbation of such NPSCL-like symptoms can result in one or more of decreased body weight, decreased lean mass, decreased fat mass, decreased white adipose tissue (e.g., normalized by body weight), decreased body fat percentage, increased food intake normalized by body weight, and increased kyphosis compared to the levels of the symptoms before contacting with the compound or compared to the levels of symptoms in the control non-human animal. Such decreases or increases can occur with one or more of decreased liver weight, preserved brown adipose tissue (BAT) weight (e.g., normalized by body weight), decreased visceral white adipose tissue (WAT) weight, decreased WAT weight normalized to body weight, elevated metabolic rate normalized to body weight, increased energy expenditure, improved glucose tolerance, and improved insulin sensitivity on high-fat diet. Such decreases or increases can occur with one or more of the following remaining normal: glucose tolerance, serum cholesterol levels, serum triglyceride levels, and serum non-esterified fatty acid levels. Alternatively, amelioration of such NPSCL-like symptoms can result in one or more of increased body weight, increased lean mass, increased fat mass, increased body fat percentage, decreased food intake normalized by body weight, and decreased kyphosis compared to the levels of the symptoms before contacting with the compound or compared to the levels of symptoms in the control non-human animal. Such decreases or increases can occur with one or more of increased liver weight, preserved or altered brown adipose tissue (BAT) weight (e.g., normalized by body weight), increased visceral white adipose tissue (WAT) weight, increased WAT weight normalized to body weight, decreased metabolic rate normalized to body weight, decreased energy expenditure, decreased glucose tolerance, and decreased insulin sensitivity on high-fat diet. Such symptoms can be assayed as described in the examples provided herein. The decrease or increase can be statistically significant. For example, the decrease or increase can be by at least about 1%, at least about 2%, at least about 3%, at least about 4%, at least about 5%, at least about 10%, at least about 15%, at least about 20%, at least about 30%, at least about 40%, at least about 50%, at least about 60%, at least about 70%, at least about 80%, at least about 90%, or 100%.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

TABLE 1

Description of Sequences.

| SEQ ID NO | Type | Description |
|---|---|---|
| 1 | DNA | Human WT FBN1 Nucleic Acid Fragment in FIG. 1 |
| 2 | Protein | Human WT FBN1 Protein Fragment in FIG. 1 |
| 3 | DNA | Human Variant FBN1 Fragment in FIG. 1 |
| 4 | Protein | Human Variant FBN1 Protein Fragment in FIG. 1 |
| 5 | DNA | Mouse WT Fbn1 Nucleic Acid Fragment from FIG. 1 |
| 6 | Protein | Mouse WT Fbn1 Protein Fragment from FIG. 1 |
| 7 | DNA | Mouse Fbn1 Variant MAID 8501 Nucleic Acid Fragment from FIG. 1 |
| 8 | Protein | Mouse Fbn1 Variant MAID 8501 Protein Fragment from FIG. 1 |
| 9 | DNA | Human WT FBN1 Nucleic Acid Fragment in FIG. 3 |

TABLE 1-continued

Description of Sequences.

| SEQ ID NO | Type | Description |
|---|---|---|
| 10 | Protein | Human WT FBN1 Protein Fragment in FIG. 3 |
| 11 | DNA | Human Variant FBN1 Nucleic Acid Fragment in FIG. 3 |
| 12 | Protein | Human Variant FBN1 Protein Fragment in FIG. 3 |
| 13 | DNA | Mouse WT Fbn1 Nucleic Acid Fragment from FIG. 3 |
| 14 | Protein | Mouse WT Fbn1 Protein Fragment from FIG. 3 |
| 15 | DNA | Mouse Fbn1 Variant MAID 8502 Nucleic Acid Fragment from FIG. 3 |
| 16 | Protein | Mouse Fbn1 Variant MAID 8502 Protein Fragment from FIG. 3 |
| 17 | Protein | Mouse Fbn1 Variant MAID 8520 Protein Fragment from FIG. 3 |
| 18 | Protein | Mouse Fbn1 Variant MAID 8502 Protein Fragment from FIG. 3 |
| 19 | DNA | Human WT FBN1 cDNA |
| 20 | DNA | Mouse WT Fbn1 cDNA |
| 21 | DNA | Mouse Fbn1 cDNA with MAID 8501 Mutations |
| 22 | DNA | Mouse Fbn1 cDNA with MAID 8520 Mutations |
| 23 | DNA | Mouse Fbn1 cDNA with MAID 8502 Mutations |
| 24 | DNA | Human WT Penultimate FBN1 Exon |
| 25 | DNA | Mouse WT Penultimate Fbn1 Exon |
| 26 | DNA | Mouse Penultimate Fbn1 Exon with MAID 8501 Mutations |
| 27 | DNA | Mouse Penultimate Fbn1 Exon with MAID 8520 Mutations |
| 28 | DNA | Mouse Penultimate Fbn1 Exon with MAID 8502 Mutations |
| 29 | Protein | Human WT FBN1 Protein |
| 30 | Protein | Mouse WT Fbn1 Protein |
| 31 | Protein | MAID 8501 Protein |
| 32 | Protein | MAID 8520 Protein |
| 33 | Protein | MAID 8502 Protein |
| 34 | Protein | Extremely Positively Charged C-Terminus |
| 35 | Protein | Less Positively Charged C-Terminus |
| 36 | Protein | Amino Acid Recognition Sequence for Furin Family Proteases |
| 37 | DNA | mGA for MAID 8501 |
| 38 | DNA | Donor for MAID 8501 |
| 39 | DNA | Generic Guide RNA Recognition Sequence v1 |
| 40 | DNA | Generic Guide RNA Recognition Sequence v2 |
| 41 | DNA | Generic Guide RNA Recognition Sequence v3 |
| 42 | Protein | C-terminus of MAID 8520 Protein |
| 43 | Protein | C-terminus of MAID 8502 Protein |
| 44 | DNA | Insertion in MAID 8520 Allele |
| 45 | Protein | Final 14 Amino Acids of Protein Encoded by MAID 8501 Allele |
| 46 | Protein | Final 14 Amino Acids of Protein Encoded by MAID 8502 Allele |
| 47 | Protein | Final 14 Amino Acids of Protein Encoded by MAID 8520 Allele |

EXAMPLES

Example 1. Generation of MAID 8501 Fbn1 Mutant Mice with Truncated C-Terminus A mutant Fbn1 mouse allele was generated to recreate a human mutant FBN1 allele. Using NM_007993.2 as a reference sequence, the mutation is c.8213_8214delinsACT. This mutation, which was created by inserting an A between c.8212 and 8213 and making a G>T substitution at c.8214, results in a premature termination codon in the penultimate exon of Fbn1. The mutant allele is indicated as MAID 8501. See FIG. 1. The mutation is within the last 50 nucleotides of the penultimate exon and is predicted to escape mRNA nonsense-mediated decay (NMD), leading to expression of a mutant, truncated profibrillin protein.

To generate the mutant allele, CRISPR/Cas9 components were introduced into a C57BL/6 one-cell stage embryo via pronuclear injection or cytoplasmic mRNA piezo injections together with a donor template. The sequence of the guide RNA DNA-targeting sequence is set forth in SEQ ID NO: 37, and the sequence of the donor is set forth in SEQ ID NO: 38. NGS was used to screen for correctly targeted clones. The targeting results are set forth in Table 2.

TABLE 2

Targeting results for MAID 8501.

| Delivery | Cas9 | Concentration (ng/µL) Cas9/sgRNA/Donor | Monoallelic Mutation | | Biallelic Mutation | |
|---|---|---|---|---|---|---|
| | | | NHEJ | HR | NHEJ | HR |
| PNI | Protein | 40/40/15 | 18% | 12% | 17% | 3% |
| CI | mRNA | 100/50/100 | 36% | 24% | 19% | 10% |

F0 founder mice were generated following microinjection of embryos into pseudopregnant female mice. As shown in FIG. 2, no male or female mice homozygous for the MAID 8501 Fbn1 mutation survived past 40 days, whereas male and female heterozygous mice survived much longer.

Example 2. Generation of MAID 8520 Fbn1 Mutant Mice with Truncated C-Terminus In another experiment, a guide RNA sequence and donor sequence were designed to generate a mutant Fbn1 allele corresponding to the human c.8155_8156del Fbn1 allele, which has a deletion of two base pairs in coding exon 64 (the penultimate exon) causing a frameshift with a subsequent premature termination codon 17 codons downstream of p.Lys2719. The predicted mutant allele is indicated as MAID 8502. See FIG. 3.

To generate the mutant allele, CRISPR/Cas9 components were introduced into a C57BL/6 one-cell stage embryo via pronuclear injection or cytoplasmic mRNA piezo injections together with a donor template. One clone that was generated had the MAID 8520 mutant allele shown in FIG. 3 rather than the expected MAID 8502 allele. The MAID 8520 mutant allele also results in a premature termination of the encoded Fbn1 protein as shown in FIG. 3.

Figure 4:
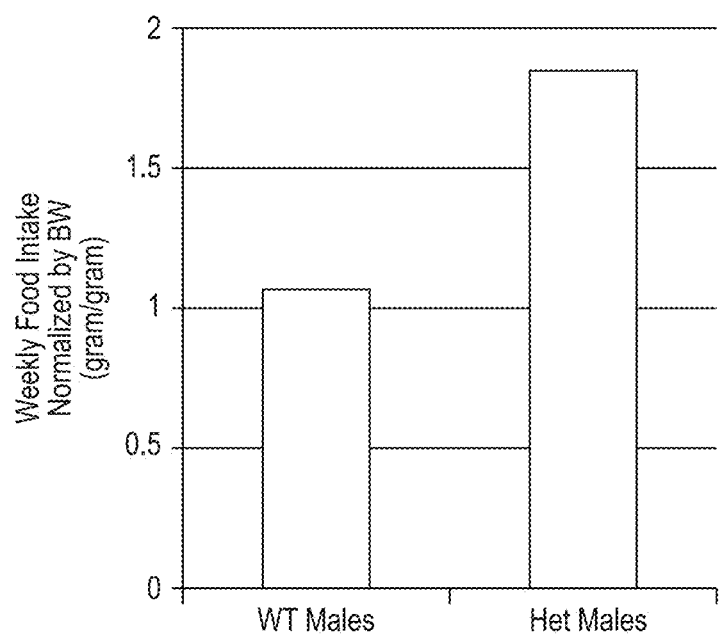
FIG. 4 shows the weekly food intake normalized by body weight for male wild type mice and F1 generation mice heterozygous for the engineered mouse Fbn1 gene variant MAID 8520.
Figure 5:
FIG. 5 shows 3-month old male F1 male wild type mice and 3-month old F1 male mice heterozygous for the engineered mouse Fbn1 gene variant MAID 8520.
Figure 6:
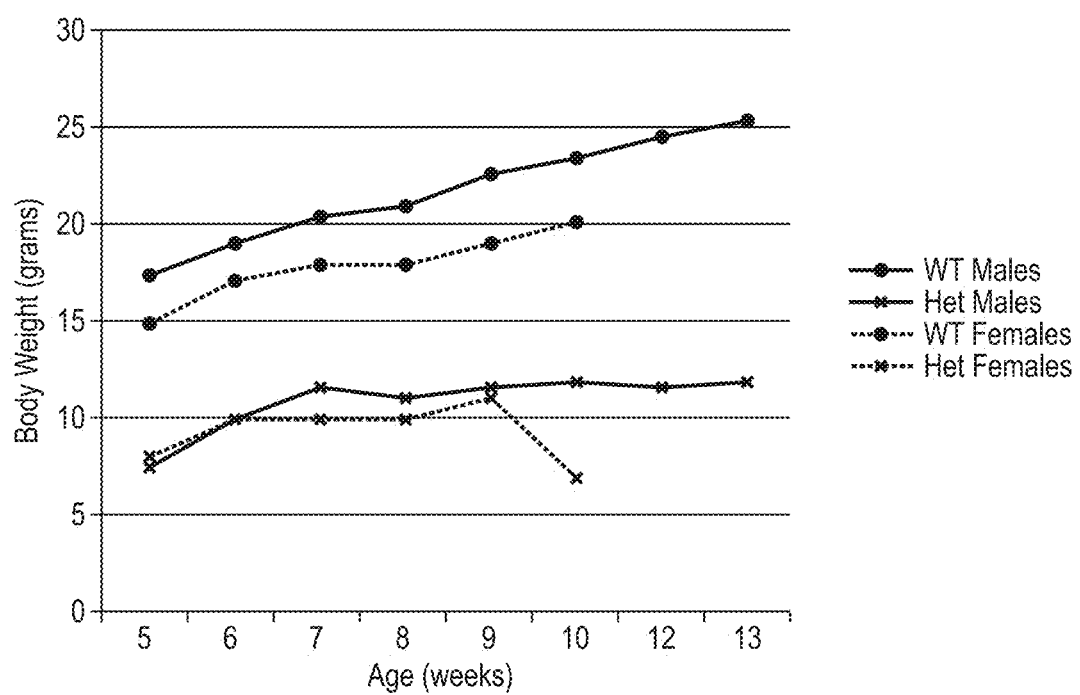
FIG. 6 shows the body weights of F1 mice by age, including wild type male mice, wild type female mice, and male and female mice heterozygous for the engineered mouse Fbn1 gene variant MAID 8520.
Figures 7C, 7D, 7E:
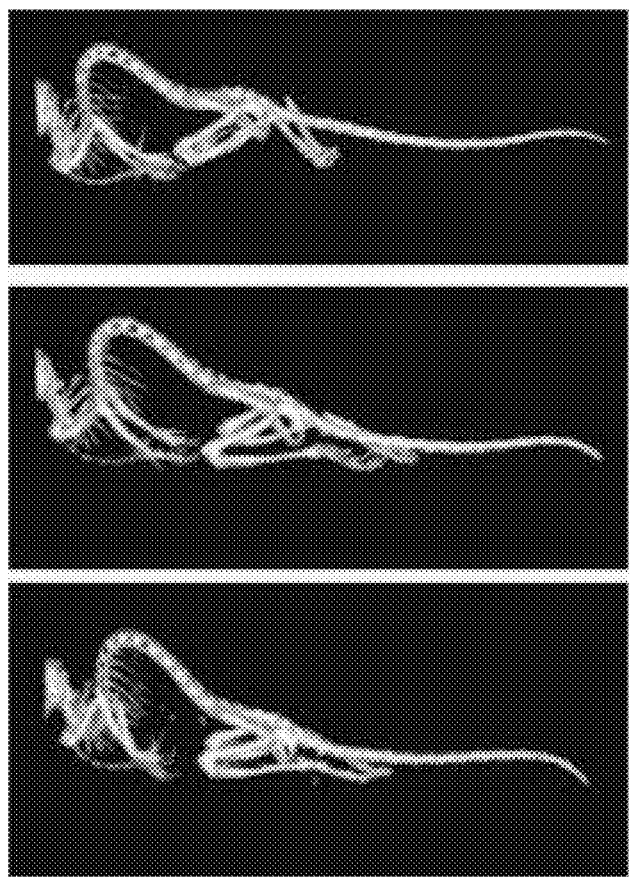
FIGS. 7A-7E show skeletons of wild type female mice (FIGS. 7A and 7B) and Fbn1 gene variant MAID 8520 heterozygous mice (FIGS. 7C-7E) showing uCT images of spinal kyphosis.
Figures 7A, 7B:
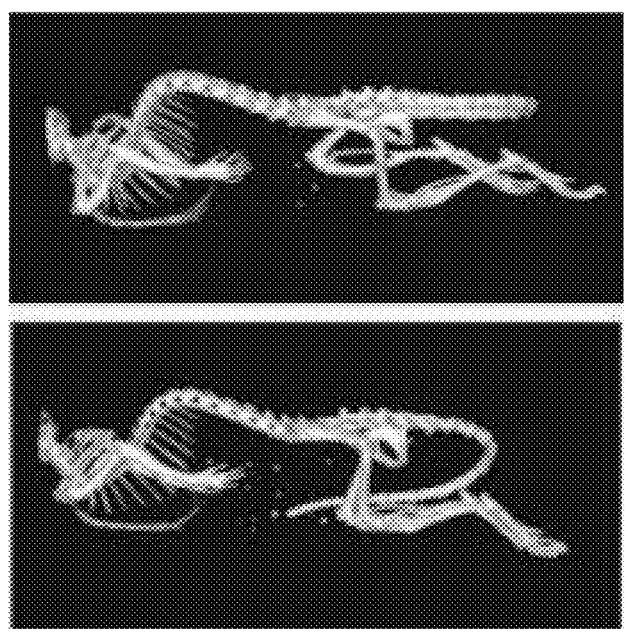

F0 founder mice were generated following microinjection of embryos into pseudopregnant female mice, and F1 generation mice were subsequently produced. Compared to wild type mice, the mice heterozygous for the Fbn1 mutation ate much more when normalized by body weight. See, e.g., FIG. 4, showing weekly food intake normalized by body weight (gram for gram), where heterozygous males ate approximately 1.7-fold more food than their wild type counterparts when normalized by body weight. Despite the increased food intake, the body weights of the male and female mice heterozygous for the Fbn1 mutation were consistently lower than the corresponding wild type mice over time. See, e.g., FIG. 5, showing two 3-month-old male F1 heterozygous mice on the left-hand side, and two 3-month-old wild type male F1 mice on the right-hand side. See also FIG. 6, showing the body weights of the F1 offspring from age 5 weeks to age 13 weeks. For example, whereas the body weights of the heterozygous mutant males were approximately 7 grams at 5 weeks and 12 grams at 13 weeks, the body weights of the corresponding wild type males were approximately 18 grams at 5 weeks and 25 grams at 13 weeks. These trends were also observed in the female mice.

Figure 8A:
FIGS. 8A-8C show assays related to body weight and fat mass.
Figure 8B:
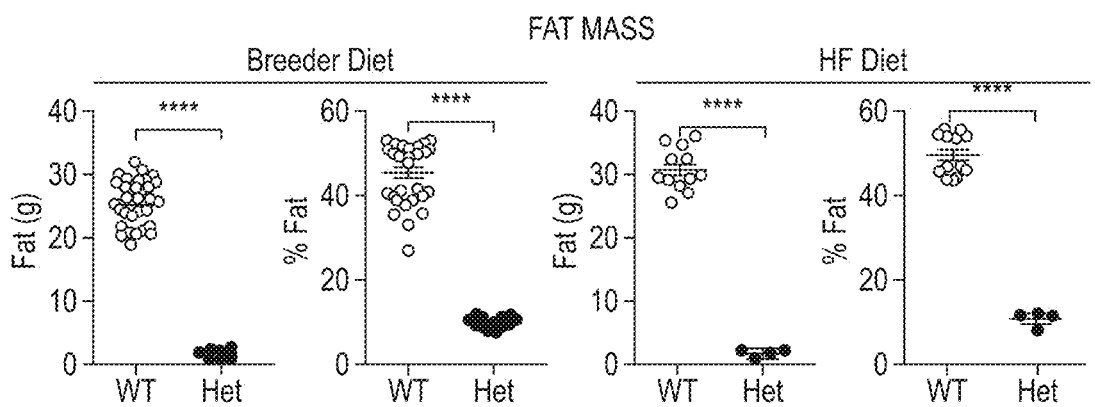
Figure 8C:
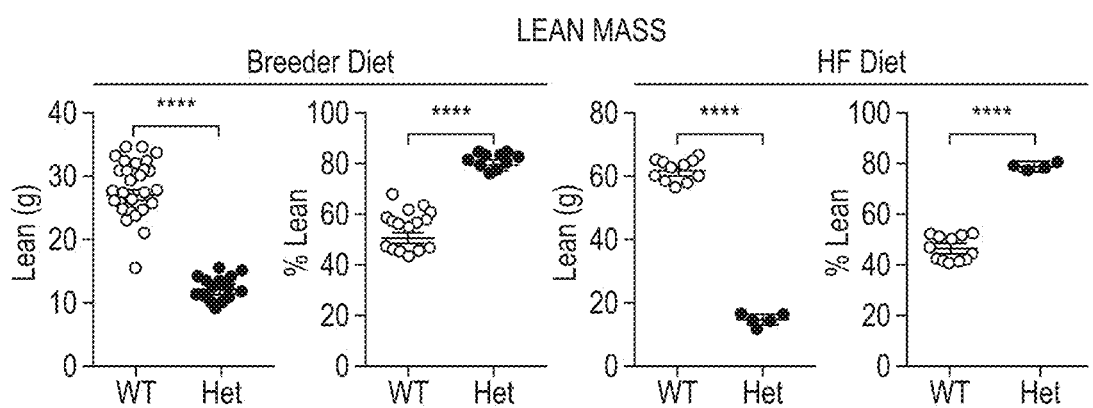
Figure 13A:
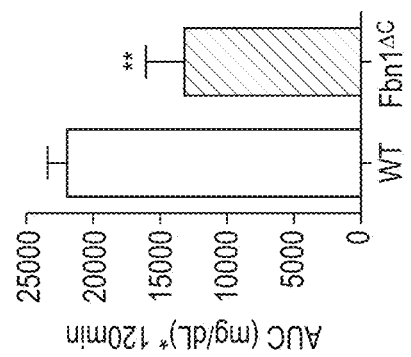
FIGS. 13A-13D show an insulin tolerance test of female Fbn1 gene variant MAID 8520 heterozygous mice placed on a 60% high-fat diet for 20 weeks.
Figure 13B:
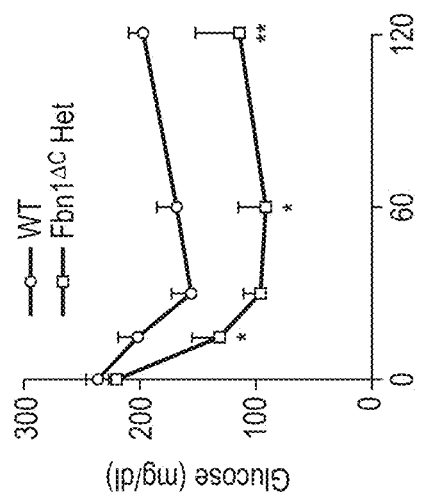
Figure 13C:
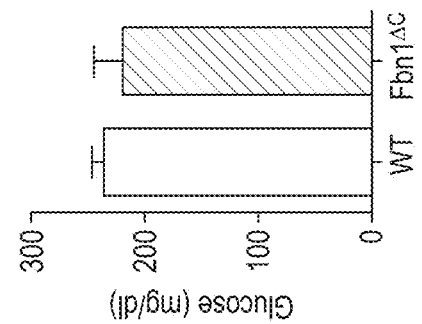
Figure 13D:
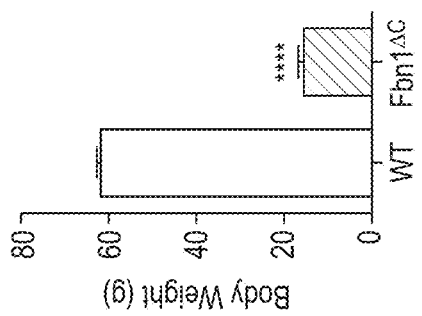

Further analysis of the heterozygous females compared to the wild type females showed kyphosis (i.e., exaggerated forward rounding of the back) in the heterozygous mutant females when compared to the wild type females. See FIGS. 7A-7E. Likewise, the heterozygous females had very little fat compared to their wild type counterparts. As shown in FIGS. 8A-8C, the heterozygous mutant female mice had statistically significant lower levels of body weight, lean mass, and fat mass as measured by ECHOMRI™, which is used to measure fat and lean mass in rodents. These differences held even if the mice were fed a 60% high-fat diet for 21 weeks. Despite the absence of body fat, heterozygous mutant females and corresponding wild type females showed similar glucose tolerance (oral glucose tolerance, given 2 mg/kg after an overnight fast) on a chow diet and no elevations in serum cholesterol, triglycerides, and non-esterified fatty acids (measured by ADVIA). See, e.g., FIGS. 9A-9F and 10A-10F, respectively.

Further analysis of the heterozygous mutant females showed preservation of the brown adipose tissue (BAT) depot despite near complete loss of the visceral white adipose. See FIGS. 11A-11H. The preservation of BAT led us to examine the energy expenditure of the heterozygous mutant females after 12 weeks of 60% high-fat diet feeding. See FIGS. 12A-12H. Metabolic cage analysis using a Columbia Instruments Oxymax CLAMS system showed the mice had an elevated metabolic rate normalized to body weight as indicated by their $VO_2$, $VCO_2$ and energy expenditure (Energy). After 20 weeks on a high-fat diet, these mice also exhibited improved glucose tolerance. See FIGS. 13A-13D.

The mice heterozygous for the C-terminal deletion in Fibrillin-1 are lean with great reduction of white fat depots, but they have preserved brown adipose, increased energy expenditure, similar glucose tolerance, improved insulin sensitivity on high-fat diet, and no elevation in serum lipids compared to wild type mice. This recapitulates the FBN1 phenotype observed in human NPSCL patients in that, unlike many lipodystrophic syndromes, these particular mice have a normal metabolic profile in terms of glucose homeostasis and circulating lipids despite having no visceral adipose tissue. Many other models of FBN1 mutant mice have grossly normal heterozygotes while the homozygotes have early postnatal or embryonic death. See, e.g., Pereira et al. (1999) *Proc. Natl. Acad. Sci. U.S.A.* 96(7):3819-3823, herein incorporated by reference in its entirety for all purposes. Our model shows a dominant heterozygous phenotype, which recapitulates many of the features of the human patients, allowing us to study therapeutic options. In particular, our model shows a loss of white adipose tissue while brown adipose tissue is preserved in combination with an improvement in insulin sensitivity despite the loss of white adipose tissue. Human NPSCL patients have normal glucose homeostasis despite loss of white adipose tissue, which our model reflects. Preservation of brown adipose tissue is likely the mechanism underlying the maintained/improved insulin sensitivity, as this may allow the mice to burn off the excess fat they are not able to store.

We claim:

1. A mouse whose genome comprises a mutation in the penultimate exon of time endogenous fibrin-1 (Fbn1) gene, wherein the mouse is heterozygous for time mutation, wherein the mutation results in disruption or ablation of time asprosin C-terminal cleavage product of pro-fibrillin-1, wherein expression of the mutant Fbn1 gene results in a C-terminally truncated Fbn1 protein, and wherein the mouse exhibits decreased body weight, decreased lean mass, and decreased fat mass when compared to a wild-type mouse.

2. The mouse of claim 1, wherein the mutant Fbn1 gene is operably linked to the endogenous Fbn1 promoter.

3. The mouse of claim 1, wherein the mutation is a frameshift mutation.

4. The mouse of claim 1, wherein the mutation results in a premature termination codon.

5. The mouse of claim 4, wherein the premature termination codon is in the penultimate or the final exon of the Fbn1 gene.

6. The mouse of claim 5, wherein the premature termination codon is in the final exon or is less than 55 base pairs upstream of the last exon-exon junction in the Fbn1 gene.

7. The mouse of claim 1, wherein the mutation results in a premature termination codon in the last coding exon.

8. The mouse of claim 1, wherein the mutation disrupts a basic amino acid recognition sequence for proprotein convertases of the furin family.

9. The mouse of claim 1, wherein the mutation is within about 50 base pairs of a furin recognition sequence.

10. The mouse of claim 1, wherein the C-terminally truncated Fbn1 protein has a positively charged C-terminus.

11. The mouse of claim 1, wherein the C-terminally truncated Fbn1 protein is truncated at a position corresponding to a position between amino acids 2700 and 2790, between amino acids 2710 and 2780, between amino acids 2720 and 2770, between amino acids 2730 and 2760, or between amino acids 2737 and 2755 in the wild type mouse Fbn1 protein set forth in SEQ ID NO: 30 when the C-terminally truncated Fbn1 protein is aligned with SEQ ID NO: 30.

12. The mouse of claim 11, wherein the C-terminally truncated Fbn1 protein is truncated such that the last amino acid is at a position corresponding to amino acid 2737, amino acid 2738, or amino acid 2755 in the wild type mouse Fbn1 protein set forth in SEQ ID NO: 30 when the C-terminally truncated Fbn1 protein is aligned with SEQ ID NO: 30.

13. The mouse of claim 1, wherein the C-terminally truncated Fbn1 protein has a C-terminus consisting of the sequence set forth in SEQ ID NO: 8, 42, 43, 45, 46, or 47.

14. The mouse of claim 11, wherein the C-terminally truncated Fbn1 protein is truncated such that the last amino acid is at a position corresponding to amino acid 2737 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 43 or 46.

15. The mouse of claim 11, wherein the C-terminally truncated Fbn1 protein is truncated such that the last amino acid is at a position corresponding to amino acid 2738 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 8 or 45.

16. The mouse of claim 11, wherein the C-terminally truncated Fbn1 protein is truncated such that the last amino acid is at a position corresponding to amino acid 2755 in the wild type mouse Fbn1 protein set forth in SEQ ID NO: 30 when the C-terminally truncated Fbn1 protein is aligned with SEQ ID NO: 30, and wherein the C-terminus of the C-terminally truncated Fbn1 protein consists of the sequence set forth in SEQ ID NO: 42 or 47.

17. The mouse of claim 1, wherein mRNA expressed from the Fbn1 gene escapes mRNA nonsense-mediated decay (NMD).

18. The mouse of claim 1, wherein the mutated penultimate exon of the Fbn1 gene comprises the mutations in SEQ ID NO: 26, 27, or 28 relative to the wild type mouse Fbn1 penultimate exon sequence set forth in SEQ ID NO: 25.

19. The mouse of claim 1, wherein the C-terminally truncated Fbn1 protein consists of the sequence set forth in SEQ ID NO: 31, 32, or 33.

20. The mouse of claim 1, wherein the penultimate exon is axon 64, and the mutation comprises an insertion or deletion that causes a −1 frameshift and results in a premature termination codon at the 3' end of exon 64 or the 5' end of exon 65.

21. The mouse of claim 20, wherein the mutation comprises an insertion in exon 64 that causes a −1 frameshift and results in a premature termination codon at the 5' end of exon 65.

22. The mouse of claim 21, wherein the insertion is between positions corresponding to positions 8179 and 8180 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8241 in the wild type mouse Fbn1 coding sequence set forth in SEQ ID NO: 20 when the Fbn1 gene comprising the mutation is aligned with SEQ ID NO: 20.

23. The mouse of claim 20, wherein the mutation comprises an insertion or deletion in exon 64 that causes a −1 frameshift and results in a premature termination codon at the 3' end of exon 64.

24. The mouse of claim 23, wherein the mutation comprises an insertion between positions corresponding to positions 8209 and 8210 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is aligned with SEQ ID NO: 20.

25. The mouse of claim 23, wherein the mutation comprises a deletion starting at a position corresponding to position 8161 in the wild type mouse Fbn1 coding sequence set forth in SEQ ID NO: 20 when the Fbn1 gene comprising the mutation is aligned with SEQ ID NO: 20, and/or the premature termination codon is at a position corresponding to position 8214 in the wild type mouse Fbn1 coding sequence set forth in SEQ ID NO: 20 when the Fbn1 gene comprising the mutation is aligned with SEQ ID NO: 20.

26. The mouse of claim 20, wherein the C-terminally truncated Fbn1 protein has a positively charged C-terminus.

27. The mouse of claim 1, wherein the mouse exhibits one or more of the following: decreased white adipose tissue normalized by body weight, decreased white adipose tissue in combination with preserved brown adipose tissue normalized by body weight, decreased body fat percentage, increased food intake normalized by body weight, and increased kyphosis.

28. The mouse of claim 27, wherein the mouse exhibits one or more of the following: increased metabolic rate, improved insulin sensitivity, normal glucose tolerance, normal serum cholesterol levels, normal serum triglyceride levels, and normal serum non-esterified fatty acid levels.

29. The mouse of claim 27, wherein the mouse exhibits decreased white adipose tissue normalized by body weight and at least one of improved insulin sensitivity, normal glucose tolerance, normal serum cholesterol levels, normal serum triglyceride levels, and normal serum non-esterified fatty acid levels.

30. The mouse of claim 28, wherein the mouse exhibits decreased white adipose tissue normalized by body weight and improved insulin sensitivity.

* * * * *

UNITED STATES PATENT AND TRADEMARK OFFICE
CERTIFICATE OF CORRECTION

PATENT NO. : 10,548,302 B2
APPLICATION NO. : 15/663410
DATED : February 4, 2020
INVENTOR(S) : Charleen Hunt et al.

Page 1 of 1

It is certified that error appears in the above-identified patent and that said Letters Patent is hereby corrected as shown below:

In the Claims

Claim 1, Column 187, Line 3, delete "time" and insert --the--
Claim 1, Column 187, Line 3, delete "fibrin-1" and insert --fibrillin-1--
Claim 1, Column 187, Line 4, delete "time" and insert --the--
Claim 1, Column 187, Line 5, delete "time" and insert --the--
Claim 20, Column 188, Line 21, delete "axon" and insert --exon--

Signed and Sealed this
Seventh Day of April, 2020

Andrei Iancu
*Director of the United States Patent and Trademark Office*